US012774467B2

(12) United States Patent
Pai et al.

(10) Patent No.: US 12,774,467 B2
(45) Date of Patent: Oct. 27, 2026

(54) IDENTIFYING NON-PRODUCTIVE SPLICE SITES

(71) Applicant: UNIVERSITY OF MASSACHUSETTS, Westborough, MA (US)

(72) Inventors: Athma A. Pai, Cambridge, MA (US); Jonathan K. Watts, Worcester, MA (US); Kaitlyn Brokaw, Worcester, MA (US); Eraj Shafiq Khokhar, Worcester, MA (US); Zachary Kartje, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 1048 days.

(21) Appl. No.: 17/781,569

(22) PCT Filed: Dec. 4, 2020

(86) PCT No.: PCT/US2020/063489

§ 371 (c)(1),
(2) Date: Jun. 1, 2022

(87) PCT Pub. No.: WO2021/113773

PCT Pub. Date: Jun. 10, 2021

(65) Prior Publication Data

US 2023/0022489 A1 Jan. 26, 2023

Related U.S. Application Data

(60) Provisional application No. 62/943,670, filed on Dec. 4, 2019, provisional application No. 62/943,672, filed on Dec. 4, 2019.

(51) Int. Cl.
*C12Q 1/6834* (2018.01)
*A61P 43/00* (2006.01)
*C12N 15/113* (2010.01)

(52) U.S. Cl.
CPC .......... *C12N 15/1138* (2013.01); *A61P 43/00* (2018.01); *C12Q 1/6834* (2013.01); *C12N 2310/11* (2013.01); *C12N 2310/315* (2013.01); *C12N 2310/322* (2013.01); *C12N 2310/3341* (2013.01); *C12N 2310/346* (2013.01); *C12N 2320/33* (2013.01)

(58) Field of Classification Search
CPC . C12Q 1/6834; C12Q 1/6806; C12N 2320/33
See application file for complete search history.

(56) References Cited

U.S. PATENT DOCUMENTS

| | | | |
|---|---|---|---|
| 5,684,143 | A | 11/1997 | Gryaznov et al. |
| 5,858,988 | A | 1/1999 | Wang |
| 6,017,755 | A | 1/2000 | Wrana et al. |
| 6,291,438 | B1 | 9/2001 | Wang |
| 7,399,845 | B2 | 7/2008 | Seth et al. |
| 7,427,672 | B2 | 9/2008 | Imanishi et al. |
| 2004/0171570 | A1 | 9/2004 | Allerson et al. |
| 2004/0259135 | A1 | 12/2004 | Cleary et al. |
| 2005/0130923 | A1 | 6/2005 | Bhat et al. |
| 2010/0311039 | A1 | 12/2010 | Lowe et al. |
| 2018/0223360 | A1 | 8/2018 | Hatchwell et al. |
| 2018/0371550 | A1 | 12/2018 | Komurov |
| 2019/0070213 | A1 | 3/2019 | Aznarez et al. |
| 2019/0330682 | A1 | 10/2019 | Goldrick et al. |

FOREIGN PATENT DOCUMENTS

| | | | |
|---|---|---|---|
| EP | 4069255 | A2 | 10/2022 |
| WO | WO 1999/014226 | A2 | 3/1999 |
| WO | WO 2008/101157 | A1 | 8/2008 |
| WO | WO 2008/150729 | A2 | 12/2008 |
| WO | WO 2008/154401 | A2 | 12/2008 |
| WO | WO 2009/006478 | A2 | 1/2009 |
| WO | WO 2015/193651 | A4 | 3/2016 |
| WO | WO 2017/087667 | A1 | 5/2017 |
| WO | WO 2017/106283 | A1 | 6/2017 |
| WO | WO 2017/106377 | A1 | 6/2017 |
| WO | WO 2018/162538 | A1 | 9/2018 |
| WO | WO 2018/169900 | A1 | 9/2018 |
| WO | WO 2019/038533 | A1 | 2/2019 |
| WO | WO 2021/113773 | A2 | 6/2021 |

OTHER PUBLICATIONS

Extended European Search Report received for European Patent Application No. 20897387.5, mailed on Jan. 23, 2024.
Lim et al., "Antisense Oligonucleotide Modulation of Non-productive Alternative Splicing Upregulates Gene Expression", Nature Communications, Jul. 9, 2020, 11(1): 3501.
Altieri et al., "The Influence of 4-thiouridine Labeling on Pre-mRNA Splicing Outcomes", PLoS One, Dec. 13, 2021, vol. 16, No. 12, Article No. e0257503, pp. 1-13.
Dobin et al., "STAR: Ultrafast Universal RNA-Seq Aligner", Bioinformatics, 2013, vol. 29, Issue 1, pp. 15-21.
Eckstein, "Phosphorothioate Oligodeoxynucleotides: What Is Their Origin and What Is Unique About Them?", Antisense and Nucleic Acid Drug Development, Apr. 2000, vol. 10, No. 2, pp. 117-121.
International Search Report and Written Opinion received for PCT Patent Application No. PCT/US2020/063489, mailed on May 27, 2021, 18 pages.

(Continued)

*Primary Examiner* — J. E. Angell
(74) *Attorney, Agent, or Firm* — LATHROP GPM LLP; James H. Velema, Esq.

(57) ABSTRACT

The present disclosure provides methods of identifying non-productive splice sites in target RNA transcripts and antisense oligonucleotides that increase the expression of said target RNA transcripts. In an embodiment, the target RNA transcript comprises ADAR, ARSA, ATPIA2, CACNAIA, DNMI, EIF2BI, EIF2B2, EIF2B5, IDUA, MFSD8, NF2, NPC1L PEXI, PRICKLE2, PRRT2, RAM, SETD5, SHANKS, SLC6A1, STXBPI, STX1B, and TCF4.

14 Claims, 5 Drawing Sheets

Specification includes a Sequence Listing.

(56) References Cited

OTHER PUBLICATIONS

Ittig et al., "Nuclear Antisense Effects In Cyclophilin A pre-mRNA Splicing By Oligonucleotides: A Comparison Of Tricyclo-DNA With LNA", Nucleic Acids Research, Jan. 1, 2004, vol. 32, Issue 1, pp. 346-353.
Ittig, et al., Oligonucleotide analogues: From supra-molecular principles to biological properties; Collective Symposium Series of the Academy of Sciences of the Czech Republic; Prague, 2005, pp. 21-26.
Ivanova et al. , "Tricyclo-DNA Containing Oligonucleotides as Steric Block Inhibitors of Human Immunodeficiency Virus Type 1 Tat-Dependent Trans-Activation and HIV-1 Infectivity", Oligonucleotides, Apr. 26, 2007, vol. 17, No. 1, pp. 54-65.
Jiang et al., "Gain of Toxicity from ALS/FTD-Linked Repeat Expansions in C90RF72 Is Alleviated by Antisense Oligonucleotides Targeting GGGGCC-Containing RNAs", Neuron, May 6, 2016, vol. 90, No. 3, pp. 535-550.
Kawashima et al., "Widespread Use of Non-productive Alternative Splice Sites in *Saccharomyces cerevisiae*", PLOS Genetics, Apr. 2014, vol. 10, Issue 4, pp. 1-15.
Pai, et al., "Numerous Recursive Sites Contribute to Accuracy of Splicing in Long Introns in Flies", PLOS Genetics, Aug. 27, 2018, vol. 14, No. 8, Article No. e1007588, pp. 1-24.
Partial Supplementary European Search Report received in EP Application No. 20897387.5, mailed on Oct. 16, 2023, 10 pages.
Renneberg et al., "Antisense Properties of Tricyclo-DNA", Nucleic Acids Research, Jul. 1, 2002, vol. 30, Issue 13, pp. 2751-2757.
Renneberg et al., "Exploring Hoogsteen and Reversed-Hoogsteen Duplex and Triplex Formation with Tricyclo-DNA Purine Sequences", Chembiochem, Aug. 2, 2004, vol. 5, Issue 8, pp. 1114-1118.
Renneberg et al., "Watson-Crick Base-Pairing Properties of Tricyclo-DNA", Journal of the American Chemical Society, May 7, 2002, vol. 124, No. 21, pp. 5993-6002.
Rusckowski et al., "Biodistribution and Metabolism of a Mixed Backbone Oligonucleotide (GEM 231) Following Single and Multiple Dose Administration in Mice", Antisense and Nucleic Acid Drug Development, Oct. 2000, vol. 10, No. 5, pp. 333-345.
Schwalb et al., "TT-Seq Maps the Human Transient Transcriptome", Science, Jun. 3, 2016, vol. 352, Issue 6290, pp. 1225-1228.
Sørensen et al., "α-L-ribo-Configured Locked Nucleic Acid (α-L-LNA): Synthesis and Properties", Journal of the American Chemical Society, 2002, vol. 124, No. 10, pp. 2164-2176.
Stein et al., "Inhibition of Vesivirus Infections in Mammalian Tissue Culture with Antisense Morpholino Oligomers", Antisense and Nucleic Acid Drug Development, Oct. 2001, vol. 11, No. 5, pp. 317-325.
Tran et al., "Differential Toxicity of Nuclear RNA Foci versus Dipeptide Repeat Proteins in a *Drosophila* Model of C90RF72 FTD/ALS", Neuron, Sep. 23, 2015, vol. 87, No. 7, pp. 1207-1214.
Vorobjev et al., "Nuclease Resistance and RNase H Sensitivity of Oligonucleotides Bridged by Oligomethylenediol and Oligoethylene Glycol Linkers", Antisense and Nucleic Acid Drug Development, Apr. 2011, vol. 11, No. 2, pp. 77-85.

IDENTIFYING NON-PRODUCTIVE SPLICE SITES

CROSS-REFERENCE TO RELATED APPLICATIONS

This application is a 35 U.S.C. § 371 filing of International Patent Application No. PCT/US2020/063489, filed Dec. 4, 2020, which claims the benefit of U.S. Provisional Application Ser. No. 62/943,672, filed Dec. 4, 2019, and U.S. Provisional Application Ser. No. 62/943,670, filed Dec. 4, 2019, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Jun. 1, 2022, is named 730313_UM9-249US_SL.txt and is 70.8 kilobytes in size.

BACKGROUND

The mechanism of mRNA splicing is a conserved and highly-regulated process. Nevertheless, cryptic or nonproductive splicing occurs when the spliceosome utilizes erroneous splice sites and generates transcripts that undergo nonsense-mediated mRNA decay. In cryptic or nonproductive splicing, spliceosome components can often bind to cryptic sites (with either canonical or non-canonical sequence elements) and improperly splice an mRNA molecule. This improper splice site usage can be called noisy, cryptic, or nonproductive splicing. The phenomenon of nonproductive splicing is particularly common in genes with long introns or many introns.

Noisy splicing most often results in non-productive transcripts that are targeted for degradation, e.g. by nonsense-mediated decay pathways. Thus, while these isoforms are rarely observed in steady-state gene expression measurements, they are likely to represent a large amount of the total transcriptional output of a gene.

Due to the transient and variable nature of these non-productive isoforms and the increased probability of weaker splice site usage in these isoforms, sites at which cryptic splicing consistently occur are difficult to identify through standard RNA-sequencing (RNA-seq) methods. In fact, standard RNA-seq data does not show rapidly degraded mRNA splice forms even though these account for a large part of the transcriptional activity of many genes.

Thus, there is a need to be able to systematically identify non-productive RNA transcript intermediates. Further, there is a need to be able to account for the usage of non-canonical cryptic sites, cell-type specific splicing intermediates, or the complexity of other molecular processes that may result in non-productive splicing intermediates. This is a challenging task given only information about steady-state mRNA levels and the fact that overall gene expression levels can be affected by many post-transcriptional mechanisms.

SUMMARY

In a first aspect, the disclosure provides a method of identifying a non-productive splice site in a target RNA transcript, the method comprising:

a) incubating a cell with an affinity label to facilitate incorporation of the affinity label into nascent RNA;

b) capturing the affinity labeled nascent RNA with a solid support comprising specificity for the affinity label;

c) isolating the affinity labeled nascent RNA;

d) sequencing the isolated affinity labeled nascent RNA; and e) identifying split reads that do not map to target RNA transcript exon-exon junctions; and f) calculating the probability that the split reads represent non-productive transcripts, thereby identifying non-productive splice sites in the target RNA transcript.

In a second aspect, the disclosure provides a method of identifying a non-productive splice site in a target RNA transcript, the method comprising:

a) incubating a cell with an affinity label to facilitate incorporation of the affinity label into nascent RNA;

b) capturing the affinity labeled nascent RNA with a solid support comprising specificity for the affinity label;

c) isolating the affinity labeled nascent RNA;

d) enriching the target RNA transcript from the isolated affinity labeled nascent RNA;

e) sequencing the enriched isolated affinity labeled nascent RNA; and f) identifying nascent RNA transcript intermediates, thereby identifying non-productive splice sites in the target RNA transcript.

In an embodiment, step a) comprises incubating cells for less than about 30 minutes in media containing the affinity label. In an embodiment, the affinity label comprises 4-thiouridine, 6-thio-guanosine, 5-ethynyl-uridine, or bromodeoxyuridine. In an embodiment, the 4-thiouridine labeled nascent RNA is biotinylated to produce biotinylated nascent RNA. In an embodiment, the biotinylated nascent RNA is captured in step b) with a streptavidin linked solid support. In an embodiment, the bromodeoxyuridine labeled nascent RNA is captured in step b) with an anti-bromodeoxyuridine antibody.

In an embodiment of the second aspect of the disclosure, the target enrichment in step d) comprises a pulldown step using nucleic acid probes complementary to the target RNA transcript. In an embodiment of the second aspect of the disclosure, the target enrichment in step d) comprises a pulldown step using nucleic acid primers complementary to the target RNA transcript for selective reverse transcription.

In an embodiment, the cell expresses the target RNA transcript.

In an embodiment of the first aspect of the disclosure, the target RNA transcript exon-exon junctions are annotated target RNA transcript exon-exon junctions or unannotated target RNA transcript exon-exon junctions.

In an embodiment of the second aspect of the disclosure, the method further comprises:

g) identifying split reads that do not map to target RNA transcript exon-exon junctions; and h) calculating the probability that the split reads represent non-productive transcripts.

In an embodiment, the target RNA transcript exon-exon junctions are annotated target RNA transcript exon-exon junctions or unannotated target RNA transcript exon-exon junctions.

In an embodiment of the second aspect of the disclosure, the method further comprises:

g) identifying split reads that do not map to annotated target RNA transcript exon-exon junctions; and h) calculating the probability that the split reads represent non-productive transcripts.

In an embodiment, the non-productive transcripts are rapidly degraded.

In an embodiment, the non-productive transcripts are not translated into a functional protein.

In an embodiment, the target RNA transcript comprises ADAR, ARSA, ATP1A2, CACNA1A, DNMT1, EIF2B1, EIF2B2, EIF2B5, IDUA, MFSD8, NF2, NPCl, PEX1, PRICKLE2, PRRT2, RAI1, SETD5, SHANK3, SLC6A1, STXBP1, STX1B, and TCF4.

In an embodiment, the target RNA transcript comprises CHD7, CTNNB1, EHMT1, GRN, HTR7, JAK2, KCNQ4, LEPR, LIPC, MBD5, MNX1, NFIA, NMU, NOTCH1, NSD1, PAX6, PHIP, PKD1, PYY, RAI1, RBPJ, RPS14, RUNX2, SETBP1, SETD5, SHANK3, SYNGAP1, TBX1, TCF4, TGIF1, and WDTC1.

In an embodiment, the target RNA transcript comprises ADAR, ARSA, ATP1A2, CACNA1A, CHD7, CTNNB1, DNMT1, EHMT1, EIF2B1, EIF2B2, EIF2B5, GRN, HTR7, IDUA, JAK2, KCNQ4, LEPR, LIPC, MBD5, MFSD8, MNX1, NF2, NFIA, NMU, NOTCH1, NPCl, NSD1, PAX6, PEX1, PHIP, PKD1, PRICKLE2, PRRT2, PYY, RAI1, RBPJ, RPS14, RUNX2, SETBP1, SETD5, SHANK3, SLC6A1, STXBP1, STX1B, SYNGAP1, TBX1, TCF4, TGIF1, and WDTC1.

In another aspect, the disclosure provides a method of identifying a non-productive splice site in a target RNA transcript, the method comprising: a) incubating a cell with an affinity label to facilitate incorporation of the affinity label into newly generated total RNA; b) capturing the affinity labeled total RNA with a solid support comprising specificity for the affinity label; c) separating the affinity labeled total RNA; d) binding nascent RNA transcript intermediates among the total RNA with one or more affinity labeled probes complementary to the nascent RNA transcript intermediates; e) capturing the nascent RNA transcript intermediates bound to the one or more affinity labeled probes with a solid support comprising specificity for the affinity label; f) isolating the captured nascent RNA transcript intermediates; and g) sequencing the isolated nascent RNA transcript intermediates, thereby identifying non-productive splice sites in the target RNA transcript.

In an embodiment, step a) comprises incubating cells for less than about 30 minutes in media containing the affinity label.

In an embodiment, the affinity label comprises 4-thiouridine, 6-thio-guanosine, 5-ethynyl-uridine, or bromodeoxyuridine. In an embodiment, the 4-thiouridine labeled total RNA is biotinylated to produce biotinylated total RNA.

In an embodiment, the biotinylated total RNA is captured in step b) with a streptavidin linked solid support.

In an embodiment, the bromodeoxyuridine labeled total RNA is captured in step b) with an anti-bromodeoxyuridine antibody.

In one aspect, the disclosure provides a method of identifying a non-productive splice site in a target RNA transcript, the method comprising the steps of: a) incubating a cell with 4-thiouridine to facilitate incorporation of 4-thiouridine into newly generated total RNA; b) biotinylating the 4-thiouridine in the total RNA; c) capturing the biotinylated total RNA with a streptavidin linked solid support; d) separating the biotinylated total RNA; e) binding nascent RNA transcript intermediates among the total RNA with one or more biotinylated probes complementary to the nascent RNA transcript intermediates; e) capturing the nascent RNA transcript intermediates bound to the one or more biotinylated probes with a streptavidin linked solid support; f) isolating the captured nascent RNA transcript intermediates; and g) sequencing the isolated nascent RNA transcript intermediates, thereby identifying non-productive splice sites in the target RNA transcript.

In an embodiment, step a) comprises incubating cells for less than about 30 minutes in media containing 4-thiouridine.

In an embodiment, the cell expresses the target RNA transcript.

In an embodiment, the method further comprises: h) identifying split reads that do not map to annotated target RNA transcript exon-exon junctions; and i) calculating the probability that the split reads represent non-productive transcripts.

In an embodiment, the non-productive transcripts are rapidly degraded. In an embodiment, the non-productive transcripts are not translated into a functional protein.

In one aspect, the disclosure provides a method of identifying a non-productive splice site in an SLC6A1 RNA transcript, the method comprising: a) incubating a cell with an affinity label to facilitate incorporation of the affinity label into newly generated total RNA; b) capturing the affinity labeled total RNA with a solid support comprising specificity for the affinity label; c) separating the affinity labeled total RNA; d) binding nascent SLC6A1 RNA transcript intermediates among the total RNA with one or more affinity labeled probes complementary to the nascent SLC6A1 RNA transcript intermediates; e) capturing the nascent SLC6A1 RNA transcript intermediates bound to the one or more affinity labeled probes with a solid support comprising specificity for the affinity label; f) isolating the captured nascent SLC6A1 RNA transcript intermediates; and g) sequencing the isolated nascent SLC6A1 RNA transcript intermediates, thereby identifying non-productive splice sites in the target RNA transcript.

In an embodiment, step a) comprises incubating cells for less than about 30 minutes in media containing the affinity label.

In an embodiment, the affinity label comprises 4-thiouridine or bromodeoxyuridine. In an embodiment, the 4-thiouridine labeled total RNA is biotinylated to produce biotinylated total RNA.

In an embodiment, the biotinylated total RNA is captured in step b) with a streptavidin linked solid support.

In an embodiment, the bromodeoxyuridine labeled total RNA is captured in step b) with an anti-bromodeoxyuridine antibody.

In an embodiment, step a) comprises incubating cells for less than about 30 minutes in media containing 4-thiouridine.

In an embodiment, the cell expresses the SLC6A1 RNA transcript. In an embodiment, the cell comprises a neuronal cell and/or an astrocyte.

In an embodiment, the method further comprises: h) identifying split reads that do not map to annotated target RNA transcript exon-exon junctions; and i) calculating the probability that the split reads represent non-productive SLC6A1 RNA transcripts.

In an embodiment, the non-productive SLC6A1 RNA transcripts are rapidly degraded. In an embodiment, the non-productive SLC6A1 RNA transcripts are not translated into a functional protein.

In an embodiment, the one or more affinity labeled probes complementary to SLC6A1 RNA matches about ≤70% to a second location in the genome, and wherein the one or more affinity labeled probes are located within SLC6A1 exons that are included within at least 50% of annotated SLC6A1 mRNA isoforms.

In an embodiment, the target RNA transcript comprises ATP1A2, CACNA1A, SETD5, SHANK3, NF2, DNMT1, TCF4, RAI1, PEX1, ARSA, EIF2B5, EIF2B1, EIF2B2, NPCl, ADAR, STXBP1, PRICKLE2, PRRT2, MFSD8, IDUA, SLC6A1, or STX1B. In an embodiment, the target RNA transcript comprises SLC6A1.

In an embodiment, the target RNA transcript is expressed from a gene that is related to a disease of haploinsufficiency.

In an embodiment, the target RNA transcript is associated with a disease or disorder. In an embodiment, the disease or disorder comprises a disease or disorder of the CNS. In an embodiment, the disease of the CNS comprises myoclonic-atonic epilepsy (MAE), epilepsy, attention deficit hyperactivity disorder (ADHD), familial hemiplegic migraine-2, familial basilar migraine, alternating hemiplegia of childhood, episodic ataxia type 2, familial hemiplegic migraine, Spinocerebellar ataxia type 6, mental retardation-23, 3p25 microdeletion syndrome, Phelan-McDermid syndrome, schizophrenia-15, Neurofibromatosis (type 1 or type 2, Meningioma, NF2-related, schwannomatosis 1, Hereditary sensory neuropathy type IE, autosomal dominant cerebellar ataxia, deafness, and narcolepsy, Pitt-Hopkins syndrome, Smith-Magenis syndrome, peroxisome biogenesis disorder 1a, Heimler syndrome-1, metachromatic leukodystrophy, leukoencephalopathy with vanishing white matter, Niemann-Pick disease type CI and Niemann-Pick disease type D, Aicardi-Goutieres syndrome-6, early infantile epileptic encephalopathy-4, progressive myoclonic epilepsy 5, familial infantile convulsion with paroxysmal choreoathetosis, episodic kinesigenic dyskinesia 1, benign familial infantile seizures-2, or generalized Epilepsy with febrile seizures plus type 9.

In one aspect, the disclosure provides an antisense oligonucleotide that binds to a target region in an RNA transcript associated with a disease of haploinsufficiency, wherein the target region comprises a splice modulatory element.

In an embodiment, the RNA transcript associated with a disease of haploinsufficiency is selected from the group consisting ADAR, ARSA, ATP1A2, CACNA1A, CHD7, CTNNB1, DNMT1, EHMT1, EIF2B1, EIF2B2, EIF2B5, GRN, HTR7, IDUA, JAK2, KCNQ4, LEPR, LIPC, MBD5, MFSD8, MNX1, NF2, NFIA, NMU, NOTCH1, NPCl, NSD1, PAX6, PEX1, PHIP, PKD1, PRICKLE2, PRRT2, PYY, RAI1, RBPJ, RPS14, RUNX2, SETBP1, SETD5, SHANK3, SLC6A1, STXBP1, STX1B, SYNGAP1, TBX1, TCF4, TGIF1, and WDTC1.

In an embodiment, the RNA transcript associated with a disease of haploinsufficiency is selected from the group consisting CHD7, CTNNB1, EHMT1, GRN, HTR7, JAK2, KCNQ4, LEPR, LIPC, MBD5, MNX1, NFIA, NMU, NOTCH1, NSD1, PAX6, PHIP, PKD1, PYY, RAI1, RBPJ, RPS14, RUNX2, SETBP1, SETD5, SHANK3, SYNGAP1, TBX1, TCF4, TGIF1, and WDTC1.

In an embodiment, the RNA transcript associated with a disease of haploinsufficiency is selected from the group consisting of ADAR, ARSA, ATP1A2, CACNA1A, DNMT1, EIF2B1, EIF2B2, EIF2B5, IDUA, MFSD8, NF2, NPCl, PEX1, PRICKLE2, PRRT2, RAI1, SETD5, SHANK3, SLC6A1, STXBP1, STX1B, and TCF4.

In an embodiment, binding of the antisense oligonucleotide to the target region increases the expression of a functional protein encoded by the RNA transcript in a cell.

In an embodiment, the splice modulatory element comprises one or more of a non-productive splice site, a exonic splicing enhancer, an exonic splicing silencer, an intronic splicing enhancer, or an intronic splicing silencer.

In an embodiment, the antisense oligonucleotide comprises a region of complementarity to a target region of an RNA transcript corresponding to any one of the genomic sequences recited in Table 4.

In an embodiment, the antisense oligonucleotide comprises a region of complementarity to a target region of an RNA transcript corresponding to any one of the genomic sequences of any one of SEQ ID NOs: 128-300.

In an embodiment, the antisense oligonucleotide comprises a region of complementarity to a target region of an RNA transcript corresponding to the genomic sequence of SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300.

In an embodiment, the antisense oligonucleotide comprises a region of complementarity to the reverse complement of any one of the genomic sequences recited in Table 4.

In an embodiment, the antisense oligonucleotide comprises a region of complementarity to the reverse complement of any one of the genomic sequences of any one of SEQ ID NOs: 128-300.

In an embodiment, the antisense oligonucleotide comprises a region of complementarity to the reverse complement the genomic sequence of SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300.

In an embodiment, the antisense oligonucleotide comprises 8 to 80 nucleotides in length. In an embodiment, the antisense oligonucleotide comprises 15 to 25 nucleotides in length. In an embodiment, the antisense oligonucleotide comprises 15 nucleotides in length. In an embodiment, the antisense oligonucleotide comprises 16 nucleotides in length. In an embodiment, the antisense oligonucleotide comprises 17 nucleotides in length. In an embodiment, the antisense oligonucleotide comprises 18 nucleotides in length. In an embodiment, the antisense oligonucleotide comprises 19 nucleotides in length. In an embodiment, the antisense oligonucleotide comprises 20 nucleotides in length. In an embodiment, the antisense oligonucleotide comprises 21 nucleotides in length. In an embodiment, the antisense oligonucleotide comprises 22 nucleotides in length. In an embodiment, the antisense oligonucleotide comprises 23 nucleotides in length. In an embodiment, the antisense oligonucleotide comprises 24 nucleotides in length. In an embodiment, the antisense oligonucleotide comprises 25 nucleotides in length. In an embodiment, the antisense oligonucleotide comprises 18 to 20 nucleotides in length.

In an embodiment, the antisense oligonucleotide comprises one or more modified nucleotides.

In an embodiment, the one or more modified nucleotides comprise a modification of a ribose group, a phosphate group, a nucleobase, or a combination thereof.

In an embodiment, the modification of the ribose group comprises 2'-O-methyl, 2'-fluoro, 2'-deoxy, 2'-O-(2-methoxyethyl) (MOE), 2'-O-alkyl, 2'-O-alkoxy, 2'-O-alkylamino, $2'-NH_2$, a constrained nucleotide, or a combination thereof. In an embodiment, the constrained nucleotide comprises a locked nucleic acid (LNA), an ethyl-constrained nucleotide, a 2'-(S)-constrained ethyl (S-cEt) nucleotide, a constrained MOE, a 2'-O,4'-C-aminomethylene bridged nucleic acid ($2',4'-BNA^{NC}$), an alpha-L-locked nucleic acid, a tricyclo-DNA, or a combination thereof.

In an embodiment, the modification of the ribose group comprises 2'-O-(2-methoxyethyl) (MOE).

In an embodiment, the modification of the phosphate group comprises a phosphorothioate, a phosphonoacetate (PACE), a thiophosphonoacetate (thioPACE), an amide, a triazole, a phosphonate, a phosphotriester modification, or a combination thereof.

In an embodiment, the modification of the phosphate group comprises phosphorothioate.

In an embodiment, the modification of the nucleobase group comprises 2-thiouridine, 4-thiouridine, $N^6$-methyladenosine, pseudouridine, 2,6-diaminopurine, inosine, thymidine, 5-methylcytosine, 5-substituted pyrimidine, isoguanine, isocytosine, halogenated aromatic groups, or a combination thereof.

In an embodiment, the modification of the nucleobase group comprises 5-methylcytosine.

In an embodiment, the antisense oligonucleotide further comprises a ligand.

In an embodiment, the antisense oligonucleotide comprises a sequence modification pattern of XsXsXsXsXsXsXsXsXsXsXsXsXsXsXsXsXsXs, XsXsXsXsXsXsXsXsXsXsXsXsXsXsXsXsXsXsXs,
or XsXsXsXsXsXsXsXsXsXsXsXsXsXsXsXsXsXsXsXs, wherein: s represents a phosphorothioate internucleoside linkage; and X represents an adenosine, a guanosine, a cytidine, or a thymine comprising a 2'-O-(2-methoxyethyl) modification.

In one aspect, the disclosure provides a method of treating a disease or disorder characterized by haploinsufficiency of a target gene, comprising administering to a subject in need thereof the antisense oligonucleotide recited above, and treating the disease or disorder.

In one aspect, the disclosure provides a method of increasing expression of a target functional RNA transcript in a cell, the method comprising contacting the cell with the antisense oligonucleotide recited above, thereby increasing the expression of the functional RNA transcript in a cell.

In an embodiment, expression is increased by about 20%, about 30%, about 40%, about 50%, about 60%, about 70%, about 80%, about 90%, about 100%, or more, relative to a cell that is not contacted with the antisense oligonucleotide.

In one aspect, the disclosure provides a method of increasing expression of a protein encoded by a RNA transcript associated with a disease of haploinsufficiency in a cell, the method comprising contacting a cell with the antisense oligonucleotide recited above, thereby increasing expression of the protein.

In an embodiment, expression is increased by about 20%, about 30%, about 40%, about 50%, about 60%, about 70%, about 80%, about 90%, about 100%, or more, relative to a cell that is not contacted with the antisense oligonucleotide.

In one aspect, the disclosure provides an antisense oligonucleotide comprising a region of complementarity to a target region of an RNA transcript corresponding to any one of the genomic sequences recited in Table 4, wherein the antisense oligonucleotide inhibits cryptic splicing at the target region and activates gene expression.

In one aspect, the disclosure provides an antisense oligonucleotide comprising a region of complementarity to a target region of an RNA transcript corresponding to any one of the genomic sequences of any one of SEQ ID NOs: 128-300, wherein the antisense oligonucleotide inhibits cryptic splicing at the target region and activates gene expression.

In one aspect, the disclosure provides an antisense oligonucleotide comprising a region of complementarity to a target region of an RNA transcript corresponding to the genomic sequence of SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300, wherein the antisense oligonucleotide inhibits cryptic splicing at the target region and activates gene expression.

BRIEF DESCRIPTION OF THE DRAWINGS

The features and advantages of the present invention will be more fully understood from the following detailed description of illustrative embodiments taken in conjunction with the accompanying drawings.

DETAILED DESCRIPTION

Figure 1:
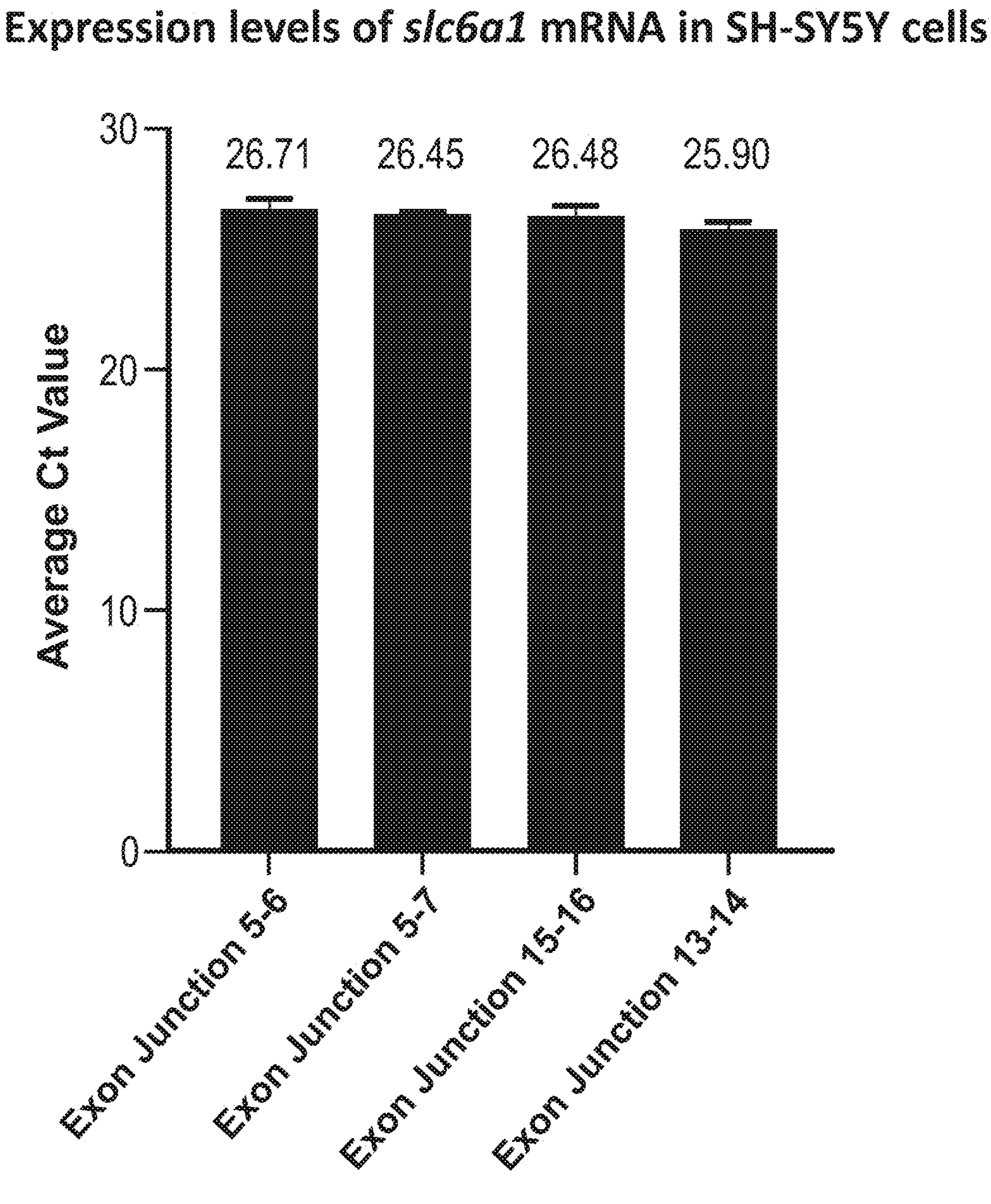
FIG. 1 depicts qPCR-based expression of SLC6A1 in human SH-SY5Y cells.

The present disclosure provides methods of identifying non-productive RNA transcript intermediates.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclatures used in connection with cell and tissue culture, molecular biology, immunology, microbiology, genetics and protein and nucleic acid chemistry and hybridization described herein are those well-known and commonly used in the art. The nomenclatures used in connection with, and the laboratory procedures and techniques of, analytical chemistry, synthetic organic chemistry, and medicinal and pharmaceutical chemistry described herein are those well-known and commonly used in the art.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). An RNA nucleotide refers to a single ribonucleotide. The term "DNA" or "DNA molecule" or "deoxyribonucleic acid molecule" refers to a polymer of deoxyribonucleotides. A DNA nucleotide refers to a single deoxyribonucleotide. As used herein, the term "DNA-like" refers to a conformation of, e.g. a modified nucleoside or nucleotide which is similar to the conformation of a corresponding unmodified DNA unit. For example, a DNA-like nucleotide may refer to a conformation of a modified deoxyribonucleotide similar to a corresponding unmodified deoxyribonucleotide. Examples of DNA-like nucleotides include, without limitation, e.g., 2'-deoxyribonucleotides, 2'-deoxy-2'-substituted arabinonucleotides (e.g., 2'-deoxy-2'-fluoroarabinonucleotides, also known in the art as 2'F-ANA or FANA), and corresponding phosphorothioate analogs. As used herein, the term "RNA-like" refers to a conformation of, e.g. a modified nucleoside or nucleotide which is similar to the conformation of a corresponding unmodified RNA unit. RNA-like conformations may adopt an A-form helix while DNA-like conformations adopt a B-form helix. Examples RNA-like nucleotides include, without limitation, e.g., 2'-substituted-RNA nucleotides (e.g., 2'-fluoro-RNA nucleotides also known in the art as 2'F-RNA), locked nucleic acid (LNA) nucleotides (also known in the art as bridged nucleic acids or bicyclic nucleotides), 2'-fluoro-4'-thioarabinonucleotide (also known in the art as 4'S-FANA nucleotides), 2'-O-alkyl-RNA, and corresponding phosphorothioate analogs.

DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. In certain embodiments, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary modified nucleotides are modified at any position so as to alter certain chemical properties of the nucleotide yet retain the ability of the modified nucleotide to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Modified nucleotides also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotides such as those described in Herdewijn, Antisense Nucleic Acid Drug Dev., 2000 Aug. 10(4):297-310.

Modified nucleotides may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. For another example, the ribose sugar may be replaced with a bicyclic or tricylic moiety, such as in Locked Nucleic Acid, constrained ethyl, tricycloDNA, or other bridged or bicyclic modifications. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

As used herein, the terms "unmodified nucleotide" or "non-modified nucleotide" refers to a nucleotide composed of naturally occurring nucleobases, sugar moieties, and internucleoside linkages. In some embodiments, a non-modified nucleotide is an RNA nucleotide (i.e. β-D-ribonucleoside) or a DNA nucleotide (i.e. β-D-deoxyribonucleoside).

The term "oligonucleotide" refers to a short polymer of nucleotides and/or modified nucleotides. As discussed above, the oligonucleotides may be linked with linkages which result in a lower rate of hydrolysis as compared to an oligonucleotide linked with phosphodiester linkages. For example, the nucleotides of the oligonucleotide may comprise triazole, amide, carbamate, methylenediol, ethylene diol, oxymethylthio, oxyethylthio, oxycarbonyloxy, phosphorodiamidate, phosphoroamidate, phosphonate, and/or phosphorothioate linkages. Alterations or modifications of the oligonucleotide can further include addition of non-nucleotide material, such as to the end(s) of the oligonucleotide or internally (at one or more nucleotides of the oligonucleotide).

The term "antisense" refers generally to any approach reliant upon agents, e.g., single-stranded oligonucleotides, that are sufficiently complementary to a target sequence to associate with the target sequence in a sequence-specific manner (e.g., hybridize to the target sequence). Exemplary uses of antisense in the instant application involve use of an oligoribonucleotide agent that hybridizes to a target pre-mRNA molecule and blocks an activity/effect (e.g., splicing pattern and/or blocking of non-productive splice sites) of the targeted pre-mRNA sequence, but antisense approaches commonly are used to target DNA or RNA for transcriptional inhibition, translational inhibition, degradation, etc. Antisense is a technology that can be initiated by the hand of man, for example, to modulate splicing and/or silence the expression of target genes.

As used herein, the term "antisense oligonucleotide" refers to a nucleic acid (e.g., an RNA or analog thereof), having sufficient sequence complementarity to a target RNA (i.e., the RNA for which splice site selection is modulated) to block a region of a target RNA (e.g., pre-mRNA) in an effective manner. In exemplary embodiments of the instant invention, such blocking of non-productive splice sites in SLC6A1 pre-mRNA serves to modulate splicing, either by masking a binding site for a native protein that would otherwise modulate splicing and/or by altering the structure of the targeted RNA. In certain embodiments of the instant invention, the target RNA is a target pre-mRNA (e.g., SLC6A1 pre-mRNA).

An antisense oligonucleotide having a "sequence sufficiently complementary to a target RNA sequence to modulate splicing of the target RNA" means that the antisense agent has a sequence sufficient to trigger the masking of a binding site for a native protein that would otherwise modulate splicing and/or alters the three-dimensional structure of the targeted RNA. Likewise, an oligonucleotide reagent having a "sequence sufficiently complementary to a target RNA sequence to modulate splicing of the target RNA" means that the oligonucleotide reagent has a sequence sufficient to trigger the masking of a binding site for a native protein that would otherwise modulate splicing and/or alters the three-dimensional structure of the targeted RNAs used herein.

As used herein, the term "intron" is a segment of DNA that is transcribed but removed from an RNA transcript by being spliced together with a sequence (exon) on either side of it. Introns are considered to be intervening sequences within the protein coding region of a gene and generally do not contain information represented in the protein produced from the gene. The term "exon" encompasses any segment of a gene that contains intervening sequences represented in the mature RNA product. An exon comprises information within a gene that is translated into a protein.

The term "nascent RNA intermediate" or "primary transcript RNA" refers to a newly synthesized RNA molecule that has not yet fully undergone posttranscriptional processing. It encompasses the first RNA product resulting from transcription of a gene by RNA polymerase. The RNA, termed nascent RNA, contains both intron and exon sequences and is therefore not processed by the cellular splicing machinery or only partially processed by the cellular machinery. The nascent RNA includes, but is not limited to, non-productively spliced RNA.

The term "posttranscriptional processing," as used herein, refers to the modifications made to nascent RNA molecules (or pre-mRNAs) before the nascent RNA molecules exit the nucleus of a cell. Such modifications include, for example, capping of the 5' end of nascent RNA (typically with a 7-methylguanosine linked to the first nucleotide via a 5'-5' triphosphate bridge), polyadenylation of the 3'end of the nascent RNA, or removal of introns via splicing.

The term "splicing" encompasses cellular events that occur in the nuclei of eukaryotic cells where introns are removed from the pre-mRNA species. In general, the process requires the formation of a spliceosome complex in which a 5' splice donor site is brought into proximity with a 3' splice acceptor site and an intervening intron sequence is removed from the transcript.

The term "noisy splicing", "cryptic splicing", or "non-productive splicing" refers to the event when the spliceosome utilizes erroneous splice sites and generates RNA transcripts that then undergo nonsense-mediated RNA decay. In cryptic or nonproductive splicing, spliceosome components, comprising enzymes that are involved in the RNA splicing process, can often bind to cryptic sites (with either canonical or non-canonical sequence elements) and improperly splice an RNA molecule. In the instance of an RNA transcript that contains at least one inefficiently spliced intron, i.e. the result of noisy or non-productive splicing, the RNA may be maintained in the nucleus, and if it is exported to the cytoplasm it is not translated into protein but is degraded. The phenomenon of nonproductive splicing is particularly common in genes with long introns or many introns.

As used herein, the term "increasing protein production" or "increasing expression of a target protein" means enhancing the amount of protein (e.g., a target protein) that is translated from an RNA molecule in a cell. A "target protein" may be any protein for which increased expression/production is desired. In some embodiments, the target protein is a disease-associated protein, such a GABA transporter protein encoded by SLC6A1. For example, contacting a cell with an antisense oligonucleotide that is complementary to a region in the nascent RNA molecular that contains a non-productive splicing site would results in a measurable increase in the amount of the protein (e.g., a target protein) encoded by the RNA. Methods of measuring or detecting production of a protein include, for example, Western blotting, flow cytometry, immunofluorescence microscopy, and ELISA.

As used herein, the term "metabolic labelling" refers to the incorporation of a biomolecule into a macromolecule. Metabolic labeling can be accomplished by contacting cells in medium that is supplemented with a metabolic label. For example, a metabolic label can be a label that is incorporated into newly synthesized RNA molecules, or nascent RNA. In one embodiment, the metabolic label is 4-thiouridine (4sU), which is a thiol-containing nucleoside that can be introduced into nucleoside salvage pathways in eukaryotic cells and allow non-disruptive labeling of newly transcribed RNA. Other examples of metabolic labels 6-thio-guanosine (6sG), 5-ethynyl-uridine (5eU), or bromodeoxyuridine (BdU). 4sU and 6sG can be biotinylated, 5eU can be modified by click chemistry, and BdU can be associated with antibodies for the purpose of capture/isolation of the RNA.

As used herein, the term "affinity label" refers to a group, moiety, or entity that specifically interacts/associates with a counterpart entity (e.g., capture agent). The affinity label/capture agent pair is often referred to as an "affinity pair". The affinity pair can be a biochemical pair. Examples of biochemical pairs include antibody-antigen, enzyme-inhibitor, biotin-streptavidin, hormone-receptor, sugar-lectin and complementary nucleic acid components. The biochemical interaction between members of the affinity pair can be non-covalent or covalent in nature. Examples of non-covalent interactions are those that involve hydrophobic, hydrophilic, or Van der Waals interactions between members of an affinity pair. Examples of covalent interactions involve the formation of a peptide bond or a disulfide bond between members of an affinity pair. In an exemplary embodiment, the members of the affinity pair are 4sU and EZ-Link™ Biotin-HPDP. Biotin-HPDP (N-[6-(biotinamido)hexyl]-3'-(2'-pyridyldithio)propionamide), is a sulfhydryl-reactive biotinylation agent. The pyridyl disulfide group at the end of biotin-HPDP reacts with free thiol groups on proteins and other molecules such as 4sU in 4sU-labeled RNA. The interaction between biotin-HPDP and 4sU leads to the formation of a covalent disulfide bond. The long spacer arm of biotin-HPDP enables the biotin part in biotin-HPDP to undergo further pairing with avidin or streptavidin. The covalent disulfide bond between 4sU and biotin-HPDP can be broken by the addition of reducing agents, such as dithiothreitol (DTT), or beta-mercapto ethanol. The term "target gene" or "target RNA transcript" is a gene or transcript (e.g., a pre-mRNA) whose expression is to be substantially modulated. This modulation can be achieved by steric blocking of a non-productive or cryptic splice site.

The term "non-target gene" is a gene whose expression is not to be substantially modulated. For example, a target gene of the present invention is SLC6A1, and a non-target gene of the present invention is a gene that is not SLC6A1. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g., an orthologue or paralogue) of the target gene.

The term "antisense activity" means any detectable or measurable activity attributable to the hybridization of an antisense compound to its target nucleic acid. In some embodiments, antisense activity is an increase in the amount or expression of a target nucleic acid or protein encoded by such target nucleic acid.

The term "target-recognition sequence" refers to the portion of an antisense compound that recognizes a target nucleic acid. The target-recognition sequence has a nucleobase sequence that permits hybridization to a corresponding region or segment of a target nucleic acid.

The term "conserved region" refers to a portion, or portions, of a nucleic acid sequence that is conserved, i.e. a portion, or portions of the nucleic acid sequence having a similar or identical sequence across species. A conserved region may be computationally identified, e.g., using any sequence alignment software available in the art.

As used herein, the term "sufficiently complementary" means that antisense oligonucleotide has a sequence (e.g., an antisense oligonucleotide having a target-recognition sequence) which is sufficient to bind the desired target transcript (e.g., a SLC6A1 transcript), and to trigger the inhibition of non-productive splicing of the target transcript (e.g., steric inhibition of splicing machinery of the target pre-mRNA). For example, a target-recognition sequence with at least 90% complementarity to a target nucleic acid sequence (e.g., a portion of a SLC6A1 transcript) may be sufficiently complementary to trigger modulation of the SLC6A1 transcript. The term "perfectly complementary" refers to, e.g., a target-recognition sequence with 100% complementarity to a target nucleic acid sequence. Complementary nucleic acid molecules hybridize to each other. The term "hybridization" means the annealing of complementary nucleic acid molecules. In certain embodiments, complementary nucleic acid molecules include an antisense compound and a target nucleic acid.

The term "about" or "approximately" means within 20%, such as within 10%, within 5%, or within 1% or less of a given value or range.

As used herein, "administer" or "administration" refers to the act of injecting or otherwise physically delivering a substance as it exists outside the body (e.g., an antisense compound provided herein) into a patient. The antisense oligonucleotides described herein may be administered to the central nervous system of a patient. The central nervous system includes the brain and spinal cord. Administration methods to the central nervous system include, but not limited to, intrathecal, intraventricular or intrastriatal infusion or delivery and/or any other method of physical delivery described herein or known in the art. Intraventricular infusion may comprise administration using an Ommaya reservoir.

When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms, e.g., damage to the involved tissues and airways.

As used herein, the term "composition" is intended to encompass a product containing the specified ingredients (e.g., an antisense compound provided herein) in, optionally, the specified amounts.

"Effective amount" means the amount of active pharmaceutical agent (e.g., an antisense compound of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject can be a mammal, such as a non-primate (e.g., cows, pigs, horses, cats, dogs, rats, etc.) or a primate (e.g., monkey and human). In certain embodiments, the term "subject," refers to a vertebrate, such as a mammal. Mammals include, without limitation, humans, non-human primates, wild animals, feral animals, farm animals, sports animals, and pets. In one embodiment, the subject is a mammal, such as a human, having a disease of haploinsufficiency (e.g., myoclonic-atonic epilepsy (MAE)). In another embodiment, the subject is a mammal, such as a human, that is at risk for developing a disease of haploinsufficiency.

As used herein, the term "therapy" refers to any protocol, method and/or agent that can be used in the prevention, management, treatment and/or amelioration of a disease or a symptom related thereto, such as a disease of haploinsufficiency (e.g., myoclonic-atonic epilepsy (MAE)). In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, such as a disease of haploinsufficiency. In other embodiments, the terms "therapies" and "therapy" refer to a biological therapy, supportive therapy, and/or other therapies useful in the modulation of an immune response to an infection in a subject or a symptom related thereto.

As used herein, the terms "treat," "treatment" and "treating" refer to the reduction or amelioration of the progression, severity, and/or duration of a disease or a symptom related thereto, such as a SLC6A1-related disorder, resulting from the administration of one or more therapies (including, but not limited to, the administration of one or more prophylactic or therapeutic agents, such as an antisense oligonucleotide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

As used herein, a "splice modulatory element" is a nucleic acid region in a target RNA transcript (e.g., a SLC6A1 transcript), which either enhances or silences the splicing of introns in the pre-mRNA, or in general regulates the constitutive or alternative splicing of the pre-mRNA. Examples of splice modulatory elements include, but are not limited to, non-productive splice sites, exonic splicing enhancers, exonic splicing silencers, intronic splicing enhancers, and intronic splicing silencers.

As used herein, a "non-productive splice site" or "cryptic splice site" is splice site in a pre-mRNA that is used by the cellular splicing machinery that leads to the inappropriate inclusion and/or exclusion of introns and/or exons, thereby producing a non-functional transcript. The non-functional transcript may be rapidly degraded in the cell via one or more mechanisms, such as nonsense-mediated decay (NMD). The non-functional transcript may be translated into a non-functional or deleterious protein.

As used herein, a "functional RNA transcript" is an RNA transcript that is translated into a functional protein encoded by said functional RNA transcript (e.g., functional SLC6A1 RNA transcript encoding the GABA Transporter 1, GAT-1, protein).

As used herein, "enriching" for or the "enrichment" of a target RNA transcript is a process of either isolating a target RNA transcript from a heterogeneous population of RNA transcripts, or amplifying the number of target RNA transcript molecules in a heterogeneous population of RNA transcripts. With respect to isolation, the target RNA transcript need not be completely purified away from the heterogeneous population of RNA transcripts. The purpose of enrichment is to enhance the sensitivity of a downstream sequencing step, improving the signal-to-noise ratio, to improve the identification of nascent RNA transcript intermediates, and thereby facilitating the identification of non-productive splice sites in the target RNA transcript.

An enrichment step may comprise a pulldown step, by using one or more nucleic acid probes that are complementary to the target RNA transcript. Alternatively, or in combination, an enrichment step may comprise using nucleic acid primers complementary to the target RNA transcript for selective reverse transcription (i.e., reverse transcribing the target RNA transcript to which the nucleic acid primers bind). The reverse transcribed DNA can be further amplified by PCR.

Non-Productive Splice Site Identification

The present disclosure provides methods of identifying non-productive splice sites in target RNA transcripts (e.g., a target pre-mRNA). Cryptic or non-productive splicing occurs when the spliceosome utilizes erroneous splice sites and generates transcripts that then undergo nonsense-mediated mRNA decay (NMD) or an alternative mechanism of rapid mRNA degradation. This can occur in genes with long introns or many introns. While these isoforms are rarely observed in steady-state gene expression measurements, they are likely to represent a large amount of the total transcriptional output of a gene. Without wishing to be bound by theory, blocking non-productive splice sites can lead to an increase in productive mRNA levels as there are fewer molecular resources being wasted on the generation of non-productive transcripts. Due to the rapid degradation of these non-productive mRNA (generated from the use of non-productive splice sites in pre-mRNA), it is challenging to detect and characterize non-productive mRNA.

In one aspect, the disclosure provides a method of identifying non-productive splice sites in a target RNA transcript, the method comprising:

a) incubating a cell with an affinity label to facilitate incorporation of the affinity label into newly generated total RNA;
b) capturing the affinity labeled total RNA with a solid support comprising specificity for the affinity label;
c) separating the affinity labeled total RNA;

d) binding nascent RNA transcript intermediates among the total RNA with one or more affinity labeled probes complementary to the nascent RNA transcript intermediates;
e) capturing the nascent RNA transcript intermediates bound to the one or more affinity labeled probes with a solid support comprising specificity for the affinity label;
f) isolating the captured nascent RNA transcript intermediates; and
g) sequencing the isolated nascent RNA transcript intermediates, thereby identifying non-productive splice sites in the target RNA transcript.

In certain embodiments, step a) comprises incubating cells for less than about 30 minutes in media containing the affinity label. In certain embodiments, step a) comprises incubating cells for about 30 seconds, about 1 minute, about 2 minutes, about 3 minutes, about 4 minutes, about 5 minutes, about 7.5 minutes, about 10 minutes, about 12.5 minutes, about 15 minutes, about 17.5 minutes, about 20 minutes, about 22.5 minutes, about 25 minutes, about 27.5 minutes, or about 30 minutes in media containing the affinity label. In certain embodiments, step a) comprises incubating cells in media containing the affinity label for a time sufficient to facilitate incorporation of the affinity label into newly generated total RNA. As used herein, a "time sufficient to facilitate incorporation of the affinity label into newly generated total RNA" is the amount of time that allows for sufficient incorporation of the affinity label into newly generated total RNA such that the affinity labeled total RNA may be captured in sufficient quantity to identified one or more non-productive splice sites in a target RNA transcript.

In certain embodiments, the affinity label comprises 4-thiouridine, 6-thio-guanosine, 5-ethynyl-uridine, or bromodeoxyuridine. In certain embodiments, the 4-thiouridine labeled total RNA is biotinylated to produce biotinylated total RNA. In certain embodiments, the biotinylated total RNA is captured in step b) with a streptavidin linked solid support. In certain embodiments, the bromodeoxyuridine labeled total RNA is captured in step b) with an anti-bromodeoxyuridine antibody.

In certain embodiments, the cell incubated with an affinity label expresses the target RNA transcript.

In certain embodiments, the method further comprises:
h) identifying split reads that do not map to annotated target RNA transcript exon-exon junctions; and
i) calculating the probability that the split reads represent non-productive transcripts.

In certain embodiments, the non-productive transcripts are rapidly degraded. In certain embodiments, the non-productive transcripts are not translated into a functional protein.

In one aspect, the disclosure provides a method of identifying non-productive splice sites in a target RNA transcript, the method comprising:
a) incubating a cell with 4-thiouridine to facilitate incorporation of 4-thiouridine into newly generated total RNA;
b) biotinylating the 4-thiouridine in the total RNA;
c) capturing the biotinylated total RNA with a streptavidin linked solid support;
d) separating the biotinylated total RNA;
e) binding nascent RNA transcript intermediates among the total RNA with one or more biotinylated probes complementary to the nascent RNA transcript intermediates;
e) capturing the nascent RNA transcript intermediates bound to the one or more biotinylated probes with a streptavidin linked solid support;
f) isolating the captured nascent RNA transcript intermediates; and
g) sequencing the isolated nascent RNA transcript intermediates, thereby identifying non-productive splice sites in the target RNA transcript.

In certain embodiments, the target RNA transcript comprises ATP1A2, CACNA1A, SETD5, SHANK3, NF2, DNMT1, TCF4, RAI1, PEX1, ARSA, EIF2B5, EIF2B1, EIF2B2, NPCl, ADAR, STXBP1, PRICKLE2, PRRT2, MFSD8, IDUA, SLC6A1, or STX1B. In certain embodiments, the target RNA transcript comprises SLC6A1. In certain embodiments, the target RNA transcript is expressed from a gene that is related to a disease of haploinsufficiency. In certain embodiments, the target RNA transcript is associated with a disease or disorder. In certain embodiments, the disease or disorder is a disease or disorder of the CNS. In certain embodiments, the disease of the CNS comprises myoclonic-atonic epilepsy (MAE), epilepsy, attention deficit hyperactivity disorder (ADHD), familial hemiplegic migraine-2, familial basilar migraine, alternating hemiplegia of childhood, episodic ataxia type 2, familial hemiplegic migraine, Spinocerebellar ataxia type 6, mental retardation-23, 3p25 microdeletion syndrome, Phelan-McDermid syndrome, schizophrenia-15, Neurofibromatosis (type 1 or type 2, Meningioma, NF2-related, schwannomatosis 1, Hereditary sensory neuropathy type IE, autosomal dominant cerebellar ataxia, deafness, and narcolepsy, Pitt-Hopkins syndrome, Smith-Magenis syndrome, peroxisome biogenesis disorder 1a, Heimler syndrome-1, metachromatic leukodystrophy, leukoencephalopathy with vanishing white matter, Niemann-Pick disease type CI and Niemann-Pick disease type D, Aicardi-Goutieres syndrome-6, early infantile epileptic encephalopathy-4, progressive myoclonic epilepsy 5, familial infantile convulsion with paroxysmal choreoathetosis, episodic kinesigenic dyskinesia 1, benign familial infantile seizures-2, or generalized Epilepsy with febrile seizures plus type 9.

In one aspect, the disclosure provides a method of identifying non-productive splice sites in an SLC6A1 RNA transcript, the method comprising:
a) incubating a cell with an affinity label to facilitate incorporation of the affinity label into newly generated total RNA;
b) capturing the affinity labeled total RNA with a solid support comprising specificity for the affinity label;
c) separating the affinity labeled total RNA;
d) binding nascent SLC6A1 RNA transcript intermediates among the total RNA with one or more affinity labeled probes complementary to the nascent SLC6A1 RNA transcript intermediates;
e) capturing the nascent SLC6A1 RNA transcript intermediates bound to the one or more affinity labeled probes with a solid support comprising specificity for the affinity label;
f) isolating the captured nascent SLC6A1 RNA transcript intermediates; and
g) sequencing the isolated nascent SLC6A1 RNA transcript intermediates, thereby identifying non-productive splice sites in the target RNA transcript.

In certain embodiments, the cell incubated with an affinity label expresses the SLC6A1 RNA transcript. In certain embodiments, the cell comprises a neuronal cell and/or an astrocyte.

In certain embodiments, the method further comprising:

h) identifying split reads that do not map to annotated target RNA transcript exon-exon junctions; and i) calculating the probability that the split reads represent non-productive SLC6A1 RNA transcripts. In certain embodiments, the non-productive SLC6A1 RNA transcripts are rapidly degraded. In certain embodiments, the non-productive SLC6A1 RNA transcripts are not translated into a functional protein.

In certain embodiments, one or more affinity labeled probes complementary to SLC6A1 RNA matches about ≤70% to a second location in the genome, and wherein the one or more affinity labeled probes are located within SLC6A1 exons that are included within at least 50% of annotated SLC6A1 mRNA isoforms.

Steric Blocking Antisense Oligonucleotides

The present disclosure provides antisense oligonucleotides that are capable of sterically blocking non-productive splice sites in target RNA transcripts (e.g., target pre-mRNA). The non-productive splice sites in target RNA transcripts are identified by the methods recited in the section above. Upon identification, antisense oligonucleotides may be designed that comprise a region of complementarity to a target region containing the non-productive splice site. In certain embodiments, the antisense oligonucleotides of the disclosure comprise a region of complementarity to a target region of any one of SEQ ID NOs: 1-108, as recited in Table 1 and Table 2.

In certain embodiments, the antisense oligonucleotides of the disclosure comprise at least one nucleotide that has complementarity to the non-productive splice site. The antisense oligonucleotides of the disclosure need not comprise complementarity to the non-productive splice site to reduce the level of non-productive target RNA splice forms or increase the generation of productive target mRNA isoforms. Rather, the antisense oligonucleotides of the disclosure may comprise complementarity to a region around the non-productive splice site. For example, but in no way limiting, the antisense oligonucleotides may comprise complementarity to a region upstream (5') of the non-productive splice site or a region downstream (3') of the non-productive splice site. The antisense oligonucleotides may comprise complementarity to a region 1, 2, 3, 4, 5, 10, 15, 20, 25, 30, 35, 40, 45, 50, 55, 60, 65, 70, 75, 80, 85, 90, 95, 100, or more nucleotides upstream of the non-productive splice site. The antisense oligonucleotides may comprise complementarity to a region about 1 to about 100 nucleotides upstream of the non-productive splice site. The antisense oligonucleotides may comprise complementarity to a region 1, 2, 3, 4, 5, 10, 15, 20, 25, 30, 35, 40, 45, 50, 55, 60, 65, 70, 75, 80, 85, 90, 95, 100, or more nucleotides downstream of the non-productive splice site. The antisense oligonucleotides may comprise complementarity to a region about 1 to about 100 nucleotides downstream of the non-productive splice site.

In certain embodiments, the antisense oligonucleotides of the disclosure may comprise complementarity to a exonic splicing enhancer, an exonic splicing silencer, an intronic splicing enhancer, or an intronic splicing silencer. The antisense oligonucleotides of the disclosure may possess a region of complementarity to a target exonic splicing enhancer, an exonic splicing silencer, an intronic splicing enhancer, or an intronic splicing silencer sufficient to reduce the level of non-productive target splice forms or increase the generation of productive target mRNA isoforms.

Sterically blocking non-productive splice sites in target transcripts may reduce the generation of non-productive splice forms of target transcripts. Non-productive splice forms of target transcripts may be target transcripts that are not translated into a functional protein encoded by the target transcript or target transcripts that are translated into non-functional proteins. In certain embodiments, the antisense oligonucleotides of the disclosure reduce the level of target non-productive splice forms by at least about 20%, about 25%, about 30%, about 35%, about 40%, about 45%, about 50%, about 55%, about 60%, about 65%, about 70%, about 75%, about 80%, about 85%, about 90%, about 95%, or about 100%. The % reduction may be in comparison to a non-specific control antisense oligonucleotide or in comparison to the levels of target non-productive splice forms prior to administration of an antisense oligonucleotide. In certain embodiments, sterically blocking non-productive splice sites in a target transcript may increase the generation of productive target mRNA isoforms. Productive target mRNA isoforms are mRNA that are translated into a functional protein encoded by the target transcript. In certain embodiments, the antisense oligonucleotides of the disclosure increase the level of productive target mRNA isoforms by at least about 20%, about 25%, about 30%, about 35%, about 40%, about 45%, about 50%, about 55%, about 60%, about 65%, about 70%, about 75%, about 80%, about 85%, about 90%, about 95%, or about 100%. The % increase may be in comparison to a non-specific control antisense oligonucleotide or in comparison to the levels of productive target mRNA isoforms forms prior to administration of an antisense oligonucleotide.

In certain embodiments, the antisense oligonucleotides of the disclosure possess complementarity to a target non-productive splice site in a target transcript, thereby sterically blocking the non-productive splice site. In certain embodiments, the antisense oligonucleotides of the disclosure possess complementarity to a target non-productive 5' splice site (5'ss). In certain embodiments, the antisense oligonucleotides of the disclosure possess complementarity to a target non-productive 3' splice site (3'ss). The antisense oligonucleotides of the disclosure possess a region of complementarity to a target non-productive 5'ss or 3'ss sufficient to reduce the level of target non-productive splice forms or increase the generation of productive target mRNA isoforms.

In certain embodiments, the antisense oligonucleotides that are capable of sterically blocking non-productive splice sites in target transcripts, have chemically modified subunits arranged in patterns, or motifs, to confer to the antisense compounds properties such as enhanced the inhibitory activity, increased binding affinity for a target nucleic acid, or resistance to degradation by in vivo nucleases.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a target nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of ring atoms to form bicyclic nucleic acids (BNA), replacement of the ribosyl ring oxygen atom with S, N(R), or $C(R^1)(R^2)$ (R═H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007) wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F (i.e., 2'-fluoro), 2'-$OCH_3$ (i.e., 2'-O-methyl) and 2'-$O(CH_2)_2OCH_3$ (i.e., 2'-O-methoxyethyl) substituent groups. The substituent at the 2' position can also be selected from allyl, amino, azido, thio, O-allyl, O—C1-C10 alkyl, $OCF_3$, $O(CH_2)_2SCH_3$, $O(CH_2)_2$—O—N$(R_m)(R_n)$, and O—$CH_2$—C(═O)—N$(R_m)(R_n)$, where each $R_m$ and $R_n$ is, independently, H or substituted or unsubstituted C1-C10 alkyl. 2'-modified nucleotides are useful in the present invention, for example, 2'-O-methyl RNA, 2'-0-methoxyethyl RNA, 2'-fluoro RNA, and others envisioned by one of ordinary skill in the art.

Examples of bicyclic nucleic acids (BNAs) include without limitation nucleosides comprising a bridge between the 4' and the 2' ribosyl ring atoms. A BNA comprising a bridge between the 4' and 2' ribosyl ring atoms can be referred to as a locked nucleic acid (LNA), and is often referred to as inaccessible RNA. As used herein, the term "locked nucleotide" or "locked nucleic acid (LNA)" comprises nucleotides in which the 2' deoxy ribose sugar moiety is modified by introduction of a structure containing a heteroatom bridging from the 2' to the 4' carbon atoms. The term "non-locked nucleotide" comprises nucleotides that do not contain a bridging structure in the ribose sugar moiety. Thus, the term comprises DNA and RNA nucleotide monomers (phosphorylated adenosine, guanosine, uridine, cytidine, deoxyadenosine, deoxyguanosine, deoxythymidine, deoxycytidine) and derivatives thereof as well as other nucleotides having a 2'-deoxy-erythro-pentofuranosyl sugar moiety or a ribopentofuranosyl moiety. In certain embodiments, antisense compounds provided herein include one or more BNA nucleosides wherein the bridge comprises one of the formulas: 4'-$(CH_2)$—O-2' (LNA); 4'-$(CH_2)$—S-2'; 4'-$(CH_2)$—O-2' (LNA); 4'-$(CH_2)_2$—O-2' (ENA); 4'-$C(CH_3)_2$—O-2' (see PCT/US2008/068922); 4'-$CH(CH_3)$—O-2' and 4'-CH$(CH_2OCH_3)$—O-2' (see U.S. Pat. No. 7,399,845, issued on Jul. 15, 2008); 4'-$CH_2$—N$(OCH_3)$-2' (see PCT/US2008/064591); 4'-$CH_2$—O—N$(CH_3)$-2' (see published U.S. Patent Application US2004-0171570, published Sep. 2, 2004); 4'-$CH_2$—N(R)—O-2' (see U.S. Pat. No. 7,427,672, issued on Sep. 23, 2008); 4'-$CH_2$—C$(CH_3)$-2' and 4'-$CH_2$—C(═$CH_2$)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In some embodiments, antisense compounds provided herein include one or more 2', 4'-constrained nucleotides. For example, antisense compounds provided by the present disclosure include those having one or more constrained ethyl (cEt) or constrained methoxyethyl (cMOE) nucleotides. In some embodiments, antisense compounds provided herein are antisense oligonucleotides comprising one or more constrained ethyl (cEt) nucleotides. The terms "constrained ethyl" and "ethyl-constrained" are used interchangeably.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

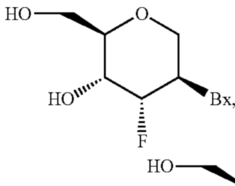
,
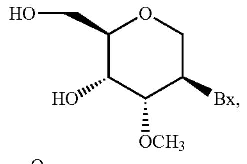
, or
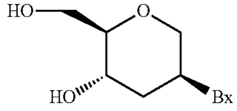

Many other bicyclo and tricyclo sugar surrogate ring systems are also known in the art that can be used to modify nucleosides for incorporation into antisense compounds (see for example review article: Leumann, J. C, *Bioorganic & Medicinal Chemistry,* 2002, 10, 841-854; Ito, K. R.; Obika, S., Recent Advances in Medicinal Chemistry of Antisense Oligonucleotides. In *Comprehensive Medicinal Chemistry,* 3rd edition, Elsevier: 2017). Such ring systems can undergo various additional substitutions to enhance activity.

Methods for the preparations of modified sugars are well known to those skilled in the art. In nucleotides having modified sugar moieties, the nucleobase moieties (natural, modified or a combination thereof) are maintained for hybridization with an appropriate nucleic acid target.

In certain embodiments, antisense compounds targeted to a target nucleic acid comprise one or more kinds of modified nucleotides. In one embodiment, antisense compounds targeted to a target nucleic acid comprise 2'-modified nucleotides. In one embodiment, antisense compounds targeted to a target nucleic acid comprise a 2'-O-methyl RNA, a 2'-O-methoxyethyl RNA, or a 2'-fluoro RNA. In one embodiment, antisense compounds targeted to a target nucleic acid comprise tricyclo-DNA. Tricyclo-DNA belongs to a class of constrained DNA analogs that display improved hybridizing capacities to complementary RNA, see, e.g., Ittig et al., *Nucleic Acids Res.* 32:346-353 (2004); Ittig et al., Prague, Academy of Sciences of the Czech Republic. 7:21-26 (Coll. Symp. Series, Hocec, M., 2005); Ivanova et al., *Oligonucleotides* 17:54-65 (2007); Renneberg et al., *Nucleic Acids Res.* 30:2751-2757 (2002); Renneberg et al., *Chembiochem.* 5:1114-1118 (2004); and Renneberg et al., JACS. 124:5993-6002 (2002). In one embodiment, antisense compounds targeted to a target nucleic acid comprise a locked nucleotide, an ethyl-constrained nucleotide, or an alpha-L-locked nucleic acid. Various alpha-L-locked nucleic acids are known by those of ordinary skill in the art, and are described in, e.g., Sorensen et al., *J Am. Chem. Soc.* (2002) 124(10): 2164-2176.

In certain embodiments, antisense compounds targeted to a mutant target nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format wherein 9 non-locked nucleotides are flanked by 3 locked nucleotides on each side.

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2 °C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C \equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a target nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format wherein 9 non-locked nucleotides are flanked by 3 locked nucleotides on each side. In certain embodiments, antisense compounds targeted to a target nucleic acid comprise one or more modified nucleotides. In some embodiments, the modified nucleotide is 5-methylcytosine. In certain embodiments, each cytosine is a 5-methylcytosine.

In certain embodiments, the antisense oligonucleotides of the disclosure comprise a 2'-O-(2-methoxyethyl) modification at one or more nucleotides. In certain embodiments, the antisense oligonucleotides of the disclosure comprise a 2'-O-(2-methoxyethyl) modification at 20% of the nucleotides, at 30% of the nucleotides, at 40% of the nucleotides, at 50% of the nucleotides, at 60% of the nucleotides, at 70% of the nucleotides, at 80% of the nucleotides, or at 90% of the nucleotides. In certain embodiments, the antisense oligonucleotides of the disclosure comprise a 2'-O-(2-methoxyethyl) modification at every nucleotide (100% 2'-O-(2-methoxyethyl) modification).

In certain embodiments, the antisense oligonucleotides of the disclosure comprise one or more phosphorothioate internucleoside linkages. In certain embodiments, the antisense oligonucleotides of the disclosure comprise one or more phosphorothioate internucleoside linkages and one or more phosphodiester linkages. In certain embodiments, the antisense oligonucleotides of the disclosure comprise phosphorothioate at every internucleoside linkage.

In certain embodiments, the antisense oligonucleotides of the disclosure comprise a sequence modification pattern of XsXsXsXsXsXsXsXsXsXsXsXsXsXsXsXsXsXs, XsXsXsXsXsXsXsXsXsXsXsXsXsXsXsXsXsXsXs,
or XsXsXsXsXsXsXsXsXsXsXsXsXsXsXsXsXsXsXsXs, wherein: s represents a phosphorothioate internucleoside linkage; and X represents an adenosine, a guanosine, a cytidine, or a thymine comprising a 2'-O-(2-methoxyethyl) modification.

In certain embodiments, an antisense oligonucleotide that targets a target transcript is from about 8 to about 80 nucleotides in length. In other embodiments, the antisense oligonucleotide that targets a target transcript is from about 15 to about 25 nucleotides in length. In other embodiments, the antisense oligonucleotide that targets a target transcript is from about 18 to about 20 nucleotides in length. For example, the antisense oligonucleotides are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or a range defined by any two of the above values.

Diseases and Disorders of Haploinsufficiency, and Related Genes.

The methods described herein can be used to identify non-productive splice sites in the target RNA transcripts expressed from genes that are related, or associated with, diseases or disorders of haploinsufficiency. For haploinsufficient genes, when one copy of a gene is deleted or contains a loss-of-function mutation, the dosage of normal product generated by the single wild-type, or otherwise functional gene, is not sufficient for the complete function of the expressed protein. That is, there is not enough of the protein being produced, and a disease state occurs (a disease or disorder of haploinsufficiency).

Identified non-productive splice sites in the target RNA transcripts can be targeted with the steric blocking antisense oligonucleotides described herein to increase the level of functional RNA transcript and functional protein encoded by said transcript.

Genes and corresponding target RNA transcripts related to diseases or disorders of haploinsufficiency include, but are not limited to, ADAR, ARSA, ATP1A2, CACNA1A, CHD7, CTNNB1, DNMT1, EHMT1, EIF2B1, EIF2B2, EIF2B5, GRN, HTR7, IDUA, JAK2, KCNQ4, LEPR, LIPC, MBD5, MFSD8, MNX1, NF2, NFIA, NMU, NOTCH1, NPCl, NSD1, PAX6, PEX1, PHIP, PKD1, PRICKLE2, PRRT2, PYY, RAI1, RBPJ, RPS14, RUNX2, SETBP1, SETD5, SHANK3, SLC6A1, STXBP1, STX1B, SYNGAP1, TBX1, TCF4, TGIF1, and WDTC1.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The present invention is further illustrated by the following examples which should not be construed as further limiting.

Example 1—Materials and Methods

Antisense Oligonucleotides

All phosphoramidites will be purchased from ChemGenes. 0.1M DDTT (ChemGenes) will be used as the sulfurising reagent and 0.25M BTT (AIC) as the activator. Antisense oligonucleotides will be synthesized on Dr. Oligo 48, ABI394, AKTA Oligopilot10 or AKTA Oligopilot 100 synthesizers, according to the required scale. MOE phosphoramidites will be coupled for 8 minutes. Oligonucleotides will be deprotected in concentrated aqueous ammonia at 55 °C for 18 h and purified using ion-exchange chromatography (eluting with 30% acetonitrile in water containing increasing gradients of $NaClO_4$). Final purification, desalting, concentration and pH adjustment will be effected by diafiltration in an Amicon centrifugal filter. All oligonucleotides will be characterized by LCMS.

Cell Line Selection

Splice site identification and antisense oligonucleotide testing experiments must be performed in a cell line in which SLC6A1 is transcriptionally active. Furthermore, since SLC6A1 intronic sequences are not well conserved between mouse and human and cryptic splice sites often occur in introns, experiments must be performed in a human cell line. The experimentally tractable human SH-SY5Y cell line (derived from neuroblastoma cells) expresses SLC6A1 (FIG. 1). However, it would be more optimal to perform these experiments in human GABAergic interneurons. Given that these are impossible to obtain from a living patient, approaches have been recently developed to differentiate GABAergic inhibitory neurons (iNs) from human embryonic stem cells (hESCs) or induced pluripotent stem cells (iPSCs). Thus, initial experiments and optimizations will be performed in parallel in SH-SY5Y cells and in iNs derived from commercial hESCs and an iPSC line derived from a clinical subject.

4sU Labeling of Nascent RNA Intermediates

Short time point metabolic labelling of SH-SY5Y cells with 4-thiouridine (4sU) will be carried out as described (Dolken et al. 2008; Pai et al., 2017). 4sU incorporates into newly created RNA in the place of standard uridine nucleotides and can be selectively isolated to capture nascent RNA shortly after its biogenesis. SH-SY5Y cells will be cultured in DMEM supplemented with 10% FBS. Newly transcribed RNA from three independent replicates of SH-SY5Y cells will be labeled for various time intervals, for example, 2, 5, 15 or 30 min, using 500 μM 4-thiouridine (Sigma, T4509). Additionally, for analysis of steady-state RNA levels, two independent biological replicates of SH-SY5Y cells will be generated without 4sU labeling. To normalize samples and assess metabolic labeled RNA capture efficiency, several synthetic RNAs will be spiked into the Trizol preparation at specific quantities per $10^6$ cells. Quantities will be determined as described previously (Henriques et al., 2013).

RNA Extraction and Quantitative RealTime-PCR

Total RNA will be isolated from SH-SY5Y cells using Trizol (ThermoScientific) and subsequently treated with DNase I (Qiagen). One μg of total RNA will be reverse transcribed into cDNA using random hexamers and Multi-Scribe reverse transcriptase (ThermoScientific) following the manufacturer's instructions. Quantitative PCR will be performed on a StepOnePlus Real-Time PCR system using SYBR Green Master Mix (Applied Biosystems) and 0.2 μM of forward and reverse primers as described in (Jiang et al., Neuron, 2016, 90, 535-550; Tran et al, 2015, Neuron, 87, 1207-1214). Ct values for each sample and gene will be normalized to GAPDH. The 2(−ΔΔCt) method was used to determine the relative expression of each target gene.

Biotinylation of Nascent 4sU-Labeled RNA Intermediates

To purify metabolic labeled RNA 300 μg total RNA will be used for the biotinylation reaction. Separation of total RNA into newly transcribed and untagged pre-existing RNA will be performed as previously described (Windhager et al., 2012; Cleary et al., 2005). Specifically, 4sU-labeled RNA will be biotinylated using EZ-Link Biotin-HPDP (Thermo Fisher, Waltham MA), dissolved in dimethylformamide (DMF) at a concentration of 1 mg/ml. Biotinylation will be done in labeling buffer (10 mM Tris pH 7.4, 1 mM EDTA) and 0.2 mg/ml Biotin-HPDP for 2 hr at 25 °C. Unbound Biotin-HPDP will be removed by extraction with chloroform/isoamylalcohol (24:1) using MaXtract (high density) tubes (Qiagen, Germany). RNA will be precipitated at 20,000 g for 20 min with a 1:10 vol of 5 M NaCl and 2.5× volume of ethanol. The pellet will be washed with ice-cold 75% ethanol and precipitated again at 20,000 g for 5 min. The pellet will be resuspended in 1 ml RPB buffer (300 mM NaCl, 10 mM Tris pH 7.5, 1 mM EDTA).

Capturing Biotinylated 4sU RNA

Biotinylated 4sU RNA will be captured using Streptavidin MagneSphere Paramagnetic particles (Promega, Madison WI). Before incubation with biotinylated 4sU RNA, streptavidin beads will be washed four times with wash buffer (50 mM NaCl, 10 mM Tris pH 7.5, 1 mM EDTA) and blocked with 1% polyvinylpyrrolidone (Millipore Sigma, Burlington MA) for 10 min with rotation. Biotinylated 4sU RNA will then be incubated with 600 μl of beads with rotation for 30 min at 25 °C. Beads will be magnetically fixed and washed 5 times with 4TU wash buffer (1 M NaCl, 10 mM Tris pH 7.5, 1 mM EDTA, 0.1% Tween 20). Unlabeled RNA present in the supernatant will be discarded. 4sU RNA will be eluted twice with 75 μL of freshly prepared 100 mM dithiothreitol (DTT). 4sU RNA will be recovered from eluates by ethanol precipitation.

Library Preparation

RNA quality will be assessed using a Bioanalyzer Nano ChIP (Agilent). Ribosomal RNA will be removed prior to library construction by hybridizing to ribo-depletion beads that contain biotinylated capture probes (Ribo-Zero, Epicentre, Madison WI). RNA will then be fragmented and libraries will be prepared according to the TruSeq Stranded Total RNA Gold Kit (Illumina, San Diego CA) using random hexamer priming. cDNA for the two 'total' RNA samples will be prepared using an equal mix of random hexamers and oligo-dT primers (Pai et al., 2017).

Illumina Sequencing

Libraries will be sequenced on an Illumina HiSeq machine with paired-end 150 nucleotide reads (100 nucleotide reads for the 'total' RNA samples), for an average of 100 million read pairs per library. Reads for each sample will be filtered, removing pairs where the mean quality score of one or both mates fell below 20. Mean fragment length and standard deviation will be assessed using CollectInsertSizeMetrics, a component of Picard Tools 1.62. All reads will subsequently be aligned to hg38 with STAR. Strand-specific alignments will be performed for the 4sU RNA-seq (—library-type first strand), while unstranded alignments will be performed for the total RNA-seq (—library-type unstranded).

Identification of Non-Productive Splicing

Sites of non-productive splicing will be identified by non-annotated junction reads with canonical or non-canonical splice site sequences within annotated introns using nascent RNA reads from short labeling periods. To do so, the raw 4sU-seq reads will be re-mapped with the STAR v2.5 software (Dobin et al., Bioinformatics. 2013; 29(1):15-21), with the mapping parameter—outSAMattribute NH HI AS nM jM to mark the intron motif category for each junction read in the final mapped file.

The jM attribute adds a jM:B:c SAM attribute to split reads arising from exon-exon junctions. All junction reads will be first isolated and separated based on the value assigned to the jM:B:c tag. Junction reads spanning splice sites in the following categories will be considered to be annotated or canonical: (1) any annotated splice site [jM:B:c[20-26]], (2) intron motifs containing "GT-AG" (or the reverse complement) [jM:B:c,1 or jM:B:c,2], (3) intron motifs containing "GC-AG" (or the reverse complement) [jM:B:c,3 or jM:B:c,4], and (4) intron motifs containing "AT-AC" (or the reverse complement) [jM:B:c,5 or jM:B:c,6]. Junction reads with jM:B:c,0 will be considered to arise from non-canonical non-annotated splice sites.

Statistical Analysis

All data will be graphed as mean SEM and analyzed using GraphPad Prism Software (Version7). Tests between two groups will use the two-tailed student-t test. Tests between multiple groups used one-way analysis of variance (ANOVA) corrected with Bonferroni multiple comparison post-hoc test. *p<0.05, p<0.01, *p<0.001, ****p<0.0001, ns not significant

Example 2—Identifying Cryptic Splice Sites by Using Computational Software

Figure 2:
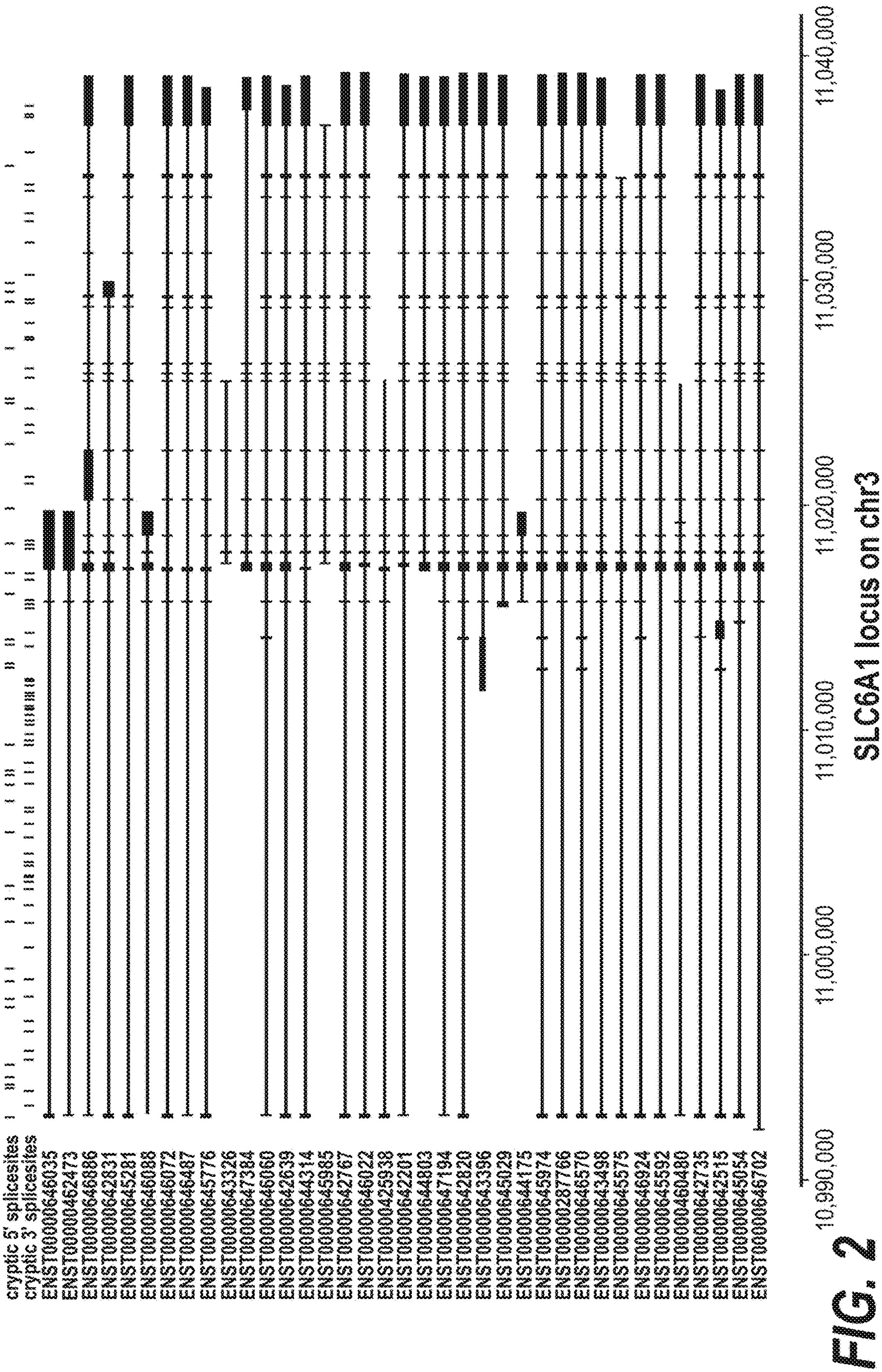
FIG. 2 depicts the schematic of the SLC6A1 genetic locus on human chromosome 3. Structures for the 37 most comprehensive annotated isoforms are shown (bottom), with common exons (i.e. represented in at least 50% of isoforms) highlighted in black. Computationally predicted cryptic splice sites (5' splice sites and 3' splice sites) are indicated by dashes at the top.

Identifying transcripts that are being created but not lasting until maturity would enable targeted optimization of mRNA processing pathways to allow for maturation of these transcripts. The first challenge is to identify sites at which non-productive splicing commonly occurs. Those sites can then be blocked by complementary antisense oligonucleotides to redirect the splicing machinery towards sites promoting productive splicing. SLC6A1 is a 46.5 kb gene with 17 introns and extensive alternative splicing, increasing the probability that many cryptic splice sites exist within this genomic space. Two complementary approaches will be used to identify sites of non-productive splicing in SLC6A1-expressing neurons: (1) computational identification of strong cryptic splice sites and (2) targeted sequencing of SLC6A1 mRNA intermediates (see Example 3). Computational software will be used to identify the sites that may underlie non-productively spliced isoforms. The commonly used maxEnt splice site algorithm will be applied, which uses a maximum entropy model to score sites relative to the entropy of known 5' or 3' splice site elements (Yeo and Burge 2004). Publicly available MaxEnt resources are available at: http://hollywood.mit.edu/burgelab/maxent/Xmaxentscan_scoreseq.html; MaxEntScan::score5ss will be used for human 5' splice sites and MaxEntScan::score3ss will be used for human 3' splice sites. The SLC6A1 genetic locus on human chromosome 3 is shown in FIG. 2.

A sliding window algorithm will be used to scan every 9 and 23 nucleotide region segments in the human SLC6A1 gene sequence and the maximum entropy for 5' and 3' splice site motifs will be calculated, respectively. After removing annotated splice sites, an entropy threshold to identify high-scoring putative cryptic splice sites will be conditioned on.

Initial analyses of SLC6A1 RNA with maxEnt have identified 34 cryptic 5' splice sites, depicted as SEQ ID NOs. 1 to 34 in Table 1, and 74 cryptic 3' splice sites, depicted as SEQ ID NOs. 35-108 in Table 2. SEQ ID No. 109 depicts the entire SLC6A1 RNA sequence. Genomic scanning scripts will be used to identify high-scoring cryptic polyadenylation sites in SLC6A1, the usage of which might lead to truncated isoforms that are similarly targeted for degradation. Once identified, these sites can be targeted with antisense oligonucleotides to block the formation of non-productive, truncated transcripts.

The nucleic acid target sequences of Table 1 and Table 2, and genomic sequences of Table 4, correspond to the genomic target sequence. An antisense oligonucleotide is designed to have sufficient complementarity to the corresponding RNA transcript expressed from said genomic target sequence (i.e., the reverse complement of the genomic target sequence, where each T is replaced by a U). For example, but in no way limiting, an antisense oligonucleotide may possess sufficient complementarity to CAGCCUGAUUCUGCCUGUGACUCACUUUGUGACCUCAGGAGAGUCCCUCC (SEQ ID NO: 301) (the RNA transcript sequence corresponding to SEQ ID NO: 1 in Table 1) to block the formation of non-productive, truncated transcripts.

Example 3—Targeted High-Throughput Sequencing of SLC6A1 Nascent RNA Intermediates Targeted high-throughput sequencing of SLC6A1 nascent RNA intermediates will be performed to experimentally identify short-lived non-productive isoforms. Nascent RNA intermediates will be captured with methods as described in Example 1. To obtain high-resolution information about nonproductive SLC6A1 splicing, biotinylated probes complementary to regions of the gene to selectively isolate SLC6A1 mRNA will be used from the pool of nascent RNA. Probes will be designed to have optimal nucleotide composition and chemistry, match a unique location in the human genome (<70% match to a second location), and be located within exons that are included within 50% of annotated SLC6A1 isoforms (FIG. 1). The probes will tile across these exons within SLC6A1, located at the beginning, middle, and end of the gene to enable the most comprehensive capture of entire distribution of possible isoforms. Nascent SLC6A1 RNA across all intermediate lifetimes will be sequenced using a combination of short-read and long-read high-throughput sequencing. Short-read sequencing with the Illumina platform provides the ability to obtain high-resolution information about cryptic splice site usage with higher coverage. A total of 12 libraries (3 replicates for each of the 5, 15, 30-minute nascent RNA timepoints and 3 replicates of the steady state sample) will be sequenced in 1 NextSeq lane, with an estimated 450 million reads across all libraries. These data will be used to comprehensively identify sites of cryptic splicing leading to non-productive isoforms across a range of mRNA intermediate lifetimes. To do so, non-canonical splicing junctions will be identified by specifically analyzing splitreads that do not map to annotated SLC6A1 exon-exon junctions. Cryptic splice sites that recurrently have split-junction reads in multiple samples and after sub-sampling approaches will be considered to be major sites of cryptic splicing in SLC6A1. Open reading frames (ORFs) will be predicted and premature stop codon usage in all isoforms (both annotated and cryptic) expressed in neuronal systems and identified through this analysis. These predictions will be used to quantify the probability that cryptic splice site usage leads to isoform degradation through nonsense mediated decay (NMD) pathways. Splice sites that lead to NMD will be prioritized for downstream antisense oligonucleotide design and targeting approaches (Aim 2). Further Oxford Nanopore Minion cDNA libraries will be generated with the same 12 samples and sequence them across 2 Minion flowcells to assess the long-range connectivity between different cryptic sites. Since long-read datasets are inherently error prone, annotations of cryptic splice sites derived from the short-read Illumina data will be used to refine mapping of the long-read Minion data. These data will provide isoform level insights that may be useful for combinatorial targeting of multiple cryptic splice sites for maximal effect with a minimal number of antisense oligonucleotides.

Example 4—Use of Publicly Available Datasets

For a more comprehensive picture of non-productive splicing isoforms in SLC6A1, publicly available sequencing datasets will be analyzed that are designed to capture total cellular mRNA, as opposed to only polyadenylated mature mRNA (Schwarzl et al. 2015; Rybak-Wolf et al. 2015; Pandey et al. 2014). We will also generate a genome-wide nascent RNA sequencing dataset with SH-SY5Y cells, neurons derived from human embryonic stem cells, and neurons derived from induced-pluripotent stem cells. These datasets will all be enriched for mature polyadenylated RNA but will also contain a small amount of information about intermediate RNA species. In all of these datasets, we will identify novel isoforms of SLC6A1 (using the MAGIQ splicing analysis software), and identify splicing junction reads.

Example 5—Antisense Oligonucleotides Targeting Non-Productive Splice Sites that Increase the Expression of Productive SLC6A1 mRNA Molecules Computational software was used to identify cryptic splice sites that are likely to underlie non-productively spliced isoforms of SLC6A1. Specifically, the maxEnt splice site algorithm was applied, which uses a maximum entropy model to score sites relative to the entropy of known 5' or 3' splice site elements (Yeo and Burge 2004). A sliding window algorithm was used to scan every 9 and 23 nucleotide region segment in the human SLC6A1 gene sequence and calculate the maximum entropy for 5' and 3' splice site motifs, respectively. After removing annotated splice sites, an entropy threshold of 8.72 and 7.25 (mean entropy scores for annotated sites) were used to identify high-scoring putative cryptic 5' and 3' splice sites, respectively. Initial computational analyses identified 12 cryptic 5' splice sites and 84 cryptic 3' splice sites in SLC6A1. The number of predicted sites that would target was narrowed to 15 (5 5' splice sites and 10 3' splice sites) based on their position along the SLC6A1 locus (focusing on intron 1) and maximizing the specificity of those sites by selecting antisense oligonucleotides with minimal complementarity to other sites in the transcriptome using NCBI BLAST.

Three antisense oligonucleotides were selected for each of the 15 predicted sites. These antisense oligonucleotides were designed as steric blockers, with each nucleotide comprising a 2'-O-methoxyethyl RNA (MOE) modification and a phosphorothioate backbone. Each antisense oligonucleotide was 20 nucleotides in length. 45 antisense oligonucleotides were synthesized using standard methods on a Dr. Oligo 48 synthesizer, and their identity and purity was confirmed by high performance liquid chromatography coupled to mass spectroscopy (LCMS).

Each antisense oligonucleotide was transfected into KNS60 neuroblastoma cells (JCRB Cell Bank). These cells were cultured in DMEM (Sigma) supplemented with 5% fetal bovine serum at 37 °C with 5% CO2. One day prior to transfection, cells were seeded at a density of 50,000 and incubated overnight. Cells were transfected with 50 nM antisense oligonucleotide using Lipofectamine RNAiMAX (Thermofisher) transfection reagent.

After 24 hours, RNA was collected using TRI Reagent (Sigma) and subjected to reverse transcription using the High-Capacity cDNA Reverse Transcription kit (ThermoFisher) according to the manufacturer's instructions. Resulting cDNA was used for qPCR reaction with IDT PrimeTime Taqman primers for SLC6A1 (Hs.PT.58.40113647) and GAPDH (Hs.PT.39a.22214836). The qPCR was performed in technical duplicate on a Bio-Rad CFX96 Real-Time System Thermal Cycler.

Figure 3:
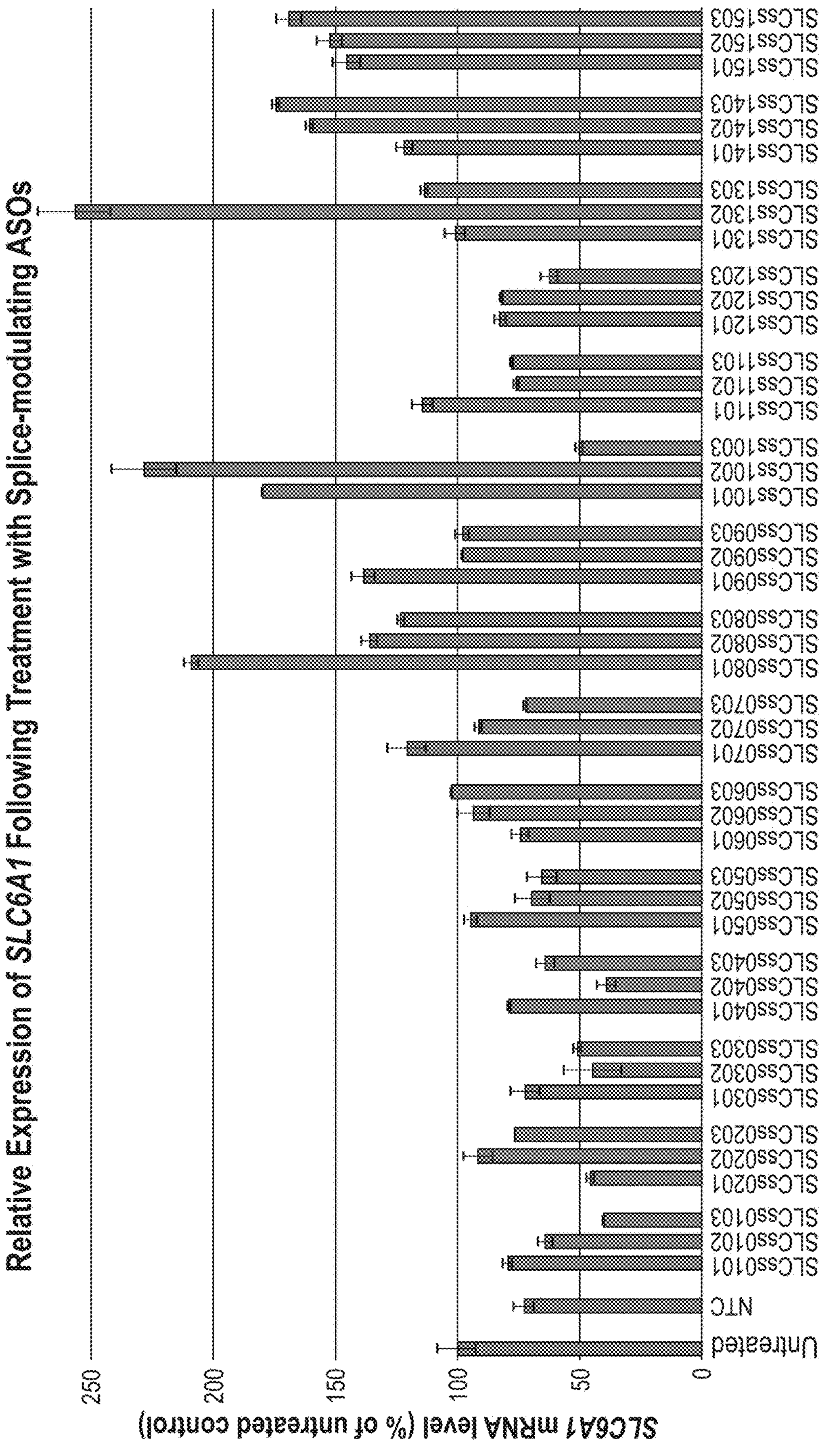
FIG. 3 depicts a bar graph of SLC6A1 relative mRNA levels in KNS60 neuroblastoma cells transfected with various steric blocking antisense oligonucleotides at 50 nM.

Several of the antisense oligonucleotides produced activation of SLC6A1 as seen by up to 2.5-fold increases in mRNA expression (FIG. 3). Sequences, masses, target sites, and percent activation details of active antisense oligonucleotides are presented in Table 3.

Example 6—Identifying Novel Cryptic Splice Sites by Enrichment and Sequencing of Nascent Pre-mRNA Publicly available high-throughput sequencing data was used to identify cryptic splice sites that are used only in splicing intermediates targeted for degradation (i.e., not present in steady-state mRNA sequencing data). Specially, raw data was downloaded from 3 datasets derived from human K562 erythroleukemia cells: (1) mRNA enriched by capturing a polyA tail (ENCODE Consortium), (2) mRNA after an shRNA knockdown of the UPF1 degradation machinery (ENCODE Consortium), and (3) pre-mRNA enriched by labeling nascent RNA with 4-thio-uridine for 5 minutes and using a biotin-streptavidin interaction to selectively isolate nascent RNA (Schwalb et al. Science. 2016; 352(6290):1225-8). All datasets were mapped to the human reference genome (hg38) with the STAR transcriptome mapping software (Dobin 2013, supra) and a custom python script was used to annotate the split-junction reads from the *.SJ.out.tab file from the STAR output. Junction sites were described as being annotated or unannotated based on presence in the Ensembl GRCh38.95 annotation database. Junction sites were also described as canonical or non-canonical based on the dinucleotide sequences used for the 5' splice site and 3' splice sites (GT, GC, AT, and corresponding reverse complements, or AG, AC, and corresponding reverse complements were considered to be canonical 5' or 3' splice sites, respectively). Only junction sites for which both ends of the read mapped to the same gene and one or both of the splice site dinucleotides were either non-canonical or unannotated as splice sites were retained for further analysis. These junction reads were deemed to be cryptic splice sites by virtue of their lack of annotation or canonical dinucleotide status.

Figure 4:
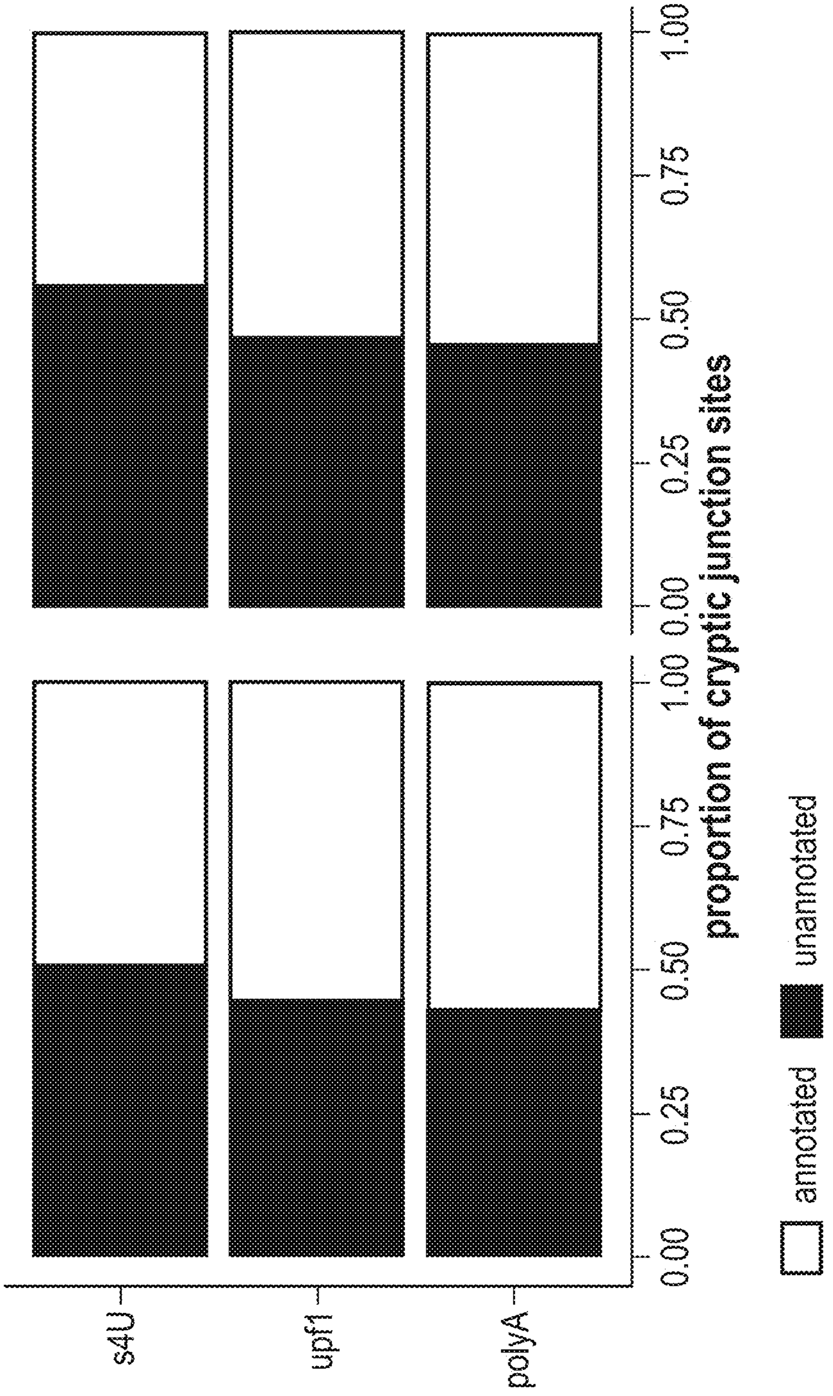
FIG. 4 depicts a schematic of the distribution of annotated and unannotated 5' and 3' splice sites across cryptic junction sites, which are defined as either unannotated or using non-canonical dinucleotide sequences.
Figure 5:
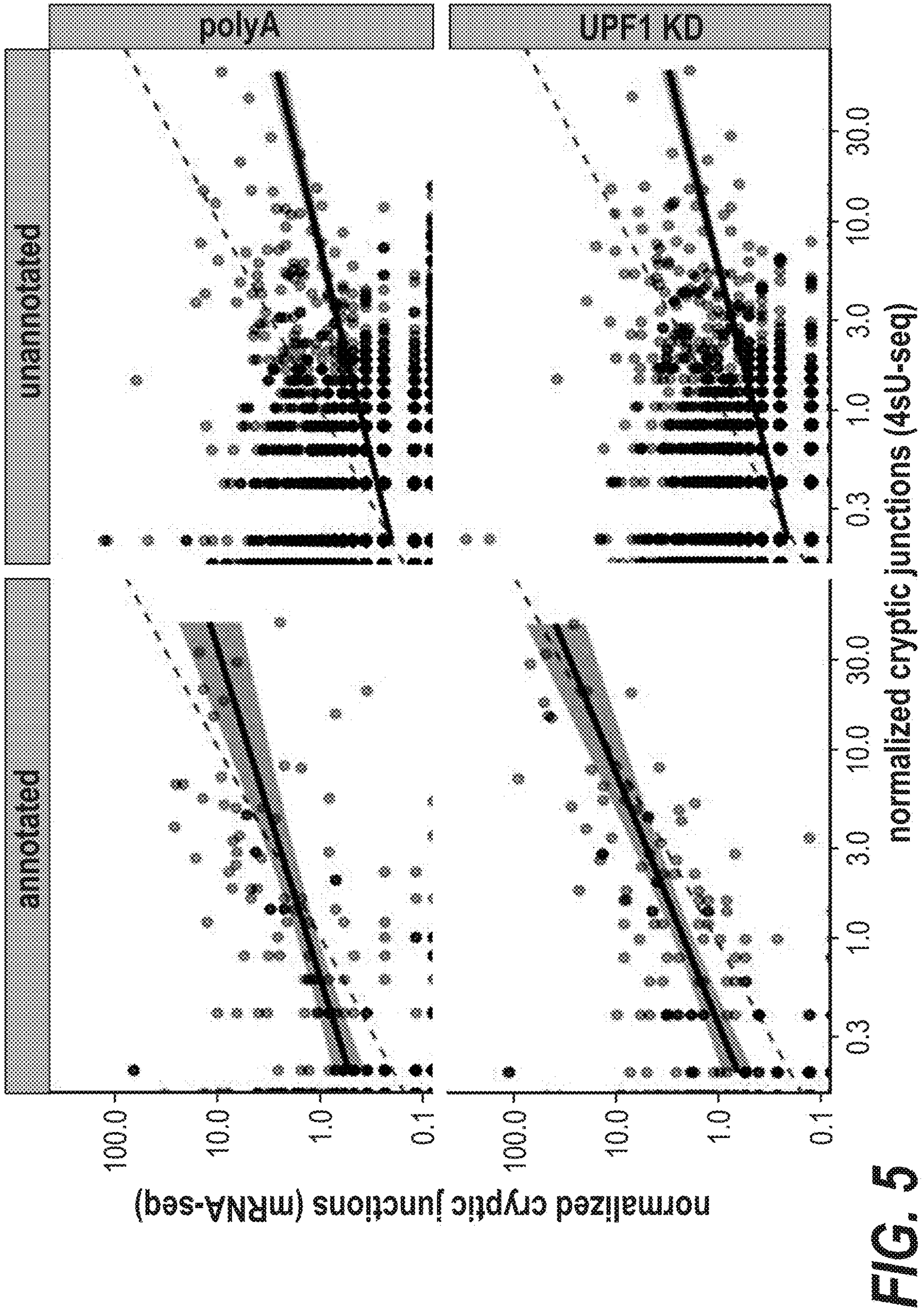
FIG. 5 depicts a schematic of the number of reads for individual cryptic junction sites in metabolic labeling sequencing data (4sU-seq, x-axis) relative to non-metabolic labeling data (polyA mRNA or mRNA from UPF1 knockdown, y-axis). Solid grey lines represent a linear fit to the data, while dotted lines represent a correlation of 1.

For each dataset, the proportion of cryptic sites that were previously annotated as being used as splice sites were evaluated (FIG. 4). There is an increase of unannotated 5' and 3' splice sites in the nascent RNA 4sU-sequencing data relative to the steady-state polyA enriched mRNA or the mRNA from UPF1-depleted cells, which should contain more mRNAs that are quickly degraded in homeostatic conditions. Across individual cryptic sites, there is an overall increase in the number of junction reads for the majority of cryptic sites in the 4sU-seq data relative to both non-metabolic labeled datasets (FIG. 5). Together, these data show that specifically isolating and sequencing nascent RNA with metabolic labeling have increased power to detect more active cryptic splice sites with higher signal than either steady-state polyA enriched mRNA sequencing or mRNA sequencing after perturbation of degradation machinery cells (i.e., UPF1-depleted cells).

Several of the novel cryptic sites that were identified using the 4sU-seq data were present in genes that are known to be haploinsufficient when mutated. From a representative list of 92 genes known to be involved in haploinsufficiency disorders and expressed in K562 cells, 190 novel cryptic splice sites were identified across 31 genes that were identified using the 4sU-seq data but absent in both the steady-state polyA mRNA-seq or UPF1 knockdown datasets (Table 4).

TABLE 1

Target sequences for 34 cryptic 5' splice sites

| SEQ ID NO. | Target Location | Nucleic acid target sequence |
|---|---|---|
| 1 | >SLC6A1::3:10992186-11039247; startsite = 11029076; maxEnt = 8.4(+) | GGAGGGACTCTCCTGAGGTCACAAAGTGAGTCACAGGCAGAATCAGGCTG |
| 2 | >SLC6A1::3:10992186-11039247; startsite = 11018312; maxEnt = 10.13 (+) | TGACAGGCACCCAGGTAGATACATGGTGAGTCATGCTCACTGACCGAGGG |
| 3 | >SLC6A1::3:10992186-11039247; startsite = 11026999; maxEnt = 8.49(+) | GTCACAGAGATCACATGCTCACAAGGTAATAAAATATCACAAGGCAAATG |
| 4 | >SLC6A1::3:10992186-11039247; startsite = 11008010; maxEnt = 8.63 (+) | ATGGAGGGTTTGGGGGGTTCCACAGGTACCCCATTAGAGACAGCAGAGTG |

TABLE 1-continued

| SEQ ID NO. | Target Location | Nucleic acid target sequence |
|---|---|---|
| 5 | >SLC6A1::3:10992186-11039247; startsite = 10994543; maxEnt = 8.34(+) | GTGGCCAGTCCTTGGAGGACAAACAGTGAGTCCCAAGCAGAGAGACGCAG |
| 6 | >SLC6A1::3:10992186-11039247; startsite = 10999403; maxEnt = 8.08(+) | TGTATTACATATGCATTTTTAGCAGGTTGGTTCAGCATAATGACACAGAA |
| 7 | >SLC6A1::3:10992186-11039247; startsite = 10994225; maxEnt = 7.7(+) | TCCCCCAAATTCCAAAACAAAAGAGGTCAGTGAAAGCTACTCGCATTTTG |
| 8 | >SLC6A1::3:10992186-11039247; startsite = 11016980; maxEnt = 7.62(+) | TTCCTTCCTCCAGGAGCAAGGGCGGGTGAGAGGAAGAGGGCTTATAGAGA |
| 9 | >SLC6A1::3:10992186-11039247; startsite = 11019859; maxEnt = 7.52(+) | CTGCGCCTGGCAGAGAACAAGCCCTGTAAGTGTTTGCTGGTGTCGTTGCA |
| 10 | >SLC6A1::3:10992186-11039247; startsite = 11003074; maxEnt = 9.99(+) | CTAAAAATACAAAAAAATTAGCCAGGTATGGTGGCAGGCACCTGTAGTCC |
| 11 | >SLC6A1::3:10992186-11039247; startsite = 11024724; maxEnt = 8.55(+) | TATTTAGAGTCACATAAAATTGGAGGTAACCTGAATGCATAGCAGTGGGG |
| 12 | >SLC6A1::3:10992186-11039247; startsite = 11024566; maxEnt = 8.49(+) | AGTTCCATTTCTCGAAAGCAACAAGGTAATATGGATCAAAAGCCTGTGAT |
| 13 | >SLC6A1::3:10992186-11039247; startsite = 11012797; maxEnt = 9.65(+) | TTTCTTCCGCCTGCTCCACCAGCAGGTAAAGGAGGCTGATCACAGGCTGG |
| 14 | >SLC6A1::3:10992186-11039247; startsite = 11009361; maxEnt = 10.65(+) | CCTGCTTCTGCAAATTCCCTCTCAGGTACGTTGAGGCAGCTGAGGGGTTT |
| 15 | >SLC6A1::3:10992186-11039247; startsite = 10992782; maxEnt = 8.19(+) | GACCGAGACAGCGGAGAGGTTGCGGGTGAGCTGCGCTGAGCCCAGGAGCC |
| 16 | >SLC6A1::3:10992186-11039247; startsite = 11029491; maxEnt = 8.34(+) | TGTGCCAAGCTCTGGGCACATAACAGTGAGTCAGATGGGGTCCCTGCCCT |
| 17 | >SLC6A1::3:10992186-11039247; startsite = 11006834; maxEnt = 9.21(+) | GTGTGATCATCATTCTTATTACAGGGTAAGATGCGCCCTCTTTTCCTGCA |
| 18 | >SLC6A1::3:10992186-11039247; startsite = 11022717; maxEnt = 8.34(+) | TACGCAGCACAGTGCGAAGCTCACAGTGAGTCCCATGGGATTCCACTGGG |
| 19 | >SLC6A1::3:10992186-11039247; startsite = 10997671; maxEnt = 8.7(+) | GGGAGAGGGCAGCAGCCACAGGGAGGTGAGCAAAGACATTTGGTATCAGT |
| 20 | >SLC6A1::3:10992186-11039247; startsite = 11005443; maxEnt = 10.08(+) | ACCTCAGGCTTCTCTTGGCTGAAAGGTAGGCTCCTTCCCTCCCTCCTTGG |
| 21 | >SLC6A1::3:10992186-11039247; startsite = 11007557; maxEnt = 8.78(+) | GGACTGGCATAAGGTCACACAGCTAGTAAGTTTAGAGAGAGATTTCAAAC |
| 22 | >SLC6A1::3:10992186-11039247; startsite = 11008216; maxEnt = 7.79(+) | CATTTAGAGTGGCCCCGGCACATTAGTAAGTGTGTCCAGCTCACTTCCTC |

TABLE 1-continued

| Target sequences for 34 cryptic 5' splice sites | | |
|---|---|---|
| SEQ ID NO. | Target Location | Nucleic acid target sequence |
| 23 | >SLC6A1::3:10992186-11039247; startsite = 10995132; maxEnt = 7.7(+) | GCCATTTCTGGCCAGGTGACCTTGGGTACGTTCTTGTTCCTGTTGGAAGG |
| 24 | >SLC6A1::3:10992186-11039247; startsite = 11016045; maxEnt = 10.57(+) | CCACGCTGCCCCTGGAAATAAAAAGGTAAGAAGGCTGCAGAGTGTCAGTA |
| 25 | >SLC6A1::3:10992186-11039247; startsite = 11029877; maxEnt = 8.24(+) | AATCCCAGCTACTTGGGAGGCTGAGGTAGGAGAATTGCTTGAACCCGGGA |
| 26 | >SLC6A1::3:10992186-11039247;startsite = 10998050; maxEnt = 8.83(+) | ACAGCCCTGGGAACTTCAAGTGAAGGTAATTTTATTGTTATTATTGGTAC |
| 27 | >SLC6A1::3:10992186-11039247; startsite = 11014026; maxEnt = 7.61(+) | AAATCACATGTATGTCTGCTTTATGGTGAGGTCTTCAGAGCAGCCACCGT |
| 28 | >SLC6A1::3:10992186-11039247; startsite = 11001471; maxEnt = 10.07(+) | GCACTTCGTGGAGGTGCAGAGTCAGGTGAGGAGAGGTGAAGTGACTCATC |
| 29 | >SLC6A1::3:10992186-11039247; startsite = 11035089; maxEnt = 9.06(+) | GAACGGAGATCAGTGTGGCTGGAAGGTAAAGTGGAAAGGGGTGCGAGGAG |
| 30 | >SLC6A1::3:10992186-11039247; startsite = 10994083; maxEnt = 8.23(+) | CCTTTGTTTTTCTATGACACACAAGGTGGGTGTTTGGCAAGAGAGTAGGG |
| 31 | >SLC6A1::3:10992186-11039247; startsite = 11012956; maxEnt = 8.46(+) | AGGAAAAGTAACAACTTGCAAAAAGGTTGGTTCTGCTTCAGAGAAATGTT |
| 32 | >SLC6A1::3:10992186-11039247; startsite = 10998840; maxEnt = 8.34(+) | GAACTTGTCCAGCTGGGCCCTGACAGTGAGTTCAGAGGGCCTGCTGGGCA |
| 33 | >SLC6A1::3:10992186-11039247; startsite = 11002499; maxEnt = 9.45(+) | GCATTTGGCTGTTTGAAAAGCGCTGGTAAGAGCTGGGATCCTGATGATTG |
| 34 | >SLC6A1::3:10992186-11039247; startsite = 11013805; maxEnt = 7.65(+) | AGCACCAGGGTGGCTTTGCTGCTGTGTAAGTCAAAGAGCCTTCTCCGTTC |

TABLE 2

| Target sequences for 74 cryptic 3' splice sites | | |
|---|---|---|
| SEQ ID NO. | Target Location | Nucleic acid target sequence |
| 35 | >SLC6A1::3:10992186-11039247; startsite = 10995350; maxEnt = 8.94(+) | TAACCCTACTGTTCTAATTTCCAGGCCAACTCTGTCCTATTGTGGGTCTC |
| 36 | >SLC6A1::3:10992186-11039247; startsite = 11024297; maxEnt = 9.97(+) | TGGCTGCCTTCCTTAATCCTGCAGAATCTCGGGGTCAAGTCAGGGAGGTG |
| 37 | >SLC6A1::3:10992186-11039247; startsite = 11016703; maxEnt = 8.34(+) | GGGGACACCTTTCTCCCCATTCAGCCACAGGTGGAGCTTCTTTCTTGCTC |

TABLE 2-continued

Target sequences for 74 cryptic 3' splice sites

| SEQ ID NO. | Target Location | Nucleic acid target sequence |
|---|---|---|
| 38 | >SLC6A1::3:10992186-11039247; startsite = 11029029; maxEnt = 9.21(+) | TCAGCCACCTTCTCCATTTTCCAGAAGGGGAAACTGATGCCCAGAGGGGA |
| 39 | >SLC6A1::3:10992186-11039247; startsite = 11003960; maxEnt = 7.75(+) | ATACCATAAAATTCCTTTCCACAGCTAAGTGAGTGAGTCAAGAACAGATG |
| 40 | >SLC6A1::3:10992186-11039247; startsite = 11012234; maxEnt = 8.97(+) | GTCTTGTTCTTACACCTCTTGCAGCACTTATCACAGGGTATTATGATCAG |
| 41 | >SLC6A1::3:10992186-11039247; startsite = 10998924; maxEnt = 8.12(+) | GGTGCTACTCTCTCCTTCTGCCAGAGAGGACCCTGAGCCCAAGGGTGGTG |
| 42 | >SLC6A1::3:10992186-11039247; startsite = 11004488; maxEnt = 7.9(+) | CATCACCACTTCCCTTCTCCAAAGCATGCAAGTTCAATTTCTAAAATTCA |
| 43 | >SLC6A1::3:10992186-11039247; startsite = 11010695; maxEnt = 8.06(+) | ATTAATTTCTTTCTTAAACCACAGAGTTTCAAAAAGAAATAAAGGCAAAC |
| 44 | >SLC6A1::3:10992186-11039247; startsite = 11023592; maxEnt = 8.93(+) | AAAGTATCTCTGATCCATTCCTAGGACTAGGGACGCCGGAGGAGGGCACA |
| 45 | >SLC6A1::3:10992186-11039247; startsite = 11018094; maxEnt = 7.61(+) | TGACATCACATATCCATCCACCAGGTGCATATCTGAGCAGAGTGAGGGCT |
| 46 | >SLC6A1::3:10992186-11039247; startsite = 11029153; maxEnt = 8.31(+) | GCTGGGCCTCCCGTCCTTCCTTAGAGGGCCAGGCTTTGGGTGGGTTGGGG |
| 47 | >SLC6A1::3:10992186-11039247; startsite = 11030256; maxEnt = 8.3(+) | TCACCCCCACCCCCCCCCCACCAGATCCAAATGTAGTTCTGCTCCAGAGT |
| 48 | >SLC6A1::3:10992186-11039247; startsite = 11006564; maxEnt = 10.01(+) | TCTCCTCTCCTCCTCCCCACACAGCTGCTGGGCGGTCTTGCCAAGTCACC |
| 49 | >SLC6A1::3:10992186-11039247; startsite = 11032621; maxEnt = 7.74(+) | AATAATTTCTTTTCCTTTGGATAGATAGCCAGTAGTGGGATTGCTGGATC |
| 50 | >SLC6A1::3:10992186-11039247; startsite = 11010424; maxEnt = 8.08(+) | CAAGGCTGTTTCCTTATCTGTCAGATGGGTGAGGTAGCCCTGGCTTACAT |
| 51 | >SLC6A1::3:10992186-11039247; startsite = 11012288; maxEnt = 8(+) | AGGCAGAAATATTTCTCCTTCTAGGCCATGACCTTGACAAGGGCAAGGGT |
| 52 | >SLC6A1::3:10992186-11039247; startsite = 11021265; maxEnt = 8.02(+) | AGGCCGTGCTGATTGTATCTTCAGGGGAGTACCTTGTAGAGATGTGTGTC |
| 53 | >SLC6A1::3:10992186-11039247; startsite = 11010986; maxEnt = 9.85(+) | CCTGGCCTCTCGGTCTCTGCCTAGGTCCCCACCCCACGCAGCCGCCTGTC |
| 54 | >SLC6A1::3:10992186-11039247; startsite = 11003518; maxEnt = 10.44(+) | AAAACTGGGTGTCCTTGCCCCTAGGGAAGGACAAATTTTCTTTAAGTCCC |
| 55 | >SLC6A1::3:10992186-11039247; startsite = 11018284; maxEnt = 7.93(+) | TGACTTTCTTTGCCTCGTGCTCAGTGCCTGACAGGCACCCAGGTAGATAC |

TABLE 2-continued

Target sequences for 74 cryptic 3' splice sites

| SEQ ID NO. | Target Location | Nucleic acid target sequence |
|---|---|---|
| 56 | >SLC6A1::3:10992186-11039247; startsite = 10993935; maxEnt = 7.97(+) | TGGAGCGCTCATTCCCTTTCCCAGGAAGCTCAGCCTTATCCCCATGAAGA |
| 57 | >SLC6A1::3:10992186-11039247; startsite = 11003436; maxEnt = 8.89(+) | TAGGTGTTATCACTTCTGTTTTAGACAGAGAGAGTAGATGACTAACCTAC |
| 58 | >SLC6A1::3:10992186-11039247; startsite = 11013708; maxEnt = 8.6(+) | TATTATTATCTTCCCATTTTATAGATGAGGGTCAGAGAGGTGAAGTAACT |
| 59 | >SLC6A1::3:10992186-11039247; startsite = 11010272; maxEnt = 9.79(+) | AAAAATCAGCTTCTCGTTCCACAGGTCTTGAGTGGGGCCCAAGATTCTGC |
| 60 | >SLC6A1::3:10992186-11039247; startsite = 11012201; maxEnt = 8.71(+) | GCTGTATTAATGCGTTTCTTCTAGGCCTCCCGTGTCTTGTTCTTACACCT |
| 61 | >SLC6A1::3:10992186-11039247; startsite = 11027398; maxEnt = 8.42(+) | GGCTCTGTTCCACCTGGCCCACAGGCAGCCAGACGTTAAGGTTATCTCCC |
| 62 | >SLC6A1::3:10992186-11039247; startsite = 11011094; maxEnt = 7.54(+) | CCCCTTGCCTGCCATCTGGTCCAGGGCTGGGCTGCTCACAGCCAATCATC |
| 63 | >SLC6A1::3:10992186-11039247; startsite = 11023244; maxEnt = 8.27(+) | ACTCCACCTTTTCTCCCTTTCAAGCCCTACCCCAGGAGCCTGGGGGCAGA |
| 64 | >SLC6A1:3:10992186-11039247; startsite = 11014323; maxEnt = 8.36(+) | TCTAGTTTTCTCCTTCCTCAGCAGACCAAATCTCACTCTGAGTACAAGAT |
| 65 | >SLC6A1::3:10992186-11039247; startsite = 11027465; maxEnt = 9.35(+) | CTGTTATCCTGTTTTTTTTCCAAGGTGCCCAGATTTCATATTGTTTAAAC |
| 66 | >SLC6A1::3:10992186-11039247; startsite = 11011378; maxEnt = 8.24(+) | CCCACTTCCTCCCATCCCACTTAGAATGAAACCTGAATCCTTGCTGTGAC |
| 67 | >SLC6A1::3:10992186-11039247; startsite = 11025669; maxEnt = 9.61(+) | GCATCTTTCTGACCCTCACTGTAGACCAGGTTTGTTGCCAGGGAGAGCTG |
| 68 | >SLC6A1::3:10992186-11039247; startsite = 11006369; maxEnt = 7.84(+) | GACCTGGGCCCCGTTCTTGCATAGGTGACAGTGCAGCTGGGAAGCTAAGA |
| 69 | >SLC6A1::3:10992186-11039247; startsite = 11031715; maxEnt = 8.13(+) | CTGCACCTTTGATTGTCCCATCAGAGCAAATGTTTTTAAAGAAGCATGAT |
| 70 | >SLC6A1::3:10992186-11039247; startsite = 11015440; maxEnt = 8.64(+) | GCTGCCCTCATCCCACGCCCACAGCTGTCCCGAGGGCAGCGGGCCCCACT |
| 71 | >SLC6A1::3:10992186-11039247; startsite = 11007633; maxEnt = 11.03(+) | AAGCTAACTGCCCTTCCTCCTCAGGTCAGCTCCTCGCAGCAGCTGCAAGG |
| 72 | >SLC6A1::3:10992186-11039247; startsite = 11009538; maxEnt = 9.83(+) | CTGGGTTTTTTTCTTCATCTATAGAATGCCATGGTAGACCAGGTGCACCA |
| 73 | >SLC6A1::3:10992186-11039247; startsite = 11009362; maxEnt = 8.03(+) | CTGCTTCTGCAAATTCCCTCTCAGGTACGTTGAGGCAGCTGAGGGGTTTA |

TABLE 2-continued

Target sequences for 74 cryptic 3' splice sites

| SEQ ID NO. | Target Location | Nucleic acid target sequence |
|---|---|---|
| 74 | >SLC6A1::3:10992186-11039247; startsite = 11008143; maxEnt = 7.54(+) | CACTTTAACCTCTCTGTGCCTCAGTTTACCCATCAATAAAATGGGGGCTA |
| 75 | >SLC6A1::3:10992186-11039247; startsite = 11006520; maxEnt = 7.77(+) | ATCCTTGCACCATCCCTGTTACAGCAACCTCCACCCATGCTCCCTCTCCT |
| 76 | >SLC6A1::3:10992186-11039247; startsite = 11020973; maxEnt = 7.72(+) | TCTCTGCCTCTAATCTCCTGCCAGCTCCTCCCAATGGTCAAACCCAGCTA |
| 77 | >SLC6A1::3:10992186-11039247; startsite = 11011532; maxEnt = 8.06(+) | GTGCCAGGCTCCTTCCTGCCTCAGGGCCTTTGCACTTGCTGCTCCCTCTG |
| 78 | >SLC6A1::3:10992186-11039247; startsite = 11011985; maxEnt = 10.27(+) | ATCAGCCCTGCCCCATCCCTGCAGCTAGTCCCCAGGTTCCTTAGTCCGGT |
| 79 | >SLC6A1::3:10992186-11039247; startsite = 11009833; maxEnt = 7.67(+) | CAGGGAGCTTTCCCTGACCTCCAGGACAGCGCGTGGCAAGCACTGCCCAC |
| 80 | >SLC6A1::3:10992186-11039247; startsite = 11033989; maxEnt = 8.03(+) | TATTGTCCCACTTTACCGCTGCAGGATCTGGGGCTCACCTAGCCAGCATC |
| 81 | >SLC6A1::3:10992186-11039247; startsite = 11002235; maxEnt = 8.56(+) | GAATGTGTGTTTTCTCTGTGCCAGCTATCTAAATGACCCCATGCTGCAAA |
| 82 | >SLC6A1::3:10992186-11039247; startsite = 10996585; maxEnt = 7.73(+) | GCTGTGTGCTTTATATCGTTGCAGTTAATTTTCACAAAACCCTGTGAGAT |
| 83 | >SLC6A1::3:10992186-11039247; startsite = 11002919; maxEnt = 8.57(+) | TTCCTTTATATTGATTGCCTATAGGTTAAGATAACACTGGGCCTGGCGCA |
| 84 | >SLC6A1::3:10992186-11039247; startsite = 10993277; maxEnt = 9.29(+) | CGAAGCTCCCTATTCATTCCCCAGGGCATGGAGGGGACGCGGAGTGAATG |
| 85 | >SLC6A1::3:10992186-11039247; startsite = 11005217; maxEnt = 7.83(+) | TGGGCACCCGGACCTGTTCCACAGGGGCTCGCCCTCGTGCCCAGCACAGG |
| 86 | >SLC6A1:3:10992186-11039247; startsite = 10995733; maxEnt = 9.08(+) | GAAGTCCATCTCCTTTGTCCTTAGAAGCCCATCCCTGTTGCCTAGCCCAA |
| 87 | >SLC6A1::3:10992186-11039247; startsite = 11004115; maxEnt = 9.68(+) | TACACGCCTCCCTCATTCTTGCAGACTATTCTAAAGCAGAGTCTCTCTGC |
| 88 | >SLC6A1::3:10992186-11039247; startsite = 11005822; maxEnt = 7.69(+) | GGTTCGATGTTCCTCATCCTGCAGCAGACGTCTCTGCGGGCACCCACCAG |
| 89 | >SLC6A1::3:10992186-11039247; startsite = 11011646; maxEnt = 9.18(+) | TTTTTTTTTTTTTTTTTTGCTCAGGCCAAATAAAACAAGCCCAAGGGCCA |
| 90 | >SLC6A1::3:10992186-11039247; startsite = 11015607; maxEnt = 9.95(+) | CTGCACCCCTGCTGCCCTCTGTAGGAGCTGCCTGCCTGCCCCATCGCTGC |
| 91 | >SLC6A1::3:10992186-11039247; startsite = 11010899; maxEnt = 8.83(+) | GTCCTCGATTCCCTGGCTTTTCAGGGCTCCCCACTCACTCCATGGCGGGG |

TABLE 2-continued

Target sequences for 74 cryptic 3' splice sites

| SEQ ID NO. | Target Location | Nucleic acid target sequence |
|---|---|---|
| 92 | >SLC6A1::3:10992186-11039247; startsite = 11016969; maxEnt = 9.36(+) | CAAAAGTCACCTTCCTTCCTCCAGGAGCAAGGGCGGGTGAGAGGAAGAGG |
| 93 | >SLC6A1::3:10992186-11039247; startsite = 11037771; maxEnt = 8.21(+) | GATCTCTTTTTATCGCCATTCCAGGGGCCTCAGGTCCTACTGGGGAAACT |
| 94 | >SLC6A1::3:10992186-11039247; startsite = 10998146; maxEnt = 8.85(+) | TGACTCCTCATCTCTGTCCCCTAGTTTCCCAGCTGATGAAAATCACCTTT |
| 95 | >SLC6A1::3:10992186-11039247; startsite = 11003262; maxEnt = 8.32(+) | AACACTGGCCTGCCTTCCACCCAGGACTTTTTCCCATCACTAACTAAAAA |
| 96 | >SLC6A1::3:10992186-11039247; startsite = 11028119; maxEnt = 7.52(+) | TCCGGTTCTAATCTCCCCTTCAAGGGCAGCCACCATCTCGTTTCTCTGCA |
| 97 | >SLC6A1::3:10992186-11039247; startsite = 11037369; maxEnt = 7.54(+) | TGACTGTTATCTCGGACTTTGCAGGAGTTCCTTTCCCTCCGAACGCTGCT |
| 98 | >SLC6A1::3:10992186-11039247; startsite = 11032986; maxEnt = 9.32(+) | CGAAGTCTCGCTCTTGTTCCCCAGGCTGGAGTACAATGGCACGATCTCGG |
| 99 | >SLC6A1::3:10992186-11039247; startsite = 11037267; maxEnt = 7.93(+) | GGTAGATCATTTTTATCCCGCCAGGGAGTGTGATGCAGGAAGACCACATG |
| 100 | >SLC6A1::3:10992186-11039247; startsite = 11018437; maxEnt = 7.6(+) | AGTCCTGGCCCCCTGGCTTGTCAGATGTACATGACCTTCAGCAAGTCACT |
| 101 | >SLC6A1::3:10992186-11039247; startsite = 11001422; maxEnt = 8.11(+) | TCTCTACTTCCATCCTTCCTACAGCCTTGTCAGAATGGGATACTTCCCTG |
| 102 | >SLC6A1::3:10992186-11039247; startsite = 11035701; maxEnt = 8.47(+) | TGGCCCATCTTCCTCCAACCTCAGATGAAGAAACTGGGGAACCACAGGGG |
| 103 | >SLC6A1::3:10992186-11039247; startsite = 11026090; maxEnt = 8.54(+) | TCTTCTGGCTCTGCCCTCCTCTAGCTTGCTCTTAGGGCCTGTGCATCTGG |
| 104 | >SLC6A1::3:10992186-11039247; startsite = 10997049; maxEnt = 7.66(+) | CCTAGATTTTAAATTCATTTGCAGCTAGTGCTGATGTCATGCACTCAGCC |
| 105 | >SLC6A1::3:10992186-11039247; startsite = 11015791; maxEnt = 7.83(+) | AGTGGAGTTCTCTCTCTTAACCAGGTTGGCGAAAAGCACTCTTGCAGCGA |
| 106 | >SLC6A1::3:10992186-11039247; startsite = 11000356; maxEnt = 8.27(+) | GGATGCTGTTCCTGCCCTTTGAAGATCCACTTGCATTGAAAACCGTAGAT |
| 107 | >SLC6A1::3:10992186-11039247; startsite = 11008549; maxEnt = 8.67(+) | CTTCCATTTATTCATCTGTCCTAGGACAGTGAGGCTAGGCAAACTCATCT |
| 108 | >SLC6A1::3:10992186-11039247; startsite = 11034251; maxEnt = 8.07(+) | CTCACCCTTGCTCTGCTTTTGAAGCTGGGGAACTTGGAGGAAGGGGTTCC |

TABLE 3

Sequences and chemical modifications of selected steric blocker antisense oligonucleotides targeting cryptic splice sites within SLC6A1 introns (showing compounds that activate the expression of SLC6A1 mRNA in KNS60 neuroblastoma cells.)

| Oligo Name | Oligo Sequence | Molecular Weight (Da) | Target Site | Percent Activation |
|---|---|---|---|---|
| SLCss0603 | TCTTGCAGACTATTCTAAAG (SEQ ID NO: 110) | 7933.92 | Intron 1: 11004094-11004117 | 102.81 |
| SLCss0701 | AGGGTGGGCACCCGGACCTG (SEQ ID NO: 111) | 8054.98 | Intron 1: 11005196-11005219 | 120.84 |
| SLCss0801 | GGAAGACCTGGGCCCCGTTC (SEQ ID NO: 112) | 8003.97 | Intron 1: 11006348-11006371 | 209.24 |
| SLCss0802 | TGGGCCCCGTTCTTGCATAG (SEQ ID NO: 113) | 7970.93 | Intron 1: 11006348-11006371 | 136.17 |
| SLCss0803 | TTGCATAGGTGACAGTGCAG (SEQ ID NO: 114) | 8025.94 | Intron 1: 11006348-11006371 | 123.55 |
| SLCss0901 | TGATCATCATTCTTATTACA (SEQ ID NO: 115) | 7883.89 | Intron 1: 11006831-11006840 | 138.59 |
| SLCss1001 | GCTTCTGCAAATTCCCTCTC (SEQ ID NO: 116) | 7877.93 | Intron 1: 11009358-11009367 | 180.25 |
| SLCss1002 | AATTCCCTCTCAGGTACGTT (SEQ ID NO: 117) | 7913.92 | Intron 1: 11009358-11009367 | 228.55 |
| SLCss1101 | GTTTAAAAATCAGCTTCTCG (SEQ ID NO: 118) | 7933.92 | Intron 1: 11010251-11010274 | 114.56 |

TABLE 3-continued

Sequences and chemical modifications of selected steric blocker antisense oligonucleotides targeting cryptic splice sites within SLC6A1 introns (showing compounds that activate the expression of SLC6A1 mRNA in KNS60 neuroblastoma cells.)

| Oligo Name | Oligo Sequence | Molecular Weight (Da) | Target Site | Percent Activation |
|---|---|---|---|---|
| SLCss1301 | TCTGGCTGTATTAATGCGTT (SEQ ID NO: 119) | 7957.89 | Intron 1: 11012180-11012203 | 101.13 |
| SLCss1302 | TATTAATGCGTTTCTTCTAG (SEQ ID NO: 120) | 7916.88 | Intron 1: 11012180-11012203 | 257.13 |
| SLCss1303 | TCTTCTAGGCCTCCCGTGTC (SEQ ID NO: 121) | 7909.92 | Intron 1: 11012180-11012203 | 113.69 |
| SLCss1401 | CCGTGTCTTGTTCTTACACC (SEQ ID NO: 122) | 7894.91 | Intron 1: 11012213-11012236 | 121.89 |
| SLCss1402 | TGTTCTTACACCTCTTGCAG (SEQ ID NO: 123) | 7904.91 | Intron 1: 11012213-11012236 | 160.77 |
| SLCss1403 | TCTTGCAGCACTTATCACAG (SEQ ID NO: 124) | 7922.93 | Intron 1: 11012213-11012236 | 174.72 |
| SLCss1501 | CTTCCGCCTGCTCCACCAGC (SEQ ID NO: 125) | 7890.97 | Intron 1: 11012794-11012803 | 145.5 |
| SLCss1502 | GCTCCACCAGCAGGTAAAGG (SEQ ID NO: 126) | 8006.99 | Intron 1: 11012794-11012803 | 152.72 |
| SLCss1503 | AGGTAAAGGAGGCTGATCAC (SEQ ID NO: 127) | 8043.97 | Intron 1: 11012794-11012803 | 169.43 |

TABLE 4

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 128 | CHD7 | 8 | 60804104 | 5' splice site | TAAAACTCACCTGGCAGAGGCACCGTAAGTCAGCACCTCATGTTAAATAGGGGTGGCTCAAGCATTTATGTTGTTCTAAACCCAGGTTAATGTCTATGATACCTAGTTGCATGAAATAGTTGGTG |
| 129 | CTNNB1 | 3 | 41236710 | 5' splice site | ACAGAGCCAATGGCTTGGAATGAGGTAGGGAAATGTGAGCAGTTATTTATCTGGTAGTTTCCTAGAGCAGGTATGGCAGCTTGTTCTTTCCTCTCAAAACACTTAGTACACATTCATTTGCATTG |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 130 | EHMT1 | 9 | 137653548 | 5' splice site | CTCTTTCTTTTTTTTTTCTTTTG AGACAGAGTTTTGCTCTTGTCG CCCAGGCTGGAGTGCAGTGGT GTGATCTCAGCTCACTGCAACC TCTGCCTCCCAGTTTCAAGCGA TTCTCCTGCCTCAGC |
| 131 | EHMT1 | 9 | 137619050 | 5' splice site | GCCATGGCCGCCGCCGATGCC GAGGTGAGCAGCGGGGCCGGC GGGGGGCGGCGCGGGGGCGGC GGGCAGCGGCGGAGGCGGCGC GGGGGCGAAGAACCGGGCGGG GCGGCGGCAGGCGGCCGGCG |
| 132 | EHMT1 | 9 | 137629024 | 5' splice site | GTTGATGGATTACTTTATCCTA AGGTAAGTGGGCAGTTTGATTT TAAGTTGCTCACTCAGCAAACC AGGTAGGGAATAGTTATTTGCT TTTGTATTTTTTTTTTTTTTTTG AGATGGAGTTTCGC |
| 133 | EHMT1 | 9 | 137720023 | 5' splice site | CCTCCACACCAGGACACAGTC GAGGTGCCGAACCTCCTCCAC ACCAGGGCACAGTCGAGGTGC CGAACCCCCTCCACACCAGGG CACAGTCGAGGTGCCGAACCC CCTCCACACCAGGGCACAGT |
| 134 | EHMT1 | 9 | 137782175 | 5' splice site | GGGCGGGTTCCGGCGTGGCTC GAGGTGGCTGTTTATGTGGAG GATGGTCATTTGTGAGTGCTTG CCAGCCATCGTGACAGTCCTG AGCTGGAGTCTGTGGCTACATC TGAAATCATTAATAAAAC |
| 135 | EHMT1 | 9 | 137818546 | 5' splice site | GCCATGTACCGAGACTGTAGA GAGGCCGACTGAGGGGCGCCG TGTACCGAGACCGTAGAGAGG CCGATTGAGGGGCGCCATGTA CCGAGACCGTAGAGAGGCCGA CTGAGGGGCGCCGTGTACCG |
| 136 | EHMT1 | 9 | 137669456 | 5' splice site | CGCCGCCCACAGCACGTGCAC TCACCTCCACCCAAGACGCCCC CCACAGCACGTGCACTGGACT CCTCCCAAGACGCCCCGCACA GCACGTGCACTCGACTCCTCCC AAGACGCCCCGCACAGCA |
| 137 | EHMT1 | 9 | 137669567 | 5' splice site | CGCCCCGCACAGCACGTGCAC TCACCGACTCCACCCACTGTCT ACCCAGGGCGCAGCCGCTCCA GCAGCTCTTCCCTGGCCCCTCC CCCACCTTCACTTTTTGCTCTCT TCGGAGCATTCATTGC |
| 138 | EHMT1 | 9 | 137721201 | 5' splice site | CCCCTCCCAGACTTCTCACACT CACCCCTCCCAGACTTCTCACA CTCACCCCTCCCAGACTTCTCA CACTCGCCCCCTCCCAGACTTC TCACACTCACCCCTCCCAGACT TCTCACACTCACCCC |
| 139 | EHMT1 | 9 | 137721274 | 5' splice site | CCCCTCCCAGACTTCTCACACT CACCCCTCCCAGACTTCTCACA CTCACCCCCTCCCAGACTTCTC |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | ACACTCACCCCTCCCAGACTTC TCACACTCACCCCCTCCCCTCT CACCCCCTCCCACGC |
| 140 | EHMT1 | 9 | 137721298 | 5' splice site | CCCCTCCCAGACTTCTCACACT CACCCCCTCCCAGACTTCTCAC ACTCACCCCTCCCAGACTTCTC ACACTCACCCCCTCCCCTCTCA CCCCCTCCCACGCCTCACCCCC TCCCACGCCTCTCAC |
| 141 | EHMT1 | 9 | 137721212 | 5' splice site | CTTCTCACACTCACCCCTCCCA GACTTCTCACACTCACCCCTCC CAGACTTCTCACACTCGCCCCC TCCCAGACTTCTCACACTCACC CCTCCCAGACTTCTCACACTCA CCCCCTCCCAGACTT |
| 142 | EHMT1 | 9 | 137721261 | 5' splice site | TTCTCACACTCGCCCCCTCCCA GACTTCTCACACTCACCCCTCC CAGACTTCTCACACTCACCCCC TCCCAGACTTCTCACACTCACC CCTCCCAGACTTCTCACACTCA CCCCCTCCCCTCTCA |
| 143 | EHMT1 | 9 | 137721310 | 5' splice site | TTCTCACACTCACCCCCTCCCA GACTTCTCACACTCACCCCTCC CAGACTTCTCACACTCACCCCC TCCCCTCTCACCCCCTCCCACG CCTCACCCCCTCCCACGCCTCT CACCCCCTCCCACGC |
| 144 | EHMT1 | 9 | 137721334 | 5' splice site | CTTCTCACACTCACCCCTCCCA GACTTCTCACACTCACCCCCTC CCCTCTCACCCCCTCCCACGCC TCACCCCCTCCCACGCCTCTCA CCCCCTCCCACGCCTCTCACCC TCTCCCACGCCTCTC |
| 145 | EHMT1 | 9 | 137721323 | 5' splice site | CCCCTCCCAGACTTCTCACACT CACCCCTCCCAGACTTCTCACA CTCACCCCCTCCCCTCTCACCC CCTCCCACGCCTCACCCCCTCC CACGCCTCTCACCCCCTCCCAC GCCTCTCACCCTCTC |
| 146 | EHMT1 | 9 | 137818817 | 5' splice site | GTACCGAGACCGTAGAGAGGC CGACTGAGGGGCGCCATGTAC CGAGACCGTAGAGAGGCCGAC TGAGGGGCGCCGTGTACCGAG ACCGTAGAGAGGCCGACTGAG GGGCGCCGTGTACCGAGACC |
| 147 | EHMT1 | 9 | 137819425 | 5' splice site | GTACCGAGACCGTAGAGAGGC CGACTGAGGGGCGCCATGTAC CGAGACCGTAGAGAGGCCGAC TGAGGGGCGCCGTGTACCGAG ACCGTAGAGAGGCCGACTTAG GGGCGCCGTGTACCGAGACC |
| 148 | EHMT1 | 9 | 137721374 | 5' splice site | CCTCCCCTCTCACCCCCTCCCA CGCCTCACCCCCTCCCACGCCT CTCACCCCCTCCCACGCCTCTC ACCCTCTCCCACGCCTCTCACC CTCTCCCACGCCTCTCACCCTC TCCCACGCCTCTCAC |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 149 | GRN | 17 | 44352619 | 5' splice site | GGCTGGGTATGGCCAGGGACC AGGTCCCACCTCGTCCAACCCT CTCGCCCCCCTCTGACCATCCA GGGCGTCTGTTGTGCTGATCGG CGCCACTGCTGTCCTGCTGGCT TCCGCTGCGCAGCCAG |
| 150 | GRN | 17 | 44349177 | 5' splice site | TGCAGGCAGACCATGTGGACC CTGGTGAGCTGGGTGGCCTTA ACAGCAGGGCTGGTGGCTGGA ACGCGGTGCCCAGATGGTCAG TTCTGCCCTGTGGCCTGCTGCC TGGACCCCGGAGGAGCCAG |
| 151 | GRN | 17 | 44351461 | 5' splice site | TGGGGCTGCTGCCCTTTTACCC AGGTACCCAGGGGTGGCGGGT GGGTGGGCTGAGCACAGTGTG GCAGGCAGCCGGGCCCCAGTG CCCACCTGCCCTTCTTCATCTG CCCTAGGCTGTGTGCTGT |
| 152 | HTR7 | 10 | 90810092 | 5' splice site | GGTATTGACGGCCAGGTTTCTA AACCTCTTAAAACTCCCCAACT CTGGTGCCACCTTAGACAATAC TCTTTTAAGCACTCCTTTTTAG TTATCCCCACCTGCCCAGTTCC CTTATTAGGCCAAGA |
| 153 | JAK2 | 9 | 5055789 | 5' splice site | CATAAGCAAGATGGTAAAAAT CTGGTAAGTTTGCTTTATGATT GAATAATGGTTTCATTTTATAG TTCTCAGAAATGTGTATTTTAG AATCTTAGTACCAAAATTATTT TCTGGTAGGAATTTTG |
| 154 | KCNQ4 | 1 | 40802257 | 5' splice site | TGTGAGGTGGAAGGGCGAGGC CGAGGCGGCGGTGGCGTCGCG TCCCCCCTCTCCGCCCCTGGCC TCGGGGACGCGGCGGCACCTT CACACTTTCCGCTTGGCCCGCT GCTCGCCTTTCAGGCCGC |
| 155 | KCNQ4 | 1 | 40822403 | 5' splice site | TGACAGTATCCTCCCATCCTTC AGGTAGGTCCTGCTGGGGGTG GGGGTGGGTGGGGGGCTGGCA GCAATGCCCTTTGAGGACAAG TGGCTGAGACTCAACCCTGGA GGGTGGAAAGGGGGTGATG |
| 156 | LEPR | 1 | 65425379 | 5' splice site | GGGATGTGCCTTAGAGGATTA TGGGTAAGTTATCATTTCAAAA AGAACTATTCCTCTTTCTGTGT CTTTGTCACTATTAGTATGGGT GTTAGAGAGTTCGGTCAATTTA GCACCAAGTTCTAACC |
| 157 | LEPR | 1 | 65616235 | 5' splice site | GCCTATGAGCAAAGGTAAGAA GAGGTACAGAGTGGTAATCCA TTGCCTCTTTTAATATTTAACTT TTGCAAACTCTCCTATTTTAAA TTATCTTTCAAGCAGCCTGCAA TTCTCTGCATCTGAAA |
| 158 | LEPR | 1 | 65525690 | 5' splice site | TCCTCTCCTGAGAGTTGCCCCG CACCTTGGGCGAGGAGTTCGG AGCGGCCCCATCGCAGAGCCC ACGGCCAGCCGAGCGCGCGCG |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | ACGCAGGTGCCCGAGCCCCGG CGCCGCCGCCATCTCTGCC |
| 159 | LIPC | 15 | 58520257 | 5' splice site | AAACCTAAAAGCAATTTTGTTT GGGTTGAAACAAGGTGGGCGG GCAGTCAGGAACCCACCCTTTT AACTTCTGTGTCCTCTGCCATC TCCTGTAGCAGCCCCCAAAGT AGTTCCACAAGATCCTT |
| 160 | MBD5 | 2 | 148089610 | 5' splice site | GAATGATCTTTGGGTCAACAAT GAAAACAAGATGGAAGTAAAA AATTATCTGAACTGAATGATA ATAGTGACACAACTTATCAAA ACCTCTGGGACACAGGAAAAA TGGTGCTAAGAGGAAAGTT |
| 161 | MBD5 | 2 | 148021047 | 5' splice site | ACCCGTCAGAGAGGGACATGC GCAGTGAGTGCCTCCCGTCTCT TCTACCCGAACCCCCCCTCCCC CCCAAGCAGAGAGACCCCAGC AGCAGCAGCAGCTGATGATGA AGAGAGAGGCAGTGGCAG |
| 162 | MBD5 | 2 | 148458872 | 5' splice site | TCAAAATGGAGTGCTTTATGTC AGGTAAGTTCTTATTATTACCT GTGGTACCTGCAAAGTTGTACT CCAAAGACTAAGGAGAGAACC AAGCATGGTGACTGATGGCAC CTCATATAAATGTGAAA |
| 163 | MBD5 | 2 | 148468947 | 5' splice site | TGTTCCACCACAAACCACCCCA AGGCCCACCTCCCCCTCCTCCA CCTTCTTGTGCTCTTCAGAAAA AGCCATTAACATCTGAGAAAG ATCCACTTGGCATTCTTGACCC TATTCCTAGTAAACCA |
| 164 | MNX1 | 7 | 156999923 | 5' splice site | CCCGGGGCGCGCATTGTCCGC ACGGTGTGTACTCGGGGAGGG GCGCCAGGTGCGCGGGCGGAA TGTAGGGTCGGCGCGGGGCCG GGGGGCGGGCCCGGGGCCGGG GGGTCCTCAGGAAGCCTCGG |
| 165 | NFIA | 1 | 61112344 | 5' splice site | TGATAACAAGAAATTAAAATC AAGGTACAGTATCATTTATATG TAGTAGTACAGAGTAACCATG ACTTACTAGGTGTTATGATGAA GGTGTATGTGTGTGTATATGTG TGCATGCATGTAGATAA |
| 166 | NFIA | 1 | 61277586 | 5' splice site | ACATTAAGGACCAGCCAGAAA ATGGTAAGTTTAGCTTGGGACT CTAGCTGCTGCTTTCAGAGTCC ACAGCAGCCAGCAGGCCGACT AAGTGTGAGGATTTGGGGGCC TACCCTATAAGTAGCCCA |
| 167 | NFIA | 1 | 61352568 | 5' splice site | TTTACCCAGCACATCCTCTACG AGGTAATTTTATTGGCAGCTCT TGAAGAAATTATGCTACATGG TTGCACACCTTGATTTTAACTC TGGGCCCACTATGGATTTAGCA ATGCGCCTTTAGTAAT |
| 168 | NMU | 4 | 55607436 | 5' splice site | TATAGATGTATGAAAATCATCT TACCCTTTTAGTATTATCTTTTT |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | CATCTTGTTCCTATTGAAAAGA GATATTGTATATATCATTATAT ATTGTAAAATTTTACTATCTTA TATACAGTAATTTT |
| 169 | NOTCH1 | 9 | 136545725 | 5' splice site | GGCTCGCGGGTGGGTGGGCGC CTACCTCGTGCGGCGAGCGCG GGCAGCAGCGCCAGGCAGAGC AGGGGCGCCAGGAGCGGCGGC ATGCCTCCCCACCGGCTGCCCT CTGCGCCCGGGCGGCGGCC |
| 170 | NOTCH1 | 9 | 136535683 | 5' splice site | GTGCAGGGTGGGTCGGGGGGA GCACTCAGGATCCCTCCCAGG GGCAATGGGTGCAGGGTGGGA GTGGGTGGAGGGGGGAGCACT CAGGATCCCTCCCGGGGCAAT GAGTGCAGGGTGGGTGGAGA |
| 171 | NOTCH1 | 9 | 136542751 | 5' splice site | GCTGGGGTTGTCAAGGGAATG GGACCTTCTGCAGTTGGAATG AGGGCGCGCAGACTGGCTGGG GAGCCATTTCTTCATCTGTAGC TCCTGGGGGGCGGAGGGAACT CTTTTTCCAGACACCAAAC |
| 172 | NSD1 | 5 | 177254432 | 5' splice site | TTTTTAATCTGCGACAGAGTCT CACTCTGTCACCCAGGCCGGA GTGCAGTGGCGTGATCTCAGCT AACTGCAACCTCCACCTCCTGG GTTCAAGCGATTCTTGTGCCTC AGTCTCCCGAGTAGCA |
| 173 | NSD1 | 5 | 177147361 | 5' splice site | GCTCAAGCAATCCGCCTGCCTT GGCCTCCCAAATGGCTGGGAT TACAGGCAGGAGCCACCATGC CTGGCCTAGCCCCTCCATCTCT AGCCTTTGTCAGTTACTAAACT TTTTTTCCTGAAGTTTT |
| 174 | PAX6 | 11 | 31812498 | 5' splice site | GTTGCCAGAAAACCGGGGAGG AAAGTAAGTAAATGGCTTTTCT CTTCTGACCACACACCAGAAG TCCATTTGTTGAATGCCGCACG ATTAGGACACACCTCAGTACA CTCCAAAGGCGCCCCTCG |
| 175 | PHIP | 6 | 78958474 | 5' splice site | AATTACATATGAAAAGATAAC TTACTTTATAAAATGTAGAAGA AGATCAGTCACGAATTTAGCA GATTTCACAATAGGGCTTCCAG GCTCATTAAATGTTCGTGTATT ATGCTCTATATATCGAA |
| 176 | PKD1 | 16 | 2105000 | 5' splice site | GGGGAGGAGGGGAAGGGCTA GGGGAGGGGAGGAGGGGAGG GGCTAGGGGAGGGAAGGGGG AGGGGAGGGGAGGGGAGAGT GGAGGGCACAGAGCAGCATCT TCTTAGTCCCTCCCCACATCTG GG |
| 177 | PYY | 17 | 43975248 | 5' splice site | CTTTCCTTTCCACATACTTACA AACCTAGGGGTGGTGGAAAGG GTATGGATTCCGGAGTCAGAT GTTCTGGGTTTGAATCCCACTC GCATTTCTTAGCTGTGTGACTT TGAGAGAGTTTGCTTGG |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 178 | RAI1 | 17 | 17787512 | 5' splice site | TGATCAGTACAGAACTGATAA TAGGTGAGCTCCTCCCGGCAG CCTTCCCTGGGGGGCCTAGGA ATGCCTGCAGCTGCTGTGGAAT CCCATGTTGCTCCCCCACACCT CACAGTGGAGGTGGGACT |
| 179 | RBPJ | 4 | 26326229 | 5' splice site | GTATTTGACTTTGGTTCTGTAA GGAGTAATTGCTGAAGTACCC AGAGGAATTGATATTTTCAGCC ACAAGCAATCTCATAGCCCCT GAGAACATTATAGTAAGGCTC TTAGGCAAAAGTTTTTTT |
| 180 | RBPJ | 4 | 26320816 | 5' splice site | GCCTGCGCATGCTCCATCGCCT GGGTAGGTTTCCAGGGAAGGC AGCGAGCAGGATCCCCTACTC TGCGGGCGGCGCGAGGCGTCT GGCTCTTCGCGGCGGCGGCGA GGGGAAAGGGAGCGCGGGG |
| 181 | RBPJ | 4 | 26321049 | 5' splice site | GAAGATGGCGCCTGTTGTGAC AGGGTAAGTCTGAGGGAATCG GAGCGCCGGGAACCGGGAAAG TTGCGGGCGTCTGGCAGCTCAC GGCGGGCAGCGGGTTCGGGGG CCGCGGCGCGCTTGGCGTT |
| 182 | RBPJ | 4 | 26367901 | 5' splice site | ACAGTGAAAAGATGAAGACTT CTGGTAAATTGTTTCACAGCAG TGGAATTTGTACATTAGTTTTC TACACTTGGGAGTTGAAAAAT GGAAGAATTATTTGCCAAAAG AGGAGGACAAAAGATAAT |
| 183 | RPS14 | 5 | 150445608 | 5' splice site | GCATTAGCTAGAGGGGGGCAC TTACCAATCCGCCCGATCTTCA TACCCGAGCGGGCAAGGGCTC TGAGGGCCGACTGGGCCCCAG GTCCAGGGGTCTTGGTCCTAGA AAATGAAGGTTTAAGTTA |
| 184 | RPS14 | 5 | 150445629 | 5' splice site | TTACCAATCCGCCCGATCTTCA TACCCGAGCGGGCAAGGGCTC TGAGGGCCGACTGGGCCCCAG GTCCAGGGGTCTTGGTCCTAGA AAATGAAGGTTTAAGTTAAGA AGAGCCTTTGGCCAAGTC |
| 185 | RUNX2 | 6 | 45328457 | 5' splice site | CTACCAGCCACCGAGACCAAC AGAGTCAGTGAGTGCTCTCTA ACCACAGTCTATGCAGTAATA GTAGGTCCTTCAAATATTTGCT CATTCTCTTTTTGTTTTGTTTCT TTGCTTTTCACATGTTA |
| 186 | RUNX2 | 6 | 45438052 | 5' splice site | TAGATGGACCTCGGGAACCCA GAAGTAAGTACTCCCCTTTTTA TTGAAGAAAGTAATAGAGTTT CCAGAGACCCTATGAGGAATT TATTCCAAATGAGTTAGTGTCA CTTTCATGTCCATAGTGT |
| 187 | RUNX2 | 6 | 45492963 | 5' splice site | GAGGTGGACTAGAATAGAGGG AAAGTAAGTCAAAACAAAATG TGTAATAAGCCCTCAACATGG ATCTTTTTTATGGTTAGATTTTT |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | GTTTATAGTAGTTAGGCTCGAATGTTCTTAATGGTCTCA |
| 188 | RUNX2 | 6 | 45377503 | 5' splice site | CCAGCCCCCCTCACCCCACGCCCACCCGCCAAAAGGGAGGAGTCGAGAGGCAACTCCACGCTCGGCAGCGGAACCAGGGCGCTGCGCCCGGCCAGCGCCTCCCACAGCCGCCCTCCCTTCAACAC |
| 189 | RUNX2 | 6 | 45421844 | 5' splice site | CCGAGATCCGCTGCCCACGACTTACCTCTTGGCACCTTGAAGCGCGAGAGACAGGGGAGCTTTGCAAATTGCAGGAGGGAGTGGATGCAAAGAGGTGGCTGTGAGAGGGCGAGAAGAAAAGAAGG |
| 190 | SETBP1 | 18 | 45063890 | 5' splice site | TTGGGAAAGCAAAGCAGGGAGACACCTTCAGAAGAAGCTTGTCTGAGCTTCACCGCAGCTCCCACCACGCGGCGCTTCAGTACGGCTGGATCCTCCGCAGGCGAGCGGAAGGCCCCCAGGAGGAG |
| 191 | SETBP1 | 18 | 45063576 | 5' splice site | CGAGGCGGAAAGAGGAAACACAAACCGCAGGCCCCCGCTCAGCCCCCACAGCAGTCGCCCCCGCAGCAGCCCCTTCCCCAGGAAGAGGAGGTGAAAGCCAAAAGGCAGAGGAAGTCCCGAGGGAG |
| 192 | SETD5 | 3 | 9431826 | 5' splice site | CATGCAACTTTCCTTTTTCCTGTCCCCCTCCCACCAAAAAAAAATCCATTCCTAATAAACAGCTATCATGTTTCACTCCATGTGTTCAGTGGTACAAAACCTATATAAAATATGTACAGCTCTTT |
| 193 | SETD5 | 3 | 9446005 | 5' splice site | TTTTTTTTACTAACAATCTGGTTTCCGCTGGGCGCGGTGGCTCACGCCTGTAATCCCAGCACTTTGGGAGGGCGAGGTGGGCGGATCACGAGGTCAGGAGATCGAGACCATCCTCGCTAACACGG |
| 194 | SETD5 | 3 | 9426133 | 5' splice site | AGGCTTAGAAGATGTACTGCCAAGGTCTCTGTTTGGATATACTGTTAGGGAAAGGAAACATACATGTGTAAGACTGGCCTAAAGGCAAAAAAGTTCATCAGTCCCTTTTTTTTTTTTTTTTTTT |
| 195 | SETD5 | 3 | 9443418 | 5' splice site | ATTTGATTATGAGTATAGTAACTGGTAAGACCTCAGAAACCTTTCCTAACAGGAATATCCATGTCTTACATATTAAGCTATTCACTCTATTTAAAGTCTGCTCTTGTTTCTTGCCTTTTCCTTTG |
| 196 | SETD5 | 3 | 9445741 | 5' splice site | GAGAACCTAGCTCATAGCAGGAGGGTGAGTACTGTCTGACATTACTTTGCTCCTTCTCATTCCTGCTACCTCCATCATGTGAACCTCTTCTGTTCTCTTGACTTTGTATCATCTCATTGATTTGA |
| 197 | SETD5 | 3 | 9475157 | 5' splice site | AGCCCTTCCAGATACAGCTACCAGGTGAGATGAGAAATTGCTG |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | GTCTCTAGCCATAGGAGTGTGT TCTGGGTCCCAAATTGTCCTGG TCATCCTTTGCCATTGAGATGC TGTCTTTGCATATAGT |
| 198 | SHANK3 | 22 | 50706153 | 5' splice site | TGACAGCTGAGCTCGAGGAAC TTGGTGAGTGGCGGGGGTGGC GGTGGAGGTGGACGCAGGTGG ACGGTCCATGATGGGCAGACA GGGCCGGGAGACACAGGTGGT ACGGGAGGGCAGGCGGTCCA |
| 199 | SYNGAP1 | 6 | 33437439 | 5' splice site | TGCTGGGATTACAGGAATGAG ATACCATGGCTGGCCTCTTCTT AGTTTGATTACATTTGCAGGGA TCCTGTTTCCAAATAAGATCAC ATTCACAGGTTCAGGGTAGAC ATGAGTTTTGGTGGGAT |
| 200 | TBX1 | 22 | 19762274 | 5' splice site | CCGGGAGCCCACGTCCCGCAG CACCCTCCAGCCTGCAGAGGC TTCGGGTGGGGGAGGGAGCGG GCCTGTCCTAGAGGCTGGCTCC TGGCATCTGTCTTCTGCCCACC GCCTGCAGGGAGTTGCTT |
| 201 | TBX1 | 22 | 19765917 | 5' splice site | CGCCCGCAGGCCCCGGAACCA CCGGCCCGGCGCACTGCCGCT CATGAGCGCCTTCGCGCGCTCG CGGAACCCCGTGGCTTCCCCG ACGCAGCCCAGCGGCACGGAG AAAGGTAGGGCCGGGGTCG |
| 202 | TBX1 | 22 | 19766926 | 5' splice site | ACAGCCCCGAAGTTCGCCGGG CCCGGCCACCCTGCCCCAAGG GCAAGCAAGGAATACGTTCCC CCAGCCCCAGGGGCCACCGCG GCTCTCCCCTTCCCCAGCCTCG AAGCCATGGGGGCCCCCTC |
| 203 | TBX1 | 22 | 19765114 | 5' splice site | GTCACTGCCTACCAGAACCATC GGGTGAGGGCCTGTGGGGAGG ACCTGAGCGGATTCAACGCCT CTGGAAAAGCGGGTGTAATTT TCAGTTGCCGTTTGGGGACAGT GGGTCCGCTTAGACCTGC |
| 204 | TCF4 | 18 | 55310455 | 5' splice site | CTAGCTCCAAAATGTGGCACCT AAGGAGTGAGGTCTAGAAGTT GGCAGATGTAAGACTCAGCCA CCAGATCCTGCCACCTTCCTCC ACAGGGTGCTACAGAAGGCAA CTGAGGTTTCAAAATCAC |
| 205 | TCF4 | 18 | 55546093 | 5' splice site | TCATGCCTGTAAATCTCAGCAC TTTGGGAGGCCGAGGCAGGAG AATGATTTGAGCCCAGGAGTA AGAGACCAGCCTCCGTAACAA AGTGAGACCTCGTCTCCACAA AAAAAATTTTTTAAATCAG |
| 206 | TCF4 | 18 | 55365219 | 5' splice site | GTGTGTGTGTGTGTGTATATAT ATGTGTGTGTGTGTGTGTATAT ATATGTGTGTGTATATATATAT ATATATACACACACACACACA TATATATATGATGGCTGGGCTT AGCAGATGTGTAGATT |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 207 | TCF4 | 18 | 55365243 | 5' splice site | GTGTGTGTGTGTGTGTATATAT ATGTGTGTGTATATATATATAT ATATACACACACACACACATA TATATATGATGGCTGGGCTTAG CAGATGTGTAGATTCTCCTATT GCTGGGTCCCACTTTT |
| 208 | TCF4 | 18 | 55589976 | 5' splice site | GCGGAGGCGGGTGGCTGTTCT CGGGTAGGCGTCGCGCGTGGG GCGGCACTGTGGGAGTTCCCG AGGCCGAGGTCGTTCGCAGGC CCCATTTCCCTGCGCTCTTATT CGTGTTGCCGCTTCTTGGC |
| 209 | TCF4 | 18 | 55585279 | 5' splice site | AACACTAAGAAAAGAATTTAC ATACTTGAGCCAGTAAAATGT CCACTTGCCAAAGAAGTTGGT CCATTTTTCCCACTGCTCACAG GAGGTGAAAACATCTAAAAGA AACAAAGAAATATTACAGT |
| 210 | TGIF1 | 18 | 3456747 | 5' splice site | AAGCTAATAACTAGCTATTTAG AGAACACAGAAACACTTGACA GTCATCTATCAGATAGCATTTC CTTTAATGCCTAAAAGAACCTT CCTTTATGCAACAGACATTAAA AGGAGGTTAAACCTTA |
| 211 | TGIF1 | 18 | 3453560 | 5' splice site | ATTAGCCGGGCGTGGTGGCTTT TGCCTGTAATCCCAGCTATTCG GGAGGCTGAGGCAAGAGAATC GCTTGAACCCTGGAGGCGGAG GCTGCGGTGAGCCGAGGTTGC GGCATTGCACTCCAGCCT |
| 212 | WDTC1 | 1 | 27234952 | 5' splice site | CGGTCGGGGGAAGAGACCTGA CAGGTACGGGTCACCGCCGCC CCCTGCCCTCCGCGGGCGCCG AGGCGGGGACCGGCTCCCGCA GCCCCGGTGAACGGGCCGCCC GCTCTGGGCCGGCTCCAGCC |
| 213 | CHD7 | 8 | 60808216 | 3' splice site | TGCCTGAAATTTTCTTTTGTTG CAGAAGGAATCTGGAGAGGAG GTAGAAATTGAGGAATTCTAT GTGAAATACAAAAACTTGTAA GTAAATTGTGATTCTGTTTTTA ATGGGGGGCTATATTTTC |
| 214 | CTNNB1 | 3 | 41237599 | 3' splice site | GTTTTCACTGTCTTCTCTGTCTT AGTTAATGTCAGCTTTGTCTGT CCAGCTGCTCAGGCTAAAACTT TTCTTTCATATAACACATCCTA TCAGCAGCTCCTGTTTGTGGGT AGGCATTTTGCCTT |
| 215 | EHMT1 | 9 | 137654342 | 3' splice site | TACACCACTGCACTCCAGCCTG GGCGACAGAGCGAGGAGACCC CACCCCCCACCCCTTACCACCT CCCCCCCACCAAAAAAAAAAG AGAAAAATTAATTGACCATAA ATATGTGAGTCTGTTTCT |
| 216 | EHMT1 | 9 | 137669068 | 3' splice site | CCCCCGCTAATTTTTCTATTTTT AGTACAGACGGGGTTTCACCA TGTTGGGCAAGATCGTCTTGAA |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | CTCCTGATCTCAGGTGATCCGC CTGCCTAGGCCTCTCAAAGTGC TGAGATTACAGGCGT |
| 217 | EHMT1 | 9 | 137688817 | 3' splice site | TGTCATATCACTGCATGGACAG CAGGTGTGTGAAGGTTTGTGTC ATCCACCGAGTCTGCCCTGACT GAACTGGTCACATCCGCGGAT GGCCGTGGTGACCTCTTCTGAG CTCTGATCTGCTATTG |
| 218 | EHMT1 | 9 | 137710966 | 3' splice site | GACGGCTGTTGTTTCTCTCTAA CAGGCAGTTCCGGCGAGGGGG GAGCCTCAGCAGGATTGCTGT GTGAAAACCGAGCTGCTGGGA GAAGGTGAGGGCGGTGTGCAC CGAGGGACAGGAGCAGCGC |
| 219 | EHMT1 | 9 | 137720057 | 3' splice site | TCCTCCACACCAGGGCACAGT CGAGGTGCCGAACCCCCTCCA CACCAGGGCACAGTCGAGGTG CCGAACCCCCTCCACACCAGG GCACAGTCGAGGTGCCGAACC CCCTCCACACCAGGACACAG |
| 220 | EHMT1 | 9 | 137720092 | 3' splice site | CCCTCCACACCAGGGCACAGT CGAGGTGCCGAACCCCCTCCA CACCAGGGCACAGTCGAGGTG CCGAACCCCCTCCACACCAGG ACACAGTCGAGGTGCCGAACC CCCTTCACACCAGGGCACAG |
| 221 | EHMT1 | 9 | 137782290 | 3' splice site | TTAATAAAACTGTGTTTGTTCA CAGTGGACGGAATTGACCCCA ACTTCAAAATGGAGCACCAGA ATAAGCGCTCTCCACTGCACGC CGCGGCAGAGGCTGGACACGT GGACATCTGCCACATGCT |
| 222 | EHMT1 | 9 | 137818583 | 3' splice site | CGCCGTGTACCGAGACCGTAG AGAGGCCGATTGAGGGGCGCC ATGTACCGAGACCGTAGAGAG GCCGACTGAGGGGCGCCGTGT ACCGAGACCGTAGAGAGGCCG ACTGAGGGGCGCCGTGTACC |
| 223 | EHMT1 | 9 | 137669420 | 3' splice site | CCCCACAGCACGTGCACTCCA CGACTGCACCCAAGACGCCGC CCACAGCACGTGCACTCACCTC CACCCAAGACGCCCCCCACAG CACGTGCACTGGACTCCTCCCA AGACGCCCCGCACAGCAC |
| 224 | EHMT1 | 9 | 137669457 | 3' splice site | GCCGCCCACAGCACGTGCACT CACCTCCACCCAAGACGCCCC CCACAGCACGTGCACTGGACT CCTCCCAAGACGCCCCGCACA GCACGTGCACTCGACTCCTCCC AAGACGCCCCGCACAGCAC |
| 225 | EHMT1 | 9 | 137721155 | 3' splice site | CTCCCAGACTTCTCACACTCAC CCCTCCCAGACTTCTCACACTC ACCCCCTCCCAGACTTCTCACA CTCACCCCTCCCAGACTTCTCA CACTCACCCCTCCCAGACTTCT CACACTCGCCCCCTC |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 226 | EHMT1 | 9 | 137721180 | 3' splice site | TCCCAGACTTCTCACACTCACC CCCTCCCAGACTTCTCACACTC ACCCCTCCCAGACTTCTCACAC TCACCCCTCCCAGACTTCTCAC ACTCGCCCCCTCCCAGACTTCT CACACTCACCCCTCC |
| 227 | EHMT1 | 9 | 137721188 | 3' splice site | TTCTCACACTCACCCCCTCCCA GACTTCTCACACTCACCCCTCC CAGACTTCTCACACTCACCCCT CCCAGACTTCTCACACTCGCCC CCTCCCAGACTTCTCACACTCA CCCCTCCCAGACTTC |
| 228 | EHMT1 | 9 | 137721204 | 3' splice site | CTCCCAGACTTCTCACACTCAC CCCTCCCAGACTTCTCACACTC ACCCCTCCCAGACTTCTCACAC TCGCCCCCTCCCAGACTTCTCA CACTCACCCCTCCCAGACTTCT CACACTCACCCCCTC |
| 229 | EHMT1 | 9 | 137721253 | 3' splice site | TCCCAGACTTCTCACACTCGCC CCCTCCCAGACTTCTCACACTC ACCCCTCCCAGACTTCTCACAC TCACCCCCTCCCAGACTTCTCA CACTCACCCCTCCCAGACTTCT CACACTCACCCCCTC |
| 230 | EHMT1 | 9 | 137721277 | 3' splice site | CTCCCAGACTTCTCACACTCAC CCCTCCCAGACTTCTCACACTC ACCCCCTCCCAGACTTCTCACA CTCACCCCTCCCAGACTTCTCA CACTCACCCCCTCCCCTCTCAC CCCCTCCCACGCCTC |
| 231 | EHMT1 | 9 | 137721310 | 3' splice site | TTCTCACACTCACCCCCTCCCA GACTTCTCACACTCACCCCTCC CAGACTTCTCACACTCACCCCC TCCCCTCTCACCCCCTCCCACG CCTCACCCCCTCCCACGCCTCT CACCCCCTCCCACGC |
| 232 | EHMT1 | 9 | 137818779 | 3' splice site | GTACCGAGACTGTAGAGAGGC CGACTTAGGGGCGCCGTGTAC CGAGACCGTAGAGAGGCCGAC TGAGGGGCGCCATGTACCGAG ACCGTAGAGAGGCCGACTGAG GGGCGCCGTGTACCGAGACC |
| 233 | EHMT1 | 9 | 137721294 | 3' splice site | CTCACCCCTCCCAGACTTCTCA CACTCACCCCCTCCCAGACTTC TCACACTCACCCCTCCCAGACT TCTCACACTCACCCCCTCCCCT CTCACCCCCTCCCACGCCTCAC CCCCTCCCACGCCTC |
| 234 | GRN | 17 | 44352873 | 3' splice site | CCTCTGCTCAGGCCTCCCTAGC ACCTCCCCCTAACCAAATTCTC CCTGGACCCCATTCTGAGCTCC CCATCACCATGGGAGGTGGGG CCTCAATCTAAGGCCTTCCCTG TCAGAAGGGGGTTGTG |
| 235 | GRN | 17 | 44350227 | 3' splice site | GTATCCTGGGTCATCTTGTCCA CAGGTAACAACTCCGTGGGTG CCATCCAGTGCCCTGATAGTCA GTTCGAATGCCCGGACTTCTCC |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | ACGTGCTGTGTTATGGTCGATG GCTCCTGGGGGTGCTG |
| 236 | GRN | 17 | 44352014 | 3' splice site | ACGCCCTTTCCTGCCCACCCCC CAGGCTGTCTGCTGCTCGGACC ACCAGCACTGCTGCCCCCAGG GCTACACGTGTGTAGCTGAGG GGCAGTGTCAGCGAGGAAGCG AGATCGTGGCTGGACTGG |
| 237 | HTR7 | 10 | 90809677 | 3' splice site | AGCGGCCAGGCGTTCCTCCAG AACCTCCTCTGCCAGGAGCTTG CTACAAGTGCCAGAAATCTGG CCACCAGGCCAAGGAATGCCT GCAGCCCAGGATTCCTCCTAA GTCACGTCCCATCTGTGCA |
| 238 | JAK2 | 9 | 5056554 | 3' splice site | ATTCAGCATAGTTTTCTGTTCT TAGATAAAAATATGATAGTAC ACCTACTGCCTAGTAGACTGTG AGCCTTTTGAAGGTAAGGATC ATATTTTTATGTGTGTTTGTAC CCCCTACACCTTGCACA |
| 239 | KCNQ4 | 1 | 40802306 | 3' splice site | TCTCCGCCCCTGGCCTCGGGGA CGCGGCGGCACCTTCACACTTT CCGCTTGGCCCGCTGCTCGCCT TTCAGGCCGCCGCGTTTTCAAT TGTTAATTTGGAAACGGAAAA AGTAGCCGGCCGGGCG |
| 240 | KCNQ4 | 1 | 40826370 | 3' splice site | CATGGAGTGTTTGTTCAAAATG CAGATACCTGGACCTGTCTCCA AGCCCACAGGATCAGAATCTC TGGAGAAGAGACACAGCCTTC TGCATATGTAACATGGTCCCCA GGGGATCCCTATGCAAA |
| 241 | LEPR | 1 | 65493866 | 3' splice site | TTCTAATCTAATGTGCACTCCA CAGGAACCCTATTCTGTCAACA GACCTGGATTCTGATATCAATG AAATAGTGCACATCTTGAAAA CATTTCCACTAATGTAAACAAG AAAGATGAAAGTCAAC |
| 242 | LEPR | 1 | 65617963 | 3' splice site | ATTAATTTCCTTCTTTTCCCCTC AGTAAATATCGTGCAGTCACTC AGTGCTTATCCTTTAAACAGCA GTTGTGTGATTGTTTCCTGGAT ACTATCACCCAGTGATTACAA GCTAATGTATTTTAT |
| 243 | LEPR | 1 | 65515132 | 3' splice site | TGGGTGATGGTTGAGGGAGGG ATGCTGTGGAATGAAGGAATA ACATTCAGGATGGCATAGCAT GAACAAAACCAGGAAGTGAAA ATAAATGCAAAGATGCTCTTA AGTCACTGTGAGTTCTCTGC |
| 244 | LIPC | 15 | 58520979 | 3' splice site | GGGGTCTGGAGGGCTTTAAGA TGAGGGCGAAACAAGGACCAC CCATGATTCCAAAGAATATCC GGAACTTGCTTGTTGTCTGTTG GTGCCTTTCTTTCAGCTCATTC CTAGAGGGCGGACAGAGG |
| 245 | MBD5 | 2 | 148089789 | 3' splice site | AAGGTCAGACCTCAAGGAAGT AGAGAAACAAGAACAAACCAA |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | ATCCAAACCCAACAGAAGAAA AGAAATAACAAAGATCAGAGC AGAACTAAATGAAATTGAAAC ACAAAACAATACAAAAGAAA |
| 246 | MBD5 | 2 | 148021437 | 3' splice site | GAGAAAGAAACCAAAAGCCTC TTAGCAACACAGACCCTTTGCT GCTGCTGTTGCTGCTGCTGCTG CTGTTGCTGCTGCTGCTGCTAC TGCTGCTGCTGCTACTGCTGCT GCTTGGCCCTGGCTGG |
| 247 | MBD5 | 2 | 148468340 | 3' splice site | ATTCTTTTTTTCTCTTTCACATC AGATGCAACTCCAGTAGTACC TTCTCGGGCAGCAACTCCAAG ATCAGTAAGAAATAAGTCTCA TGAAGGAATTACAAATTCTGT AATGCCTGAATGTAAGAA |
| 248 | MBD5 | 2 | 148469445 | 3' splice site | CAAGGTCAACAATAGGGTCCC CAAGGCCATCAATGCCATCAA GCCCTTCTACCAAGTCCGATGG ACATCATCAGTACAAGGATAT CCCTAACCCATTAATTGCTGGA ATAAGTAATGTACTAAAT |
| 249 | MNX1 | 7 | 157005081 | 3' splice site | TTTTCTTTTTCCAAATACTCTGC AGAATGGCGGCTCCAGAGGCG GTTTCAAGTTTCATAAGTCAGG TAACACTGTGGGTTTCCGCCTT CTCGGACGCGGGGAAAGGGGA GACAGGAGGCTTCCCC |
| 250 | MNX1 | 7 | 157006266 | 3' splice site | GCGGCCTGGGGATCACCTTCTT CAGAATGAAAGGAGGGGTGGT TAAGTGCTGATTCTTGGGCCCC ACCCGAAGCTACTGAATCGGC GCTCTGGGCACCTTAGATGAA CCCGTGCGCCCGCCGTCT |
| 251 | NFIA | 1 | 61132694 | 3' splice site | AAACTAAAATCTGTTTCTTTTT CAGGAGGAGTTGGAAGATGAG GAGTAACACAACACTTTAGAT ATACATGTTAAAAACTTATAAC AAATCATAGATCATACTAAAG GATTACCGAAGTTTAGAA |
| 252 | NFIA | 1 | 61310172 | 3' splice site | CTTTGTGTTTTGAAAATCTCTT TAGTGTGCTGGGCCGATGGCC ACATTTTCTGCTGTGTATATGT GATATCAAACTTTAACAAGTCT GTTGCAACAAGGATAAGACAC AGCAGTAGGAAAAGACC |
| 253 | NFIA | 1 | 61383236 | 3' splice site | CTTACCAGTTGATCCTTCTTGC CAGGAATGCCATCTCCAACCA CACTGAAGAAGTCGGAGAAGT CTGGTTTCAGCAGCCCCTCCCC TTCACAGACCTCCTCCCTGGGA ACGGCGTTCACACAGCA |
| 254 | NMU | 4 | 55599182 | 3' splice site | TGCTGACCTTCTTCCATTCCGT GGCTGAAAAATAATAGATTAG AAATAAATCAGTGTAACTAAA GATGCAAGCTAACAGTCATAG AAACAGATTGATGATTTAGAG GAGTGTTTAACGTGCATCA |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 255 | NOTCH1 | 9 | 136523980 | 3' splice site | GGGCCCACGAAGGCCCCGCCA CAGCTGTTGGCAGATGTGCCA GGGCAGTTAGTTCCCACCTGCT TCCCCAGCGCCCCCGCCACTCA GCACCGGGAACCTGTCATGGG CACAGCCGCCTCCCCCCA |
| 256 | NOTCH1 | 9 | 136535634 | 3' splice site | GCAGGGTGGGTGGAGAGGGGA GCACTCAGGATCCCTCCTGGG GCAATGGGTGCAGGGTGGGTC GGGGGGAGCACTCAGGATCCC TCCCAGGGGCAATGGGTGCAG GGTGGGAGTGGGTGGAGGGG |
| 257 | NOTCH1 | 9 | 136542685 | 3' splice site | GTGGGGGCCGGGGAGGGAGGG GGCCTGCTGCCCACAGGCTGG GCAGTCGGCACAGGCAGGAGC CGGGCTGGGGTTGTCAAGGGA ATGGGACCTTCTGCAGTTGGA ATGAGGGCGCGCAGACTGGC |
| 258 | NSD1 | 5 | 177161724 | 3' splice site | TTGTTTTTTGAGATAGAGTCCA GCCTGGAGTGCTGTGGCATGA TCTTGGCACACTTGCAACCTCT GCCTCCTGGGTTCAGGTGATTC TCCTCCTCTAGCCTCCTCCACG CCTGGCTAATATTTGT |
| 259 | NSD1 | 5 | 177146699 | 3' splice site | CTGTATAGGTTAGTATATCCAT GACTCCCGTCAACTTTCTAAAT GTTCGCTGGGTGCAGTGGCTCA TGCCTGTAATCCCAGCACTTTG GGAGGCTGAGGCGGCTGGATC ACCTGAGGTCAGTAGT |
| 260 | PAX6 | 11 | 31812817 | 3' splice site | GTACGCTAGACTCTTCTTGACT TAGGGAAAGTGCTGAAAGTCA GAGCTCATCAATAAAATCTGC GCGACCTGAACTCGCTGCTGA CTGGCCGCGTCGCCGCAGCCC CTGGCAGCCGGGACAGTGA |
| 261 | PHIP | 6 | 78954964 | 3' splice site | TAATCTTCTTCTAGGCTGATGG TCCTGTGATAAAAGTGTTCAAA TATATTAATAAAAGAGCACTT ACACAATAAAATTTGTACTTTT AATGTAGTCTTAGATAATTGGG TAATATACAATAATTC |
| 262 | PKD1 | 16 | 2105069 | 3' splice site | GAGGGGAGAGTGGAGGGCACA GAGCAGCATCTTCTTAGTCCCT CCCCACATCTGGGCCCCTCTTT ACACCCTGGGTCCCCCGAGAG GCACCCTGCGTTCACACAGGA CAGAACGGCTGAGGCTAC |
| 263 | PYY | 17 | 43966533 | 3' splice site | TGAACTTGCCTGAATGAGTTTC CTCTGGAATACAAGGAAGTCA TATGAAATCGCAGTTTAGGCA GTGCATTCAAGAGTACATGGC AGACATCGTTTCGTGTTAATAA CTATATCCTGCCCTTTAC |
| 264 | RAI1 | 17 | 17792932 | 3' splice site | CCTCCCTTCCTTTTTCTTTTCAC AGATAACCAGCCCGAGTCATG CAGTCTTTTCGAGAAAGGTGTG |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | GTTTCCATGGCAAACAACAGA ACTACCAGCAGACCTCGCAGG AAACATCACGCCTAGAG |
| 265 | RBPJ | 4 | 26335132 | 3' splice site | GCTGCCACAGGTAAACGTTAA CTTCAGTAACTTCCTTATTTCC TCCCACTATCAGTTTTTCTTATT TTCTTATTATTATTATTATTGTT TTCGAGATGAAGTTTTGCTCTG TCACCCAGGCTGGA |
| 266 | RBPJ | 4 | 26406174 | 3' splice site | CAGTAATATTTGTATTTGTTTT TAGGGAAGCTATGCGAAATTA TTTAAAAGAGCGAGGGGATCA AACAGTACTTATTCTTCATGCA AAAGTTGCACAGAAGTCATAT GGAAATGAAAAAAGGTAA |
| 267 | RBPJ | 4 | 26383884 | 3' splice site | GTTTCTTTCTTTGTTTTTGAGAC AGGGTCTTGCTCTGTCATCCAG GCTAGAGTGGACTGGTGCGAT CTCAGCTCACTGCAGCCTCGAC TTCCTGGACTCAAGTGATCCTC TTACCTCAGCCTCCT |
| 268 | RBPJ | 4 | 26386352 | 3' splice site | ATTTTCTTTATTTTTTTTTTTCC AGGAAATTTGGTGAGCGGCCT CCACCTAAACGACTTACTAGGT GAGTATTATATTAGTCAGCTTT TTACACATACATTTTATGAAAG TATAAATCTTATTGT |
| 269 | RPS14 | 5 | 150444326 | 3' splice site | CGGCGACCCCCCTTCCTGCGAG TGCTGTCAGAGGGGATGGGGG TGACATCCTCTGTGGGGAGGA AGAGAAAGCGTCATTGCCTGG AGCTGGATGGGAAGGGCCCCC AGGACTCCCTAGACCAATG |
| 270 | RPS14 | 5 | 150444354 | 3' splice site | CAGAGGGGATGGGGGTGACAT CCTCTGTGGGGAGGAAGAGAA AGCGTCATTGCCTGGAGCTGG ATGGGAAGGGCCCCCAGGACT CCCTAGACCAATGGCCTAACC AATCAGCAACAGATCCTGCT |
| 271 | RUNX2 | 6 | 45328660 | 3' splice site | GTTTGGGTATGGTTTGTATTTT CAGTTTAAGGCTGCAAGCAGT ATTTACAACAGAGGGTACAAG TTCTATCTGAAAAAAAAAGGA GGGACTATGGCATCAAACAGC CTCTTCAGCACAGTGACAC |
| 272 | RUNX2 | 6 | 45470323 | 3' splice site | ACTTTCTTTCCATCTCTTGCCTC AGATGCATTTGAGCCTCGCCCA GAGCCCAGCTTGATAGAAAAA TGCCAGACTTGGGTTGAATCA GTCAATTAAAAACCAGCTCTTC TTGTAGTTTGAGAGAC |
| 273 | RUNX2 | 6 | 45512245 | 3' splice site | AGATTTTTCTTTTTCTTTTTCCC AGACCCCAGGCAGGCACAGTC TTCCCCGCCGTGGTCCTATGAC CAGTCTTACCCCTCCTACCTGA GCCAGATGACGTCCCCGTCCAT CCACTCTACCACCCC |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| 274 | RUNX2 | 6 | 45365302 | 3′ splice site | TGGACTAGCTGCCGTATTATTC ATCTAAATAAAAAGGAGAAAT AAAGCTTACAAAATGTACCTA GCTATAAGTAAATGCAAAAAA AAAAGAAAGCAAATATAAATT ACTTCAAAAAGTAGAGAAA |
| 275 | RUNX2 | 6 | 45368432 | 3′ splice site | CACGCCTTTCCTCAGAAAATAT TGCTATCAAAAAAAAAGTTTT AATTGTAGTGAAGTTAATCAC AAAAAGTGAGTTAAACAAAAT GCACTGAACATGCTACTGGGTT TCTAGTTAGATCTCATAT |
| 276 | RUNX2 | 6 | 45371775 | 3′ splice site | AATCTTAGGTAGATGGATAAG CAACTATAACAGACAAACATA TATGCAAATTGGTGGGAGGGA ACCAAAGACATCTGAGCAGAC TTCAGAACTACAGTTTGAAAAT CACTAATTTCCTCCAAATC |
| 277 | RUNX2 | 6 | 45421660 | 3′ splice site | CCTACAAAGAGGGGGTTCCTT GTCCTAGGGGTGGGGAGAGCA AGAGGACGCGACCTGGCGAGA TTGCCCCTAGTCTGGGGCCGCC TCTAGGCTTCGGAAACTGCAC ACGGCGCGCGGGGGGCTCC |
| 278 | SETBP1 | 18 | 45063222 | 3′ splice site | AACAAGATCCTGAAGGCCAAG CGGCTGCAGAGACAATCAAAA ACAGGCAACAACTTCGTGAAG AAGAGGCGCGGGCGTCCCAGG AAGCAGCCCACCCAGTTCGAT GAGGACTCCAGAGACCAAAT |
| 279 | SETBP1 | 18 | 45063348 | 3′ splice site | CCGGTGCTGGAAAAATGCATC GACCTGCCCAGCAAAAGAGGC CAGAAGCCCAGCCTGAGCCCG CTGGTGCTGGAGCCCGCCGCC AGCCAAGACACCATCATGGCC ACCATCGAGGCGGTCATCCA |
| 280 | SETD5 | 3 | 9432166 | 3′ splice site | AATACTGACCTGCATTCTTGAT GTACCCCTCCCCCGTTCCCATC TTGCAGACACTTTTAAGTAATA AAATGCATGCACCTCACTAAC AGAGAATACTTTCCTCTGTCTA AAGTTCTTCACTTAGA |
| 281 | SETD5 | 3 | 9446775 | 3′ splice site | AAAGTACTGGGATTACAGGCG TGAGCCACTGCACCCATCCTGT TTTTCTTTCATATTAAAGTTTC AAAATAACTGACCCTTTTTGAA AAGTTTATGTTTGACCTTGCCT TTATTTACAACTATTC |
| 282 | SETD5 | 3 | 9428822 | 3′ splice site | TAGATATTTTCCTTTTCTGTTAC AGGATTCCTCATGTCCATAACA TGTTGGATGAGGCTCTGCAGCT CACCCCCACTCTCAGAGTGGTC AGTCTCCATTAATTGGACCCCG TGATTTCCAATCTC |
| 283 | SETD5 | 3 | 9445124 | 3′ splice site | CAAAAAAGGAATCCTAATGCT ACAGAACTGCCACTCCTACCA CCTCCTCCAAGCCTACCCACCA TTGGAGCAGAGACTAGACGTA |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | GAAAAGCACGACGGAAAGAGC TAGAGATGGAGCAGCAGAA |
| 284 | SETD5 | 3 | 9446677 | 3' splice site | TGGGTAATTTTTTGTATTTTAG TAGAGACGGAGTTTCACCATG TTGGCCACGACGGTCTCAATCT CCCGACCTCATGATCTTCCCAC CTCAGCCTCCCAAAGTACTGG GATTACAGGCGTGAGCC |
| 285 | SETD5 | 3 | 9475299 | 3' splice site | TAAGTCATCATCTGCTTGTCCT CAGGTAATAAATTATGCCAGA AGATGAATACGGTGATCAAAG ACAGACATTTTACTGCCTTTGG TTTCCTAAAAAGAATACATGGT TAAAAGATGAAGAAAAA |
| 286 | SHANK3 | 22 | 50714916 | 3' splice site | GAGATGGAGCCTCCTTGCTGTG CAGAGAAGCTGGACGAGATGC TGGCAGCCGCCGCAGAGCCAA CGCTGCGGCCAGACATCGCAG ACGCAGACTCCAGAGCCGCCA CCGTCAAACAGAGGCCCAC |
| 287 | SYNGAP1 | 6 | 33437091 | 3' splice site | ATCTCTGTGTCTCCAAATCTCC CTCTCCATATAAAGACACCAGT TTTTATAAGGTGGGTTAAGGGT CCACTCTAATTCAGTATGGCCT GTTTTTTTTGAGATGGAATATG GCTCTTGTTTCCCAG |
| 288 | TBX1 | 22 | 19763485 | 3' splice site | ATGCTGCCCGATCAACCCGCTC CCTCCTCCACTCCCATCTGACC CCAGACCCACAACCCTACTCC ATGCCCTCTCAGAACCCGCCTC TGGAGCCGCAGGCTGCAGACA GCTCTTGCTCCCCTGGG |
| 289 | TBX1 | 22 | 19766590 | 3' splice site | CGAACCCCGAGCTGCGCCTGG AGGCGCCCGGCGCATCGGAGC CGCTGCACCACCACCCCTACA AATATCCGGCCGCCGCCTACG ACCACTATCTCGGGGCCAAGA GCCGGCCGGCGCCCTACCCG |
| 290 | TBX1 | 22 | 19766975 | 3' splice site | AGGAATACGTTCCCCCAGCCC CAGGGGCCACCGCGGCTCTCC CCTTCCCCAGCCTCGAAGCCAT GGGGGCCCCCTCGCCACCCCC AGCCCCTTGGGCTATCGAAGT ATCCGGTTCCCCAGTCCCT |
| 291 | TBX1 | 22 | 19765591 | 3' splice site | TCCTCAGACCCCCGCCCCCCTG CAGGAGGGAGCACCAGCTCCG TAGAGGAGGGGCAGACGTGGA CTGGTTCTTGTCAGGGCAGCAG AAAGGCCCTTGGTGCGCTTCTC CTAACACTCCCCTATCC |
| 292 | TCF4 | 18 | 55314928 | 3' splice site | CTATAATTCTCACCCTTAGGTT TGTGGAGGTGAAAAAGCCAAG TCAAATGTTAGCCTCCATTGTT AACATCCCCTATTCATTTTCAG GACAGCTACAATGGAAGCAGC TGGAATTCAACTCTCCC |
| 293 | TCF4 | 18 | 55551211 | 3' splice site | TGCCCACCTCAGCCTCCCAAAG TGCTGGGATTACAGGCGTGAG |

TABLE 4-continued

Genomic coordinates and sequences for novel cryptic splice sites in a representative list of genes known to be involved in human haploinsufficiency disorders. These sites were identified solely in nascent pre-mRNA derived from metabolic labeling high-throughput sequencing data. These cryptic 5' or 3' splice sites were found in at least one cryptic splice junction, and sometimes multiple cryptic splice junctions, in the nascent RNA sequencing data

| SEQ ID NO: | Gene | Chromosome | Genome Coordinate | Type of Cryptic Site | Genomic Sequence |
|---|---|---|---|---|---|
| | | | | | TCATATCACCCAGCCCTCTTTA CATATTATTCTTCAAACACCTC AAAAATCATTCTCCTGCTGCAT GCTGTGGCTCCTGCAA |
| 294 | TCF4 | 18 | 55365308 | 3′ splice site | TATATATGATGGCTGGGCTTAG CAGATGTGTAGATTCTCCTATT GCTGGGTCCCACTTTTCTGTTA AGGCTTACTTCCTTACTGCTTT TGCCCAAATTATTTCTTGTAGA AGCACTGGATAAATG |
| 295 | TCF4 | 18 | 55597079 | 3′ splice site | CTCTCTCCTGCTGTGCCATGTG AAGATGTGCCTGCTTCCCCTTT GTCTGCTGTGACTATAGGTTTC CTGAGGCCTCCCCAGCCATGC ATCCTGTACAGCCTGTGGAACT GTGAGTCAATTAAACT |
| 296 | TCF4 | 18 | 55461116 | 3′ splice site | ATAGGGAGTCCCATCTCCATA GTTCTGTAAATAAAATGACAG TGTAAGTTATTATTTTATATTA ATAAACAGCACATAAACAAAC ATAGCTCCACTACCAAAACTTC TCCCCTCCAAAGAAATTG |
| 297 | TGIF1 | 18 | 3457709 | 3′ splice site | CTGCCAGTCGGTCGGTGTGGG ACAAAACACAGATATACAGCA GATAGCGGCCAAAAACTTCAC AGACACCTCTCTCATGTACCCA GAGGACACTTGTAAATCTGGA CCAAGTACGAATACACAGA |
| 298 | TGIF1 | 18 | 3453427 | 3′ splice site | AGGGCTGGGCGCGGTGGTTCA CGCCTGTAATCCCAGCACTTTG GGAGGCCTAGGCGAGCAGATC ATCTGAGGTCGGGAGTTCGAG ACCAGCCTGACCAACATGGAG AAACCCCGTCTCTCCTAAA |
| 299 | WDTC1 | 1 | 27263151 | 3′ splice site | TCACGAATTTGTTTCTGTCCCC TAGGAGCGGGGTGCCCTGAGC TTTGAGCGGCGCTACCATGTCA CTGACCCCTTTATCCGGCGGCT GGGCCTGGAAGCAGAGCTGCA GGTAAGAGATCCAGTTT |
| 300 | WDTC1 | 1 | 27271658 | 3′ splice site | TTTAATTTAATTTATTTTATTTG AGATGGAGTCTCACTCTGTTGC CCAGGCTGGAGTGCAATGGCA TGATCTCATCTCACCACAGCCT CCGCCTCCTGGGTTCAAGTGAT TCTCCTGCCTCAGCC |

What is claimed is:

1. A method of identifying a non-productive splice site in a target RNA transcript, the method comprising:

a) incubating a cell with an affinity label to facilitate incorporation of the affinity label into nascent RNA;

b) capturing the affinity labeled nascent RNA with a solid support comprising specificity for the affinity label;

c) isolating the affinity labeled nascent RNA;

d) sequencing the isolated affinity labeled nascent RNA;

e) identifying split reads that do not map to target RNA transcript exon-exon junctions; and f) calculating the probability that the split reads represent non-productive transcripts, thereby identifying non-productive splice sites in the target RNA transcript.

2. The method of claim 1, wherein step a) comprises incubating the cell for less than about 30 minutes in a media containing the affinity label.

3. The method of claim 1, wherein the target RNA transcript exon-exon junctions are annotated target RNA transcript exon-exon junctions.

4. The method of claim 1, wherein the non-productive transcripts are rapidly degraded or not translated into a functional protein.

5. The method of claim 1, wherein the target RNA transcript is associated with a disease or disorder.

6. The method of claim 2, wherein the affinity label comprises 4-thiouridine, 6-thio-guanosine, 5-ethynyl-uridine, or bromodeoxyuridine.

7. The method of claim 6, wherein the 4-thiouridine labeled nascent RNA is biotinylated to produce biotinylated nascent RNA.

8. The method of claim 7, wherein the biotinylated nascent RNA is captured in step b) with a streptavidin linked solid support.

9. The method of claim 6, wherein the bromodeoxyuridine labeled nascent RNA is captured in step b) with an anti-bromodeoxyuridine antibody.

10. The method of claim 1, wherein the cell expresses the target RNA transcript.

11. The method of claim 1, wherein the target RNA transcript comprises:

ADAR, ARSA, ATP1A2, CACNA1A, DNMT1, EIF2B1, EIF2B2, EIF2B5, IDUA, MFSD8, NF2, NPCl, PEX1, PRICKLE2, PRRT2, RAI1, SETD5, SHANK3, SLC6A1, STXBP1, STX1B, and TCF4, or CHD7, CTNNB1, EHMT1, GRN, HTR7, JAK2, KCNQ4, LEPR, LIPC, MBD5, MNX1, NFIA, NMU, NOTCH1, NSD1, PAX6, PHIP, PKD1, PYY, RAI1, RBPJ, RPS14, RUNX2, SETBP1, SETD5, SHANK3, SYNGAP1, TBX1, TCF4, TGIF1, and WDTC1, or ADAR, ARSA, ATP1A2, CACNA1A, CHD7, CTNNB1, DNMT1, EHMT1, EIF2B1, EIF2B2, EIF2B5, GRN, HTR7, IDUA, JAK2, KCNQ4, LEPR, LIPC, MBD5, MFSD8, MNX1, NF2, NFIA, NMU, NOTCH1, NPCl, NSD1, PAX6, PEX1, PHIP, PKD1, PRICKLE2, PRRT2, PYY, RAI1, RBPJ, RPS14, RUNX2, SETBP1, SETD5, SHANK3, SLC6A1, STXBP1, STX1B, SYNGAP1, TBX1, TCF4, TGIF1, and WDTC1.

12. The method of claim 1, wherein the target RNA transcript is expressed from a gene that is related to a disease of haploinsufficiency.

13. The method of claim 5, wherein:

the disease or disorder comprises a disease or disorder of the CNS; or the disease comprises myoclonic-atonic epilepsy (MAE), epilepsy, attention deficit hyperactivity disorder (ADHD), familial hemiplegic migraine-2, familial basilar migraine, alternating hemiplegia of childhood, episodic ataxia type 2, familial hemiplegic migraine, Spinocerebellar ataxia type 6, mental retardation-23, 3p25 microdeletion syndrome, Phelan-McDermid syndrome, schizophrenia-15, Neurofibromatosis (type 1 or type 2), Meningioma, NF2-related, schwannomatosis 1, Hereditary sensory neuropathy type IE, autosomal dominant cerebellar ataxia, deafness, and narcolepsy, Pitt-Hopkins syndrome, Smith-Magenis syndrome, peroxisome biogenesis disorder 1a, Heimler syndrome-1, metachromatic leukodystrophy, leukoencephalopathy with vanishing white matter, Niemann-Pick disease type CI, Niemann-Pick disease type D, Aicardi-Goutieres syndrome-6, early infantile epileptic encephalopathy-4, progressive myoclonic epilepsy 5, familial infantile convulsion with paroxysmal choreoathetosis, episodic kinesigenic dyskinesia 1, benign familial infantile seizures-2, or generalized Epilepsy with febrile seizures plus type 9.

14. The method of claim 1, wherein the target RNA transcript exon-exon junctions are unannotated.

* * * * *

SEQUENCE LISTING

<160> NUMBER OF SEQ ID NOS: 301

<210> SEQ ID NO 1
<211> LENGTH: 50
<212> TYPE: DNA
<213> ORGANISM: Homo sapiens

<400> SEQUENCE: 1
ggagggactc tcctgaggtc acaaagtgag tcacaggcag aatcaggctg 50

<210> SEQ ID NO 2
<211> LENGTH: 50
<212> TYPE: DNA
<213> ORGANISM: Homo sapiens

<400> SEQUENCE: 2
tgacaggcac ccaggtagat acatggtgag tcatgctcac tgaccgaggg 50

<210> SEQ ID NO 3
<211> LENGTH: 50
<212> TYPE: DNA
<213> ORGANISM: Homo sapiens

<400> SEQUENCE: 3
gtcacagaga tcacatgctc acaaggtaat aaaatatcac aaggcaaatg 50

<210> SEQ ID NO 4
<211> LENGTH: 50
<212> TYPE: DNA
<213> ORGANISM: Homo sapiens

<400> SEQUENCE: 4
atggagggtt tgggggttc cacaggtacc ccattagaga cagcagagtg 50

<210> SEQ ID NO 5
<211> LENGTH: 50
<212> TYPE: DNA
<213> ORGANISM: Homo sapiens

<400> SEQUENCE: 5
gtggccagtc cttggaggac aaacagtgag tcccaagcag agagacgcag 50

<210> SEQ ID NO 6
<211> LENGTH: 50
<212> TYPE: DNA
<213> ORGANISM: Homo sapiens

<400> SEQUENCE: 6
tgtattacat atgcattttt agcaggttgg ttcagcataa tgacacagaa 50

<210> SEQ ID NO 7
<211> LENGTH: 50
<212> TYPE: DNA
<213> ORGANISM: Homo sapiens

<400> SEQUENCE: 7
tcccccaaat tccaaaacaa aagaggtcag tgaaagctac tcgcattttg 50

<210> SEQ ID NO 8
<211> LENGTH: 50
<212> TYPE: DNA
<213> ORGANISM: Homo sapiens

<400> SEQUENCE: 8
ttccttcctc caggagcaag ggcgggtgag aggaagaggg cttatagaga 50

<210> SEQ ID NO 9
<211> LENGTH: 50
<212> TYPE: DNA
<213> ORGANISM: Homo sapiens

<400> SEQUENCE: 9
ctgcgcctgg cagagaacaa gccctgtaag tgtttgctgg tgtcgttgca 50

<210> SEQ ID NO 10
<211> LENGTH: 50
<212> TYPE: DNA
<213> ORGANISM: Homo sapiens

<400> SEQUENCE: 10
ctaaaaatac aaaaaaatta gccaggtatg gtggcaggca cctgtagtcc 50

<210> SEQ ID NO 11
<211> LENGTH: 50
<212> TYPE: DNA
<213> ORGANISM: Homo sapiens

<400> SEQUENCE: 11
tatttagagt cacataaaat tggaggtaac ctgaatgcat agcagtgggg 50

<210> SEQ ID NO 12
<211> LENGTH: 50
<212> TYPE: DNA
<213> ORGANISM: Homo sapiens

<400> SEQUENCE: 12
agttccattt ctcgaaagca acaaggtaat atggatcaaa agcctgtgat 50

<210> SEQ ID NO 13
<211> LENGTH: 50
<212> TYPE: DNA
<213> ORGANISM: Homo sapiens

<400> SEQUENCE: 13
tttcttccgc ctgctccacc agcaggtaaa ggaggctgat cacaggctgg 50

<210> SEQ ID NO 14
<211> LENGTH: 50
<212> TYPE: DNA
<213> ORGANISM: Homo sapiens

<400> SEQUENCE: 14
cctgcttctg caaattccct ctcaggtacg ttgaggcagc tgaggggttt 50

<210> SEQ ID NO 15
<211> LENGTH: 50
<212> TYPE: DNA
<213> ORGANISM: Homo sapiens

<400> SEQUENCE: 15
gaccgagaca gcggagaggt tgcgggtgag ctgcgctgag cccaggagcc 50

<210> SEQ ID NO 16
<211> LENGTH: 50
<212> TYPE: DNA
<213> ORGANISM: Homo sapiens

<400> SEQUENCE: 16
tgtgccaagc tctgggcaca taacagtgag tcagatgggg tccctgccct 50

<210> SEQ ID NO 17
<211> LENGTH: 50
<212> TYPE: DNA

<213> ORGANISM: Homo sapiens

<400> SEQUENCE: 17
gtgtgatcat cattcttatt acagggtaag atgcgccctc ttttcctgca 50

<210> SEQ ID NO 18
<211> LENGTH: 50
<212> TYPE: DNA
<213> ORGANISM: Homo sapiens

<400> SEQUENCE: 18
tacgcagcac agtgcgaagc tcacagtgag tcccatggga ttccactggg 50

<210> SEQ ID NO 19
<211> LENGTH: 50
<212> TYPE: DNA
<213> ORGANISM: Homo sapiens

<400> SEQUENCE: 19
gggagagggc agcagccaca gggaggtgag caaagacatt tggtatcagt 50

<210> SEQ ID NO 20
<211> LENGTH: 50
<212> TYPE: DNA
<213> ORGANISM: Homo sapiens

<400> SEQUENCE: 20
acctcaggct tctcttggct gaaaggtagg ctccttccct ccctccttgg 50

<210> SEQ ID NO 21
<211> LENGTH: 50
<212> TYPE: DNA
<213> ORGANISM: Homo sapiens

<400> SEQUENCE: 21
ggactggcat aaggtcacac agctagtaag tttagagaga gatttcaaac 50

<210> SEQ ID NO 22
<211> LENGTH: 50
<212> TYPE: DNA
<213> ORGANISM: Homo sapiens

<400> SEQUENCE: 22
catttagagt ggccccggca cattagtaag tgtgtccagc tcacttcctc 50

<210> SEQ ID NO 23
<211> LENGTH: 50
<212> TYPE: DNA
<213> ORGANISM: Homo sapiens

<400> SEQUENCE: 23
gccatttctg gccaggtgac cttgggtacg ttcttgttcc tgttggaagg 50

<210> SEQ ID NO 24
<211> LENGTH: 50
<212> TYPE: DNA
<213> ORGANISM: Homo sapiens

<400> SEQUENCE: 24
ccacgctgcc cctggaaata aaaaggtaag aaggctgcag agtgtcagta 50

<210> SEQ ID NO 25
<211> LENGTH: 50

<212> TYPE: DNA
<213> ORGANISM: Homo sapiens

<400> SEQUENCE: 25
aatcccagct acttgggagg ctgaggtagg agaattgctt gaacccggga 50

<210> SEQ ID NO 26
<211> LENGTH: 50
<212> TYPE: DNA
<213> ORGANISM: Homo sapiens

<400> SEQUENCE: 26
acagccctgg gaacttcaag tgaaggtaat tttattgtta ttattggtac 50

<210> SEQ ID NO 27
<211> LENGTH: 50
<212> TYPE: DNA
<213> ORGANISM: Homo sapiens

<400> SEQUENCE: 27
aaatcacatg tatgtctgct ttatggtgag gtcttcagag cagccaccgt 50

<210> SEQ ID NO 28
<211> LENGTH: 50
<212> TYPE: DNA
<213> ORGANISM: Homo sapiens

<400> SEQUENCE: 28
gcacttcgtg gaggtgcaga gtcaggtgag gagaggtgaa gtgactcatc 50

<210> SEQ ID NO 29
<211> LENGTH: 50
<212> TYPE: DNA
<213> ORGANISM: Homo sapiens

<400> SEQUENCE: 29
gaacggagat cagtgtggct ggaaggtaaa gtggaaaggg gtgcgaggag 50

<210> SEQ ID NO 30
<211> LENGTH: 50
<212> TYPE: DNA
<213> ORGANISM: Homo sapiens

<400> SEQUENCE: 30
cctttgtttt tctatgacac acaaggtggg tgtttggcaa gagagtaggg 50

<210> SEQ ID NO 31
<211> LENGTH: 50
<212> TYPE: DNA
<213> ORGANISM: Homo sapiens

<400> SEQUENCE: 31
aggaaaagta acaacttgca aaaaggttgg ttctgcttca gagaaatgtt 50

<210> SEQ ID NO 32
<211> LENGTH: 50
<212> TYPE: DNA
<213> ORGANISM: Homo sapiens

<400> SEQUENCE: 32
gaacttgtcc agctgggccc tgacagtgag ttcagagggc ctgctgggca 50

<210> SEQ ID NO 33

<211> LENGTH: 50
<212> TYPE: DNA
<213> ORGANISM: Homo sapiens

<400> SEQUENCE: 33
gcatttggct gtttgaaaag cgctggtaag agctgggatc ctgatgattg 50

<210> SEQ ID NO 34
<211> LENGTH: 50
<212> TYPE: DNA
<213> ORGANISM: Homo sapiens

<400> SEQUENCE: 34
agcaccaggg tggctttgct gctgtgtaag tcaaagagcc ttctccgttc 50

<210> SEQ ID NO 35
<211> LENGTH: 50
<212> TYPE: DNA
<213> ORGANISM: Homo sapiens

<400> SEQUENCE: 35
taaccctact gttctaattt ccaggccaac tctgtcctat tgtgggtctc 50

<210> SEQ ID NO 36
<211> LENGTH: 50
<212> TYPE: DNA
<213> ORGANISM: Homo sapiens

<400> SEQUENCE: 36
tggctgcctt ccttaatcct gcagaatctc ggggtcaagt cagggaggtg 50

<210> SEQ ID NO 37
<211> LENGTH: 50
<212> TYPE: DNA
<213> ORGANISM: Homo sapiens

<400> SEQUENCE: 37
ggggacacct ttctccccat tcagccacag gtggagcttc tttcttgctc 50

<210> SEQ ID NO 38
<211> LENGTH: 50
<212> TYPE: DNA
<213> ORGANISM: Homo sapiens

<400> SEQUENCE: 38
tcagccacct tctccatttt ccagaagggg aaactgatgc ccagagggga 50

<210> SEQ ID NO 39
<211> LENGTH: 50
<212> TYPE: DNA
<213> ORGANISM: Homo sapiens

<400> SEQUENCE: 39
ataccataaa attcctttcc acagctaagt gagtgagtca agaacagatg 50

<210> SEQ ID NO 40
<211> LENGTH: 50
<212> TYPE: DNA
<213> ORGANISM: Homo sapiens

<400> SEQUENCE: 40
gtcttgttct tacacctctt gcagcactta tcacagggta ttatgatcag 50

<210> SEQ ID NO 41
<211> LENGTH: 50
<212> TYPE: DNA
<213> ORGANISM: Homo sapiens

<400> SEQUENCE: 41
ggtgctactc tctccttctg ccagagagga ccctgagccc aagggtggtg 50

<210> SEQ ID NO 42
<211> LENGTH: 50
<212> TYPE: DNA
<213> ORGANISM: Homo sapiens

<400> SEQUENCE: 42
catcaccact tcccttctcc aaagcatgca agttcaattt ctaaaattca 50

<210> SEQ ID NO 43
<211> LENGTH: 50
<212> TYPE: DNA
<213> ORGANISM: Homo sapiens

<400> SEQUENCE: 43
attaatttct ttcttaaacc acagagtttc aaaaagaaat aaaggcaaac 50

<210> SEQ ID NO 44
<211> LENGTH: 50
<212> TYPE: DNA
<213> ORGANISM: Homo sapiens

<400> SEQUENCE: 44
aaagtatctc tgatccattc ctaggactag ggacgccgga ggagggcaca 50

<210> SEQ ID NO 45
<211> LENGTH: 50
<212> TYPE: DNA
<213> ORGANISM: Homo sapiens

<400> SEQUENCE: 45
tgacatcaca tatccatcca ccaggtgcat atctgagcag agtgagggct 50

<210> SEQ ID NO 46
<211> LENGTH: 50
<212> TYPE: DNA
<213> ORGANISM: Homo sapiens

<400> SEQUENCE: 46
gctgggcctc ccgtccttcc ttagagggcc aggctttggg tgggttgggg 50

<210> SEQ ID NO 47
<211> LENGTH: 50
<212> TYPE: DNA
<213> ORGANISM: Homo sapiens

<400> SEQUENCE: 47
tcacccccac ccccccccca ccagatccaa atgtagttct gctccagagt 50

<210> SEQ ID NO 48
<211> LENGTH: 50
<212> TYPE: DNA
<213> ORGANISM: Homo sapiens

<400> SEQUENCE: 48
tctcctctcc tcctccccac acagctgctg ggcggtcttg ccaagtcacc 50

<210> SEQ ID NO 49
<211> LENGTH: 50
<212> TYPE: DNA
<213> ORGANISM: Homo sapiens

<400> SEQUENCE: 49
aataatttct tttcctttgg atagatagcc agtagtggga ttgctggatc 50

<210> SEQ ID NO 50
<211> LENGTH: 50
<212> TYPE: DNA
<213> ORGANISM: Homo sapiens

<400> SEQUENCE: 50
caaggctgtt tccttatctg tcagatgggt gaggtagccc tggcttacat 50

<210> SEQ ID NO 51
<211> LENGTH: 50
<212> TYPE: DNA
<213> ORGANISM: Homo sapiens

<400> SEQUENCE: 51
aggcagaaat atttctcctt ctaggccatg accttgacaa gggcaagggt 50

<210> SEQ ID NO 52
<211> LENGTH: 50
<212> TYPE: DNA
<213> ORGANISM: Homo sapiens

<400> SEQUENCE: 52
aggccgtgct gattgtatct tcaggggagt accttgtaga gatgtgtgtc 50

<210> SEQ ID NO 53
<211> LENGTH: 50
<212> TYPE: DNA
<213> ORGANISM: Homo sapiens

<400> SEQUENCE: 53
cctggcctct cggtctctgc ctaggtcccc accccacgca gccgcctgtc 50

<210> SEQ ID NO 54
<211> LENGTH: 50
<212> TYPE: DNA
<213> ORGANISM: Homo sapiens

<400> SEQUENCE: 54
aaaactgggt gtccttgccc ctagggaagg acaaattttc tttaagtccc 50

<210> SEQ ID NO 55
<211> LENGTH: 50
<212> TYPE: DNA
<213> ORGANISM: Homo sapiens

<400> SEQUENCE: 55
tgactttctt tgcctcgtgc tcagtgcctg acaggcaccc aggtagatac 50

<210> SEQ ID NO 56
<211> LENGTH: 50
<212> TYPE: DNA
<213> ORGANISM: Homo sapiens

<400> SEQUENCE: 56
tggagcgctc attccctttc ccaggaagct cagccttatc cccatgaaga 50

<210> SEQ ID NO 57
<211> LENGTH: 50
<212> TYPE: DNA
<213> ORGANISM: Homo sapiens

<400> SEQUENCE: 57
taggtgttat cacttctgtt ttagacagag agagtagatg actaacctac 50

<210> SEQ ID NO 58
<211> LENGTH: 50
<212> TYPE: DNA
<213> ORGANISM: Homo sapiens

<400> SEQUENCE: 58
tattattatc ttcccatttt atagatgagg gtcagagagg tgaagtaact 50

<210> SEQ ID NO 59
<211> LENGTH: 50
<212> TYPE: DNA
<213> ORGANISM: Homo sapiens

<400> SEQUENCE: 59
aaaaatcagc ttctcgttcc acaggtcttg agtggggccc aagattctgc 50

<210> SEQ ID NO 60
<211> LENGTH: 50
<212> TYPE: DNA
<213> ORGANISM: Homo sapiens

<400> SEQUENCE: 60
gctgtattaa tgcgtttctt ctaggcctcc cgtgtcttgt tcttacacct 50

<210> SEQ ID NO 61
<211> LENGTH: 50
<212> TYPE: DNA
<213> ORGANISM: Homo sapiens

<400> SEQUENCE: 61
ggctctgttc cacctggccc acaggcagcc agacgttaag gttatctccc 50

<210> SEQ ID NO 62
<211> LENGTH: 50
<212> TYPE: DNA
<213> ORGANISM: Homo sapiens

<400> SEQUENCE: 62
ccccttgcct gccatctggt ccagggctgg gctgctcaca gccaatcatc 50

<210> SEQ ID NO 63
<211> LENGTH: 50
<212> TYPE: DNA
<213> ORGANISM: Homo sapiens

<400> SEQUENCE: 63
actccacctt ttctcccttt caagccctac cccaggagcc tgggggcaga 50

<210> SEQ ID NO 64
<211> LENGTH: 50
<212> TYPE: DNA
<213> ORGANISM: Homo sapiens

<400> SEQUENCE: 64

-continued tctagttttc tccttcctca gcagaccaaa tctcactctg agtacaagat 50

<210> SEQ ID NO 65
<211> LENGTH: 50
<212> TYPE: DNA
<213> ORGANISM: Homo sapiens

<400> SEQUENCE: 65
ctgttatcct gtttttttc caaggtgccc agatttcata ttgtttaaac 50

<210> SEQ ID NO 66
<211> LENGTH: 50
<212> TYPE: DNA
<213> ORGANISM: Homo sapiens

<400> SEQUENCE: 66
cccacttcct cccatcccac ttagaatgaa acctgaatcc ttgctgtgac 50

<210> SEQ ID NO 67
<211> LENGTH: 50
<212> TYPE: DNA
<213> ORGANISM: Homo sapiens

<400> SEQUENCE: 67
gcatctttct gaccctcact gtagaccagg tttgttgcca gggagagctg 50

<210> SEQ ID NO 68
<211> LENGTH: 50
<212> TYPE: DNA
<213> ORGANISM: Homo sapiens

<400> SEQUENCE: 68
gacctgggcc ccgttcttgc ataggtgaca gtgcagctgg gaagctaaga 50

<210> SEQ ID NO 69
<211> LENGTH: 50
<212> TYPE: DNA
<213> ORGANISM: Homo sapiens

<400> SEQUENCE: 69
ctgcaccttt gattgtccca tcagagcaaa tgtttttaaa gaagcatgat 50

<210> SEQ ID NO 70
<211> LENGTH: 50
<212> TYPE: DNA
<213> ORGANISM: Homo sapiens

<400> SEQUENCE: 70
gctgccctca tcccacgccc acagctgtcc cgagggcagc gggccccact 50

<210> SEQ ID NO 71
<211> LENGTH: 50
<212> TYPE: DNA
<213> ORGANISM: Homo sapiens

<400> SEQUENCE: 71
aagctaactg cccttcctcc tcaggtcagc tcctcgcagc agctgcaagg 50

<210> SEQ ID NO 72
<211> LENGTH: 50
<212> TYPE: DNA
<213> ORGANISM: Homo sapiens

<400> SEQUENCE: 72
ctgggttttt ttcttcatct atagaatgcc atggtagacc aggtgcacca 50

<210> SEQ ID NO 73
<211> LENGTH: 50
<212> TYPE: DNA
<213> ORGANISM: Homo sapiens

<400> SEQUENCE: 73
ctgcttctgc aaattccctc tcaggtacgt tgaggcagct gaggggttta 50

<210> SEQ ID NO 74
<211> LENGTH: 50
<212> TYPE: DNA
<213> ORGANISM: Homo sapiens

<400> SEQUENCE: 74
cactttaacc tctctgtgcc tcagtttacc catcaataaa atgggggcta 50

<210> SEQ ID NO 75
<211> LENGTH: 50
<212> TYPE: DNA
<213> ORGANISM: Homo sapiens

<400> SEQUENCE: 75
atccttgcac catccctgtt acagcaacct ccacccatgc tccctctcct 50

<210> SEQ ID NO 76
<211> LENGTH: 50
<212> TYPE: DNA
<213> ORGANISM: Homo sapiens

<400> SEQUENCE: 76
tctctgcctc taatctcctg ccagctcctc ccaatggtca aacccagcta 50

<210> SEQ ID NO 77
<211> LENGTH: 50
<212> TYPE: DNA
<213> ORGANISM: Homo sapiens

<400> SEQUENCE: 77
gtgccaggct ccttcctgcc tcagggcctt tgcacttgct gctccctctg 50

<210> SEQ ID NO 78
<211> LENGTH: 50
<212> TYPE: DNA
<213> ORGANISM: Homo sapiens

<400> SEQUENCE: 78
atcagccctg ccccatccct gcagctagtc cccaggttcc ttagtccggt 50

<210> SEQ ID NO 79
<211> LENGTH: 50
<212> TYPE: DNA
<213> ORGANISM: Homo sapiens

<400> SEQUENCE: 79
cagggagctt tccctgacct ccaggacagc gcgtggcaag cactgcccac 50

<210> SEQ ID NO 80
<211> LENGTH: 50
<212> TYPE: DNA
<213> ORGANISM: Homo sapiens

<400> SEQUENCE: 80
tattgtccca ctttaccgct gcaggatctg gggctcacct agccagcatc 50

<210> SEQ ID NO 81
<211> LENGTH: 50
<212> TYPE: DNA
<213> ORGANISM: Homo sapiens

<400> SEQUENCE: 81
gaatgtgtgt tttctctgtg ccagctatct aaatgacccc atgctgcaaa 50

<210> SEQ ID NO 82
<211> LENGTH: 50
<212> TYPE: DNA
<213> ORGANISM: Homo sapiens

<400> SEQUENCE: 82
gctgtgtgct ttatatcgtt gcagttaatt ttcacaaaac cctgtgagat 50

<210> SEQ ID NO 83
<211> LENGTH: 50
<212> TYPE: DNA
<213> ORGANISM: Homo sapiens

<400> SEQUENCE: 83
ttcctttata ttgattgcct ataggttaag ataacactgg gcctggcgca 50

<210> SEQ ID NO 84
<211> LENGTH: 50
<212> TYPE: DNA
<213> ORGANISM: Homo sapiens

<400> SEQUENCE: 84
cgaagctccc tattcattcc ccagggcatg gaggggacgc ggagtgaatg 50

<210> SEQ ID NO 85
<211> LENGTH: 50
<212> TYPE: DNA
<213> ORGANISM: Homo sapiens

<400> SEQUENCE: 85
tgggcacccg gacctgttcc acaggggctc gccctcgtgc ccagcacagg 50

<210> SEQ ID NO 86
<211> LENGTH: 50
<212> TYPE: DNA
<213> ORGANISM: Homo sapiens

<400> SEQUENCE: 86
gaagtccatc tcctttgtcc ttagaagccc atccctgttg cctagcccaa 50

<210> SEQ ID NO 87
<211> LENGTH: 50
<212> TYPE: DNA
<213> ORGANISM: Homo sapiens

<400> SEQUENCE: 87
tacacgcctc cctcattctt gcagactatt ctaaagcaga gtctctctgc 50

<210> SEQ ID NO 88
<211> LENGTH: 50
<212> TYPE: DNA
<213> ORGANISM: Homo sapiens

<400> SEQUENCE: 88
ggttcgatgt tcctcatcct gcagcagacg tctctgcggg cacccaccag 50

<210> SEQ ID NO 89
<211> LENGTH: 50
<212> TYPE: DNA
<213> ORGANISM: Homo sapiens

<400> SEQUENCE: 89
tttttttttt tttttttgc tcaggccaaa taaaacaagc ccaagggcca 50

<210> SEQ ID NO 90
<211> LENGTH: 50
<212> TYPE: DNA
<213> ORGANISM: Homo sapiens

<400> SEQUENCE: 90
ctgcacccct gctgccctct gtaggagctg cctgcctgcc ccatcgctgc 50

<210> SEQ ID NO 91
<211> LENGTH: 50
<212> TYPE: DNA
<213> ORGANISM: Homo sapiens

<400> SEQUENCE: 91
gtcctcgatt ccctggcttt tcagggctcc ccactcactc catggcgggg 50

<210> SEQ ID NO 92
<211> LENGTH: 50
<212> TYPE: DNA
<213> ORGANISM: Homo sapiens

<400> SEQUENCE: 92
caaaagtcac cttccttcct ccaggagcaa gggcgggtga gaggaagagg 50

<210> SEQ ID NO 93
<211> LENGTH: 50
<212> TYPE: DNA
<213> ORGANISM: Homo sapiens

<400> SEQUENCE: 93
gatctctttt tatcgccatt ccaggggcct caggtcctac tggggaaact 50

<210> SEQ ID NO 94
<211> LENGTH: 50
<212> TYPE: DNA
<213> ORGANISM: Homo sapiens

<400> SEQUENCE: 94
tgactcctca tctctgtccc ctagtttccc agctgatgaa aatcaccttt 50

<210> SEQ ID NO 95
<211> LENGTH: 50
<212> TYPE: DNA
<213> ORGANISM: Homo sapiens

<400> SEQUENCE: 95
aacactggcc tgccttccac ccaggacttt ttcccatcac taactaaaaa 50

<210> SEQ ID NO 96
<211> LENGTH: 50
<212> TYPE: DNA

<213> ORGANISM: Homo sapiens

<400> SEQUENCE: 96
tccggttcta atctcccctt caagggcagc caccatctcg tttctctgca 50

<210> SEQ ID NO 97
<211> LENGTH: 50
<212> TYPE: DNA
<213> ORGANISM: Homo sapiens

<400> SEQUENCE: 97
tgactgttat ctcggacttt gcaggagttc ctttccctcc gaacgctgct 50

<210> SEQ ID NO 98
<211> LENGTH: 50
<212> TYPE: DNA
<213> ORGANISM: Homo sapiens

<400> SEQUENCE: 98
cgaagtctcg ctcttgttcc ccaggctgga gtacaatggc acgatctcgg 50

<210> SEQ ID NO 99
<211> LENGTH: 50
<212> TYPE: DNA
<213> ORGANISM: Homo sapiens

<400> SEQUENCE: 99
ggtagatcat ttttatcccg ccagggagtg tgatgcagga agaccacatg 50

<210> SEQ ID NO 100
<211> LENGTH: 50
<212> TYPE: DNA
<213> ORGANISM: Homo sapiens

<400> SEQUENCE: 100
agtcctggcc ccctggcttg tcagatgtac atgaccttca gcaagtcact 50

<210> SEQ ID NO 101
<211> LENGTH: 50
<212> TYPE: DNA
<213> ORGANISM: Homo sapiens

<400> SEQUENCE: 101
tctctacttc catccttcct acagccttgt cagaatggga tacttccctg 50

<210> SEQ ID NO 102
<211> LENGTH: 50
<212> TYPE: DNA
<213> ORGANISM: Homo sapiens

<400> SEQUENCE: 102
tggcccatct tcctccaacc tcagatgaag aaactgggga accacagggg 50

<210> SEQ ID NO 103
<211> LENGTH: 50
<212> TYPE: DNA
<213> ORGANISM: Homo sapiens

<400> SEQUENCE: 103
tcttctggct ctgccctcct ctagcttgct cttagggcct gtgcatctgg 50

<210> SEQ ID NO 104
<211> LENGTH: 50

<212> TYPE: DNA
<213> ORGANISM: Homo sapiens

<400> SEQUENCE: 104
cctagatttt aaattcattt gcagctagtg ctgatgtcat gcactcagcc 50

<210> SEQ ID NO 105
<211> LENGTH: 50
<212> TYPE: DNA
<213> ORGANISM: Homo sapiens

<400> SEQUENCE: 105
agtggagttc tctctcttaa ccaggttggc gaaaagcact cttgcagcga 50

<210> SEQ ID NO 106
<211> LENGTH: 50
<212> TYPE: DNA
<213> ORGANISM: Homo sapiens

<400> SEQUENCE: 106
ggatgctgtt cctgcccttt gaagatccac ttgcattgaa aaccgtagat 50

<210> SEQ ID NO 107
<211> LENGTH: 50
<212> TYPE: DNA
<213> ORGANISM: Homo sapiens

<400> SEQUENCE: 107
cttccattta ttcatctgtc ctaggacagt gaggctaggc aaactcatct 50

<210> SEQ ID NO 108
<211> LENGTH: 50
<212> TYPE: DNA
<213> ORGANISM: Homo sapiens

<400> SEQUENCE: 108
ctcacccttg ctctgctttt gaagctgggg aacttggagg aaggggttcc 50

<210> SEQ ID NO 109

<400> SEQUENCE: 109

000

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
tcttgcagac tattctaaag 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
agggtgggca cccggacctg 20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
ggaagacctg ggccccgttc 20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
tgggccccgt tcttgcatag 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
ttgcataggt gacagtgcag 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
tgatcatcat tcttattaca 20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
gcttctgcaa attccctctc 20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
aattccctct caggtacgtt 20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
gtttaaaaat cagcttctcg 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
tctggctgta ttaatgcgtt 20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
tattaatgcg tttcttctag 20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
tcttctaggc ctcccgtgtc 20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
ccgtgtcttg ttcttacacc 20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
tgttcttaca cctcttgcag 20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
tcttgcagca cttatcacag 20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
cttccgcctg ctccaccagc 20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
gctccaccag caggtaaagg 20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
aggtaaagga ggctgatcac 20

<210> SEQ ID NO 128
<211> LENGTH: 125
<212> TYPE: DNA
<213> ORGANISM: Homo sapiens

<400> SEQUENCE: 128
taaaactcac ctggcagagg caccgtaagt cagcacctca tgttaaatag gggtggctca 60
agcatttatg ttgttctaaa cccaggttaa tgtctatgat acctagttgc atgaaatagt 120
tggtg 125

<210> SEQ ID NO 129
<211> LENGTH: 125
<212> TYPE: DNA
<213> ORGANISM: Homo sapiens

<400> SEQUENCE: 129
acagagccaa tggcttggaa tgaggtaggg aaatgtgagc agttatttat ctggtagttt 60
cctagagcag gtatggcagc ttgttctttc ctctcaaaac acttagtaca cattcatttg 120
cattg 125

<210> SEQ ID NO 130
<211> LENGTH: 125
<212> TYPE: DNA
<213> ORGANISM: Homo sapiens

<400> SEQUENCE: 130
ctctttcttt tttttttctt ttgagacaga gttttgctct tgtcgcccag gctggagtgc 60
agtggtgtga tctcagctca ctgcaacctc tgcctcccag tttcaagcga ttctcctgcc 120
tcagc 125

<210> SEQ ID NO 131
<211> LENGTH: 125
<212> TYPE: DNA
<213> ORGANISM: Homo sapiens

<400> SEQUENCE: 131
gccatggccg ccgccgatgc cgaggtgagc agcggggccg gcgggggcgg gcgcgggggc 60
ggcgggcagc ggcggaggcg gcgcgggggc gaagaaccgg gcggggcggc ggcaggcggc 120
cggcg 125

<210> SEQ ID NO 132
<211> LENGTH: 125
<212> TYPE: DNA
<213> ORGANISM: Homo sapiens

<400> SEQUENCE: 132
gttgatggat tactttatcc taaggtaagt gggcagtttg attttaagtt gctcactcag 60
caaaccaggt agggaatagt tatttgcttt tgtatttttt tttttttttt gagatggagt 120
ttcgc 125

<210> SEQ ID NO 133
<211> LENGTH: 125
<212> TYPE: DNA
<213> ORGANISM: Homo sapiens

<400> SEQUENCE: 133
cctccacacc aggacacagt cgaggtgccg aacctcctcc acaccagggc acagtcgagg 60
tgccgaaccc cctccacacc agggcacagt cgaggtgccg aaccccctcc acaccagggc 120
acagt 125

<210> SEQ ID NO 134
<211> LENGTH: 125
<212> TYPE: DNA
<213> ORGANISM: Homo sapiens

<400> SEQUENCE: 134
gggcgggttc cggcgtggct cgaggtggct gtttatgtgg aggatggtca tttgtgagtg 60
cttgccagcc atcgtgacag tcctgagctg gagtctgtgg ctacatctga aatcattaat 120
aaaac 125

<210> SEQ ID NO 135
<211> LENGTH: 125
<212> TYPE: DNA
<213> ORGANISM: Homo sapiens

<400> SEQUENCE: 135
gccatgtacc gagactgtag agaggccgac tgaggggcgc cgtgtaccga gaccgtagag 60
aggccgattg aggggcgcca tgtaccgaga ccgtagagag gccgactgag gggcgccgtg 120
taccg 125

<210> SEQ ID NO 136
<211> LENGTH: 125
<212> TYPE: DNA
<213> ORGANISM: Homo sapiens

<400> SEQUENCE: 136
cgccgcccac agcacgtgca ctcacctcca cccaagacgc cccccacagc acgtgcactg 60
gactcctccc aagacgcccc gcacagcacg tgcactcgac tcctcccaag acgccccgca 120
cagca 125

<210> SEQ ID NO 137
<211> LENGTH: 125
<212> TYPE: DNA
<213> ORGANISM: Homo sapiens

<400> SEQUENCE: 137
cgccccgcac agcacgtgca ctcaccgact ccacccactg tctacccagg gcgcagccgc 60
tccagcagct cttccctggc ccctccccca ccttcacttt ttgctctctt cggagcattc 120
attgc 125

<210> SEQ ID NO 138
<211> LENGTH: 125
<212> TYPE: DNA
<213> ORGANISM: Homo sapiens

<400> SEQUENCE: 138
cccctcccag acttctcaca ctcacccctc ccagacttct cacactcacc cctcccagac 60
ttctcacact cgccccctcc cagacttctc acactcaccc ctcccagact tctcacactc 120
acccc 125

<210> SEQ ID NO 139
<211> LENGTH: 125
<212> TYPE: DNA
<213> ORGANISM: Homo sapiens

<400> SEQUENCE: 139
cccctcccag acttctcaca ctcacccctc ccagacttct cacactcacc ccctcccaga 60
cttctcacac tcacccctcc cagacttctc acactcaccc cctcccctct cacccccctcc 120 cacgc 125

<210> SEQ ID NO 140
<211> LENGTH: 125
<212> TYPE: DNA
<213> ORGANISM: Homo sapiens

<400> SEQUENCE: 140
cccctcccag acttctcaca ctcaccccct cccagacttc tcacactcac ccctcccaga 60
cttctcacac tcacccccctc ccctctcacc ccctcccacg cctcaccccc tcccacgcct 120
ctcac 125

<210> SEQ ID NO 141
<211> LENGTH: 125
<212> TYPE: DNA

<213> ORGANISM: Homo sapiens

<400> SEQUENCE: 141
cttctcacac tcacccctcc cagacttctc acactcaccc ctcccagact tctcacactc 60
gccccctccc agacttctca cactcacccc tcccagactt ctcacactca ccccctccca 120
gactt 125

<210> SEQ ID NO 142
<211> LENGTH: 125
<212> TYPE: DNA
<213> ORGANISM: Homo sapiens

<400> SEQUENCE: 142
ttctcacact cgccccctcc cagacttctc acactcaccc ctcccagact tctcacactc 60 acccccctccc agacttctca cactcacccc tcccagactt ctcacactca ccccctcccc 120
tctca 125

<210> SEQ ID NO 143
<211> LENGTH: 125
<212> TYPE: DNA
<213> ORGANISM: Homo sapiens

<400> SEQUENCE: 143
ttctcacact cacccccctcc cagacttctc acactcaccc ctcccagact tctcacactc 60 acccccctccc ctctcacccc ctcccacgcc tcacccccctc ccacgcctct cacccccctcc 120 cacgc 125

<210> SEQ ID NO 144
<211> LENGTH: 125
<212> TYPE: DNA
<213> ORGANISM: Homo sapiens

<400> SEQUENCE: 144
cttctcacac tcacccctcc cagacttctc acactcaccc cctcccctct cacccccctcc 60 cacgcctcac cccctcccac gcctctcacc ccctcccacg cctctcaccc tctcccacgc 120
ctctc 125

<210> SEQ ID NO 145
<211> LENGTH: 125
<212> TYPE: DNA
<213> ORGANISM: Homo sapiens

<400> SEQUENCE: 145
cccctcccag acttctcaca ctcacccctc ccagacttct cacactcacc ccctcccctc 60 tcacccccctc ccacgcctca ccccctccca cgcctctcac cccctcccac gcctctcacc 120
ctctc 125

<210> SEQ ID NO 146
<211> LENGTH: 125
<212> TYPE: DNA
<213> ORGANISM: Homo sapiens

<400> SEQUENCE: 146
gtaccgagac cgtagagagg ccgactgagg ggcgccatgt accgagaccg tagagaggcc 60
gactgagggg cgccgtgtac cgagaccgta gagaggccga ctgaggggcg ccgtgtaccg 120
agacc 125

<210> SEQ ID NO 147
<211> LENGTH: 125
<212> TYPE: DNA
<213> ORGANISM: Homo sapiens

<400> SEQUENCE: 147
gtaccgagac cgtagagagg ccgactgagg ggcgccatgt accgagaccg tagagaggcc 60
gactgagggg cgccgtgtac cgagaccgta gagaggccga cttaggggcg ccgtgtaccg 120
agacc 125

<210> SEQ ID NO 148
<211> LENGTH: 125
<212> TYPE: DNA
<213> ORGANISM: Homo sapiens

<400> SEQUENCE: 148
cctcccctct cacccccctcc cacgcctcac cccctcccac gcctctcacc ccctcccacg 60
cctctcaccc tctcccacgc ctctcaccct ctcccacgcc tctcaccctc tcccacgcct 120
ctcac 125

<210> SEQ ID NO 149
<211> LENGTH: 125
<212> TYPE: DNA
<213> ORGANISM: Homo sapiens

<400> SEQUENCE: 149
ggctgggtat ggccagggac caggtcccac ctcgtccaac cctctcgccc ccctctgacc 60
atccagggcg tctgttgtgc tgatcggcgc cactgctgtc ctgctggctt ccgctgcgca 120
gccag 125

<210> SEQ ID NO 150
<211> LENGTH: 125
<212> TYPE: DNA
<213> ORGANISM: Homo sapiens

<400> SEQUENCE: 150
tgcaggcaga ccatgtggac cctggtgagc tgggtggcct taacagcagg gctggtggct 60
ggaacgcggt gcccagatgg tcagttctgc cctgtggcct gctgcctgga ccccggagga 120
gccag 125

<210> SEQ ID NO 151
<211> LENGTH: 125
<212> TYPE: DNA
<213> ORGANISM: Homo sapiens

<400> SEQUENCE: 151
tggggctgct gcccttttac ccaggtaccc aggggtggcg ggtgggtggg ctgagcacag 60
tgtggcaggc agccgggccc cagtgcccac ctgcccttct tcatctgccc taggctgtgt 120
gctgt 125

<210> SEQ ID NO 152
<211> LENGTH: 125
<212> TYPE: DNA
<213> ORGANISM: Homo sapiens

<400> SEQUENCE: 152
ggtattgacg gccaggtttc taaacctctt aaaactcccc aactctggtg ccaccttaga 60
caatactctt ttaagcactc ctttttagtt atccccacct gcccagttcc cttattaggc 120
caaga 125

<210> SEQ ID NO 153
<211> LENGTH: 125
<212> TYPE: DNA
<213> ORGANISM: Homo sapiens

<400> SEQUENCE: 153
cataagcaag atggtaaaaa tctggtaagt ttgctttatg attgaataat ggtttcattt 60
tatagttctc agaaatgtgt attttagaat cttagtacca aaattatttt ctggtaggaa 120
ttttg 125

<210> SEQ ID NO 154
<211> LENGTH: 125
<212> TYPE: DNA
<213> ORGANISM: Homo sapiens

<400> SEQUENCE: 154
tgtgaggtgg aagggcgagg ccgaggcggc ggtggcgtcg cgtccccccct ctccgcccct 60 ggcctcgggg acgcggcggc accttcacac tttccgcttg gcccgctgct cgcctttcag 120
gccgc 125

<210> SEQ ID NO 155
<211> LENGTH: 125
<212> TYPE: DNA
<213> ORGANISM: Homo sapiens

<400> SEQUENCE: 155
tgacagtatc ctcccatcct tcaggtaggt cctgctgggg gtgggggtgg gtggggggct 60
ggcagcaatg ccctttgagg acaagtggct gagactcaac cctggagggt ggaaaggggg 120
tgatg 125

<210> SEQ ID NO 156
<211> LENGTH: 125
<212> TYPE: DNA
<213> ORGANISM: Homo sapiens

<400> SEQUENCE: 156
gggatgtgcc ttagaggatt atgggtaagt tatcatttca aaaagaacta ttcctctttc 60
tgtgtctttg tcactattag tatgggtgtt agagagttcg gtcaatttag caccaagttc 120
taacc 125

<210> SEQ ID NO 157
<211> LENGTH: 125
<212> TYPE: DNA
<213> ORGANISM: Homo sapiens

<400> SEQUENCE: 157
gcctatgagc aaaggtaaga agaggtacag agtggtaatc cattgcctct tttaatattt 60
aacttttgca aactctccta ttttaaatta tctttcaagc agcctgcaat tctctgcatc 120
tgaaa 125

<210> SEQ ID NO 158
<211> LENGTH: 125

<212> TYPE: DNA
<213> ORGANISM: Homo sapiens

<400> SEQUENCE: 158
tcctctcctg agagttgccc cgcaccttgg gcgaggagtt cggagcggcc ccatcgcaga 60
gcccacggcc agccgagcgc gcgcgacgca ggtgcccgag ccccggcgcc gccgccatct 120
ctgcc 125

<210> SEQ ID NO 159
<211> LENGTH: 125
<212> TYPE: DNA
<213> ORGANISM: Homo sapiens

<400> SEQUENCE: 159
aaacctaaaa gcaattttgt ttgggttgaa acaaggtggg cgggcagtca ggaacccacc 60
cttttaactt ctgtgtcctc tgccatctcc tgtagcagcc cccaaagtag ttccacaaga 120
tcctt 125

<210> SEQ ID NO 160
<211> LENGTH: 125
<212> TYPE: DNA
<213> ORGANISM: Homo sapiens

<400> SEQUENCE: 160
gaatgatctt tgggtcaaca atgaaaacaa gatggaagta aaaaattatc tgaactgaat 60
gataatagtg acacaactta tcaaaacctc tgggacacag gaaaaatggt gctaagagga 120
aagtt 125

<210> SEQ ID NO 161
<211> LENGTH: 125
<212> TYPE: DNA
<213> ORGANISM: Homo sapiens

<400> SEQUENCE: 161
acccgtcaga gagggacatg cgcagtgagt gcctcccgtc tcttctaccc gaaccccccc 60
tcccccccaa gcagagagac cccagcagca gcagcagctg atgatgaaga gagaggcagt 120
ggcag 125

<210> SEQ ID NO 162
<211> LENGTH: 125
<212> TYPE: DNA
<213> ORGANISM: Homo sapiens

<400> SEQUENCE: 162
tcaaaatgga gtgctttatg tcaggtaagt tcttattatt acctgtggta cctgcaaagt 60
tgtactccaa agactaagga gagaaccaag catggtgact gatggcacct catataaatg 120
tgaaa 125

<210> SEQ ID NO 163
<211> LENGTH: 125
<212> TYPE: DNA
<213> ORGANISM: Homo sapiens

<400> SEQUENCE: 163
tgttccacca caaaccaccc caaggcccac ctccccctcc tccaccttct tgtgctcttc 60
agaaaaagcc attaacatct gagaaagatc cacttggcat tcttgaccct attcctagta 120
aacca 125

<210> SEQ ID NO 164
<211> LENGTH: 125
<212> TYPE: DNA
<213> ORGANISM: Homo sapiens

<400> SEQUENCE: 164
cccggggcgc gcattgtccg cacggtgtgt actcggggag gggcgccagg tgcgcgggcg 60
gaatgtaggg tcggcgcggg gccggggggc gggcccgggg ccggggggtc ctcaggaagc 120
ctcgg 125

<210> SEQ ID NO 165
<211> LENGTH: 125
<212> TYPE: DNA
<213> ORGANISM: Homo sapiens

<400> SEQUENCE: 165
tgataacaag aaattaaaat caaggtacag tatcatttat atgtagtagt acagagtaac 60
catgacttac taggtgttat gatgaaggtg tatgtgtgtg tatatgtgtg catgcatgta 120
gataa 125

<210> SEQ ID NO 166
<211> LENGTH: 125
<212> TYPE: DNA
<213> ORGANISM: Homo sapiens

<400> SEQUENCE: 166
acattaagga ccagccagaa aatggtaagt ttagcttggg actctagctg ctgctttcag 60
agtccacagc agccagcagg ccgactaagt gtgaggattt gggggcctac cctataagta 120
gccca 125

<210> SEQ ID NO 167
<211> LENGTH: 125
<212> TYPE: DNA
<213> ORGANISM: Homo sapiens

<400> SEQUENCE: 167
tttacccagc acatcctcta cgaggtaatt ttattggcag ctcttgaaga aattatgcta 60
catggttgca caccttgatt ttaactctgg gcccactatg gatttagcaa tgcgccttta 120
gtaat 125

<210> SEQ ID NO 168
<211> LENGTH: 125
<212> TYPE: DNA
<213> ORGANISM: Homo sapiens

<400> SEQUENCE: 168
tatagatgta tgaaaatcat cttacccttt tagtattatc tttttcatct tgttcctatt 60
gaaaagagat attgtatata tcattatata ttgtaaaatt ttactatctt atatacagta 120
atttt 125

<210> SEQ ID NO 169
<211> LENGTH: 125
<212> TYPE: DNA
<213> ORGANISM: Homo sapiens

<400> SEQUENCE: 169

-continued ggctcgcggg tgggtgggcg cctacctcgt gcggcgagcg cgggcagcag cgccaggcag 60
agcaggggcg ccaggagcgg cggcatgcct ccccaccggc tgccctctgc gcccgggcgg 120
cggcc 125

<210> SEQ ID NO 170
<211> LENGTH: 125
<212> TYPE: DNA
<213> ORGANISM: Homo sapiens

<400> SEQUENCE: 170
gtgcagggtg ggtcgggggg agcactcagg atccctccca ggggcaatgg gtgcagggtg 60
ggagtgggtg gaggggggag cactcaggat ccctcccggg gcaatgagtg cagggtgggt 120
ggaga 125

<210> SEQ ID NO 171
<211> LENGTH: 125
<212> TYPE: DNA
<213> ORGANISM: Homo sapiens

<400> SEQUENCE: 171
gctggggttg tcaagggaat gggaccttct gcagttggaa tgagggcgcg cagactggct 60
ggggagccat ttcttcatct gtagctcctg gggggcggag ggaactcttt ttccagacac 120
caaac 125

<210> SEQ ID NO 172
<211> LENGTH: 125
<212> TYPE: DNA
<213> ORGANISM: Homo sapiens

<400> SEQUENCE: 172
tttttaatct gcgacagagt ctcactctgt cacccaggcc ggagtgcagt ggcgtgatct 60
cagctaactg caacctccac ctcctgggtt caagcgattc ttgtgcctca gtctcccgag 120
tagca 125

<210> SEQ ID NO 173
<211> LENGTH: 125
<212> TYPE: DNA
<213> ORGANISM: Homo sapiens

<400> SEQUENCE: 173
gctcaagcaa tccgcctgcc ttggcctccc aaatggctgg gattacaggc aggagccacc 60
atgcctggcc tagcccctcc atctctagcc tttgtcagtt actaaacttt ttttcctgaa 120
gtttt 125

<210> SEQ ID NO 174
<211> LENGTH: 125
<212> TYPE: DNA
<213> ORGANISM: Homo sapiens

<400> SEQUENCE: 174
gttgccagaa aaccggggag gaaagtaagt aaatggcttt tctcttctga ccacacacca 60
gaagtccatt tgttgaatgc cgcacgatta ggacacacct cagtacactc caaaggcgcc 120
cctcg 125

<210> SEQ ID NO 175

<211> LENGTH: 125
<212> TYPE: DNA
<213> ORGANISM: Homo sapiens

<400> SEQUENCE: 175
aattacatat gaaaagataa cttactttat aaaatgtaga agaagatcag tcacgaattt 60
agcagatttc acaatagggc ttccaggctc attaaatgtt cgtgtattat gctctatata 120
tcgaa 125

<210> SEQ ID NO 176
<211> LENGTH: 125
<212> TYPE: DNA
<213> ORGANISM: Homo sapiens

<400> SEQUENCE: 176
ggggaggagg ggaagggcta ggggagggga ggaggggagg ggctagggga gggaaggggg 60
aggggagggg aggggagagt ggagggcaca gagcagcatc ttcttagtcc ctccccacat 120
ctggg 125

<210> SEQ ID NO 177
<211> LENGTH: 125
<212> TYPE: DNA
<213> ORGANISM: Homo sapiens

<400> SEQUENCE: 177
ctttcctttc cacatactta caaacctagg ggtggtggaa agggtatgga ttccggagtc 60
agatgttctg ggtttgaatc ccactcgcat ttcttagctg tgtgactttg agagagtttg 120
cttgg 125

<210> SEQ ID NO 178
<211> LENGTH: 125
<212> TYPE: DNA
<213> ORGANISM: Homo sapiens

<400> SEQUENCE: 178
tgatcagtac agaactgata ataggtgagc tcctcccggc agccttccct ggggggccta 60
ggaatgcctg cagctgctgt ggaatcccat gttgctcccc cacacctcac agtggaggtg 120
ggact 125

<210> SEQ ID NO 179
<211> LENGTH: 125
<212> TYPE: DNA
<213> ORGANISM: Homo sapiens

<400> SEQUENCE: 179
gtatttgact ttggttctgt aaggagtaat tgctgaagta cccagaggaa ttgatatttt 60
cagccacaag caatctcata gcccctgaga acattatagt aaggctctta ggcaaaagtt 120
ttttt 125

<210> SEQ ID NO 180
<211> LENGTH: 125
<212> TYPE: DNA
<213> ORGANISM: Homo sapiens

<400> SEQUENCE: 180
gcctgcgcat gctccatcgc ctgggtaggt ttccagggaa ggcagcgagc aggatcccct 60
actctgcggg cggcgcgagg cgtctggctc ttcgcggcgg cggcgagggg aaagggagcg 120
cgggg 125

<210> SEQ ID NO 181
<211> LENGTH: 125
<212> TYPE: DNA
<213> ORGANISM: Homo sapiens

<400> SEQUENCE: 181
gaagatggcg cctgttgtga cagggtaagt ctgagggaat cggagcgccg ggaaccggga 60
aagttgcggg cgtctggcag ctcacggcgg gcagcgggtt cgggggccgc ggcgcgcttg 120
gcgtt 125

<210> SEQ ID NO 182
<211> LENGTH: 125
<212> TYPE: DNA
<213> ORGANISM: Homo sapiens

<400> SEQUENCE: 182
acagtgaaaa gatgaagact tctggtaaat tgtttcacag cagtggaatt tgtacattag 60
ttttctacac ttgggagttg aaaaatggaa gaattatttg ccaaaagagg aggacaaaag 120
ataat 125

<210> SEQ ID NO 183
<211> LENGTH: 125
<212> TYPE: DNA
<213> ORGANISM: Homo sapiens

<400> SEQUENCE: 183
gcattagcta gagggggca cttaccaatc cgcccgatct tcatacccga gcgggcaagg 60
gctctgaggg ccgactgggc cccaggtcca ggggtcttgg tcctagaaaa tgaaggttta 120
agtta 125

<210> SEQ ID NO 184
<211> LENGTH: 125
<212> TYPE: DNA
<213> ORGANISM: Homo sapiens

<400> SEQUENCE: 184
ttaccaatcc gcccgatctt catacccgag cgggcaaggg ctctgagggc cgactgggcc 60
ccaggtccag gggtcttggt cctagaaaat gaaggtttaa gttaagaaga gcctttggcc 120
aagtc 125

<210> SEQ ID NO 185
<211> LENGTH: 125
<212> TYPE: DNA
<213> ORGANISM: Homo sapiens

<400> SEQUENCE: 185
ctaccagcca ccgagaccaa cagagtcagt gagtgctctc taaccacagt ctatgcagta 60
atagtaggtc cttcaaatat ttgctcattc tctttttgtt ttgtttcttt gcttttcaca 120
tgtta 125

<210> SEQ ID NO 186
<211> LENGTH: 125
<212> TYPE: DNA
<213> ORGANISM: Homo sapiens

<400> SEQUENCE: 186
tagatggacc tcgggaaccc agaagtaagt actccccttt ttattgaaga aagtaataga 60
gtttccagag accctatgag gaatttattc caaatgagtt agtgtcactt tcatgtccat 120
agtgt 125

<210> SEQ ID NO 187
<211> LENGTH: 125
<212> TYPE: DNA
<213> ORGANISM: Homo sapiens

<400> SEQUENCE: 187
gaggtggact agaatagagg gaaagtaagt caaaacaaaa tgtgtaataa gccctcaaca 60
tggatctttt ttatggttag atttttgttt atagtagtta ggctcgaatg ttcttaatgg 120
tctca 125

<210> SEQ ID NO 188
<211> LENGTH: 125
<212> TYPE: DNA
<213> ORGANISM: Homo sapiens

<400> SEQUENCE: 188
ccagcccccc tcaccccacg cccacccgcc aaaagggagg agtcgagagg caactccacg 60
ctcggcagcg gaaccagggc gctgcgcccg gccagcgcct cccacagccg ccctcccttc 120
aacac 125

<210> SEQ ID NO 189
<211> LENGTH: 125
<212> TYPE: DNA
<213> ORGANISM: Homo sapiens

<400> SEQUENCE: 189
ccgagatccg ctgcccacga cttacctctt ggcaccttga agcgcgagag acaggggagc 60
tttgcaaatt gcaggaggga gtggatgcaa agaggtggct gtgagagggc gagaagaaaa 120
gaagg 125

<210> SEQ ID NO 190
<211> LENGTH: 125
<212> TYPE: DNA
<213> ORGANISM: Homo sapiens

<400> SEQUENCE: 190
ttgggaaagc aaagcaggga gacaccttca gaagaagctt gtctgagctt caccgcagct 60
cccaccacgc ggcgcttcag tacggctgga tcctccgcag gcgagcggaa ggcccccagg 120
aggag 125

<210> SEQ ID NO 191
<211> LENGTH: 125
<212> TYPE: DNA
<213> ORGANISM: Homo sapiens

<400> SEQUENCE: 191
cgaggcggaa agaggaaaca caaaccgcag gcccccgctc agcccccaca gcagtcgccc 60
ccgcagcagc cccttcccca ggaagaggag gtgaaagcca aaaggcagag gaagtcccga 120
gggag 125

<210> SEQ ID NO 192
<211> LENGTH: 125
<212> TYPE: DNA
<213> ORGANISM: Homo sapiens

<400> SEQUENCE: 192
catgcaactt tcctttttcc tgtccccctc ccaccaaaaa aaaatccatt cctaataaac 60
agctatcatg tttcactcca tgtgttcagt ggtacaaaac ctatataaaa tatgtacagc 120
tcttt 125

<210> SEQ ID NO 193
<211> LENGTH: 125
<212> TYPE: DNA
<213> ORGANISM: Homo sapiens

<400> SEQUENCE: 193 tttttttttac taacaatctg gtttccgctg ggcgcggtgg ctcacgcctg taatcccagc 60
actttgggag ggcgaggtgg gcggatcacg aggtcaggag atcgagacca tcctcgctaa 120
cacgg 125

<210> SEQ ID NO 194
<211> LENGTH: 125
<212> TYPE: DNA
<213> ORGANISM: Homo sapiens

<400> SEQUENCE: 194
aggcttagaa gatgtactgc caaggtctct gtttggatat actgttaggg aaaggaaaca 60
tacatgtgta agactggcct aaaggcaaaa aagttcatca gtccctttttt tttttttttt 120 ttttt 125

<210> SEQ ID NO 195
<211> LENGTH: 125
<212> TYPE: DNA
<213> ORGANISM: Homo sapiens

<400> SEQUENCE: 195
atttgattat gagtatagta actggtaaga cctcagaaac ctttcctaac aggaatatcc 60
atgtcttaca tattaagcta ttcactctat ttaaagtctg ctcttgtttc ttgccttttc 120
ctttg 125

<210> SEQ ID NO 196
<211> LENGTH: 125
<212> TYPE: DNA
<213> ORGANISM: Homo sapiens

<400> SEQUENCE: 196
gagaacctag ctcatagcag gagggtgagt actgtctgac attactttgc tccttctcat 60
tcctgctacc tccatcatgt gaacctcttc tgttctcttg actttgtatc atctcattga 120
tttga 125

<210> SEQ ID NO 197
<211> LENGTH: 125
<212> TYPE: DNA
<213> ORGANISM: Homo sapiens

<400> SEQUENCE: 197
agcccttcca gatacagcta ccaggtgaga tgagaaattg ctggtctcta gccataggag 60
tgtgttctgg gtcccaaatt gtcctggtca tcctttgcca ttgagatgct gtctttgcat 120
atagt 125

<210> SEQ ID NO 198
<211> LENGTH: 125
<212> TYPE: DNA
<213> ORGANISM: Homo sapiens

<400> SEQUENCE: 198
tgacagctga gctcgaggaa cttggtgagt ggcgggggtg gcggtggagg tggacgcagg 60
tggacggtcc atgatgggca gacagggccg ggagacacag gtggtacggg agggcaggcg 120
gtcca 125

<210> SEQ ID NO 199
<211> LENGTH: 125
<212> TYPE: DNA
<213> ORGANISM: Homo sapiens

<400> SEQUENCE: 199
tgctgggatt acaggaatga gataccatgg ctggcctctt cttagtttga ttacatttgc 60
agggatcctg tttccaaata agatcacatt cacaggttca gggtagacat gagttttggt 120
gggat 125

<210> SEQ ID NO 200
<211> LENGTH: 125
<212> TYPE: DNA
<213> ORGANISM: Homo sapiens

<400> SEQUENCE: 200
ccgggagccc acgtcccgca gcaccctcca gcctgcagag gcttcgggtg ggggagggag 60
cgggcctgtc ctagaggctg gctcctggca tctgtcttct gcccaccgcc tgcagggagt 120
tgctt 125

<210> SEQ ID NO 201
<211> LENGTH: 125
<212> TYPE: DNA
<213> ORGANISM: Homo sapiens

<400> SEQUENCE: 201
cgcccgcagg ccccggaacc accggcccgg cgcactgccg ctcatgagcg ccttcgcgcg 60
ctcgcggaac cccgtggctt ccccgacgca gcccagcggc acggagaaag gtagggccgg 120
ggtcg 125

<210> SEQ ID NO 202
<211> LENGTH: 125
<212> TYPE: DNA
<213> ORGANISM: Homo sapiens

<400> SEQUENCE: 202
acagccccga agttcgccgg gcccggccac cctgccccaa gggcaagcaa ggaatacgtt 60
cccccagccc caggggccac cgcggctctc cccttcccca gcctcgaagc catgggggcc 120
ccctc 125

<210> SEQ ID NO 203
<211> LENGTH: 125
<212> TYPE: DNA
<213> ORGANISM: Homo sapiens

<400> SEQUENCE: 203
gtcactgcct accagaacca tcgggtgagg gcctgtgggg aggacctgag cggattcaac 60
gcctctggaa aagcgggtgt aattttcagt tgccgtttgg ggacagtggg tccgcttaga 120
cctgc 125

<210> SEQ ID NO 204
<211> LENGTH: 125
<212> TYPE: DNA
<213> ORGANISM: Homo sapiens

<400> SEQUENCE: 204
ctagctccaa aatgtggcac ctaaggagtg aggtctagaa gttggcagat gtaagactca 60
gccaccagat cctgccacct tcctccacag ggtgctacag aaggcaactg aggtttcaaa 120
atcac 125

<210> SEQ ID NO 205
<211> LENGTH: 125
<212> TYPE: DNA
<213> ORGANISM: Homo sapiens

<400> SEQUENCE: 205
tcatgcctgt aaatctcagc actttgggag gccgaggcag gagaatgatt tgagcccagg 60
agtaagagac cagcctccgt aacaaagtga gacctcgtct ccacaaaaaa aattttttaa 120
atcag 125

<210> SEQ ID NO 206
<211> LENGTH: 125
<212> TYPE: DNA
<213> ORGANISM: Homo sapiens

<400> SEQUENCE: 206
gtgtgtgtgt gtgtgtatat atatgtgtgt gtgtgtgtgt atatatatgt gtgtgtatat 60
atatatatat atacacacac acacacatat atatatgatg gctgggctta gcagatgtgt 120
agatt 125

<210> SEQ ID NO 207
<211> LENGTH: 125
<212> TYPE: DNA
<213> ORGANISM: Homo sapiens

<400> SEQUENCE: 207
gtgtgtgtgt gtgtgtatat atatgtgtgt gtatatatat atatatatac acacacacac 60
acatatatat atgatggctg ggcttagcag atgtgtagat tctcctattg ctgggtccca 120
ctttt 125

<210> SEQ ID NO 208
<211> LENGTH: 125
<212> TYPE: DNA
<213> ORGANISM: Homo sapiens

<400> SEQUENCE: 208
gcggaggcgg gtggctgttc tcgggtaggc gtcgcgcgtg gggcggcact gtgggagttc 60
ccgaggccga ggtcgttcgc aggccccatt tccctgcgct cttattcgtg ttgccgcttc 120
ttggc 125

<210> SEQ ID NO 209
<211> LENGTH: 125
<212> TYPE: DNA
<213> ORGANISM: Homo sapiens

<400> SEQUENCE: 209
aacactaaga aaagaattta catacttgag ccagtaaaat gtccacttgc caaagaagtt 60
ggtccatttt tcccactgct cacaggaggt gaaaacatct aaaagaaaca aagaaatatt 120
acagt 125

<210> SEQ ID NO 210
<211> LENGTH: 125
<212> TYPE: DNA
<213> ORGANISM: Homo sapiens

<400> SEQUENCE: 210
aagctaataa ctagctattt agagaacaca gaaacacttg acagtcatct atcagatagc 60
atttccttta atgcctaaaa gaaccttcct ttatgcaaca gacattaaaa ggaggttaaa 120
cctta 125

<210> SEQ ID NO 211
<211> LENGTH: 125
<212> TYPE: DNA
<213> ORGANISM: Homo sapiens

<400> SEQUENCE: 211
attagccggg cgtggtggct tttgcctgta atcccagcta ttcgggaggc tgaggcaaga 60
gaatcgcttg aaccctggag gcggaggctg cggtgagccg aggttgcggc attgcactcc 120
agcct 125

<210> SEQ ID NO 212
<211> LENGTH: 125
<212> TYPE: DNA
<213> ORGANISM: Homo sapiens

<400> SEQUENCE: 212
cggtcggggg aagagacctg acaggtacgg gtcaccgccg ccccctgccc tccgcgggcg 60
ccgaggcggg gaccggctcc cgcagccccg gtgaacgggc cgcccgctct gggccggctc 120
cagcc 125

<210> SEQ ID NO 213
<211> LENGTH: 125
<212> TYPE: DNA
<213> ORGANISM: Homo sapiens

<400> SEQUENCE: 213
tgcctgaaat tttcttttgt tgcagaagga atctggagag gaggtagaaa ttgaggaatt 60
ctatgtgaaa tacaaaaact tgtaagtaaa ttgtgattct gtttttaatg gggggctata 120
ttttc 125

<210> SEQ ID NO 214
<211> LENGTH: 125
<212> TYPE: DNA
<213> ORGANISM: Homo sapiens

<400> SEQUENCE: 214
gttttcactg tcttctctgt cttagttaat gtcagctttg tctgtccagc tgctcaggct 60 aaaactttc tttcatataa cacatcctat cagcagctcc tgtttgtggg taggcatttt 120
gcctt 125

<210> SEQ ID NO 215
<211> LENGTH: 125
<212> TYPE: DNA
<213> ORGANISM: Homo sapiens

<400> SEQUENCE: 215
tacaccactg cactccagcc tgggcgacag agcgaggaga ccccaccccc cacccccttac 60 cacctccccc ccaccaaaaa aaaaagagaa aaattaattg accataaata tgtgagtctg 120
tttct 125

<210> SEQ ID NO 216
<211> LENGTH: 125
<212> TYPE: DNA
<213> ORGANISM: Homo sapiens

<400> SEQUENCE: 216
cccccgctaa tttttctatt tttagtacag acggggtttc accatgttgg gcaagatcgt 60
cttgaactcc tgatctcagg tgatccgcct gcctaggcct ctcaaagtgc tgagattaca 120
ggcgt 125

<210> SEQ ID NO 217
<211> LENGTH: 125
<212> TYPE: DNA
<213> ORGANISM: Homo sapiens

<400> SEQUENCE: 217
tgtcatatca ctgcatggac agcaggtgtg tgaaggtttg tgtcatccac cgagtctgcc 60
ctgactgaac tggtcacatc cgcggatggc cgtggtgacc tcttctgagc tctgatctgc 120
tattg 125

<210> SEQ ID NO 218
<211> LENGTH: 125
<212> TYPE: DNA
<213> ORGANISM: Homo sapiens

<400> SEQUENCE: 218
gacggctgtt gtttctctct aacaggcagt tccggcgagg ggggagcctc agcaggattg 60
ctgtgtgaaa accgagctgc tgggagaagg tgagggcggt gtgcaccgag ggacaggagc 120
agcgc 125

<210> SEQ ID NO 219
<211> LENGTH: 125
<212> TYPE: DNA
<213> ORGANISM: Homo sapiens

<400> SEQUENCE: 219
tcctccacac cagggcacag tcgaggtgcc gaaccccctc cacaccaggg cacagtcgag 60
gtgccgaacc ccctccacac cagggcacag tcgaggtgcc gaaccccctc cacaccagga 120
cacag 125

<210> SEQ ID NO 220
<211> LENGTH: 125
<212> TYPE: DNA

<213> ORGANISM: Homo sapiens

<400> SEQUENCE: 220
ccctccacac cagggcacag tcgaggtgcc gaaccccctc cacaccaggg cacagtcgag 60
gtgccgaacc ccctccacac caggacacag tcgaggtgcc gaaccccctt cacaccaggg 120
cacag 125

<210> SEQ ID NO 221
<211> LENGTH: 125
<212> TYPE: DNA
<213> ORGANISM: Homo sapiens

<400> SEQUENCE: 221
ttaataaaac tgtgtttgtt cacagtggac ggaattgacc ccaacttcaa aatggagcac 60
cagaataagc gctctccact gcacgccgcg gcagaggctg gacacgtgga catctgccac 120
atgct 125

<210> SEQ ID NO 222
<211> LENGTH: 125
<212> TYPE: DNA
<213> ORGANISM: Homo sapiens

<400> SEQUENCE: 222
cgccgtgtac cgagaccgta gagaggccga ttgaggggcg ccatgtaccg agaccgtaga 60
gaggccgact gaggggcgcc gtgtaccgag accgtagaga ggccgactga ggggcgccgt 120
gtacc 125

<210> SEQ ID NO 223
<211> LENGTH: 125
<212> TYPE: DNA
<213> ORGANISM: Homo sapiens

<400> SEQUENCE: 223
ccccacagca cgtgcactcc acgactgcac ccaagacgcc gcccacagca cgtgcactca 60
cctccaccca agacgccccc cacagcacgt gcactggact cctcccaaga cgccccgcac 120
agcac 125

<210> SEQ ID NO 224
<211> LENGTH: 125
<212> TYPE: DNA
<213> ORGANISM: Homo sapiens

<400> SEQUENCE: 224
gccgcccaca gcacgtgcac tcacctccac ccaagacgcc ccccacagca cgtgcactgg 60
actcctccca agacgccccg cacagcacgt gcactcgact cctcccaaga cgccccgcac 120
agcac 125

<210> SEQ ID NO 225
<211> LENGTH: 125
<212> TYPE: DNA
<213> ORGANISM: Homo sapiens

<400> SEQUENCE: 225
ctcccagact tctcacactc acccctccca gacttctcac actcaccccc tcccagactt 60
ctcacactca cccctcccag acttctcaca ctcacccctc ccagacttct cacactcgcc 120
ccctc 125

<210> SEQ ID NO 226
<211> LENGTH: 125
<212> TYPE: DNA
<213> ORGANISM: Homo sapiens

<400> SEQUENCE: 226
tcccagactt ctcacactca ccccctccca gacttctcac actcacccct cccagacttc 60
tcacactcac ccctcccaga cttctcacac tcgccccctc ccagacttct cacactcacc 120
cctcc 125

<210> SEQ ID NO 227
<211> LENGTH: 125
<212> TYPE: DNA
<213> ORGANISM: Homo sapiens

<400> SEQUENCE: 227
ttctcacact cacccccctcc cagacttctc acactcaccc ctcccagact tctcacactc 60
acccctccca gacttctcac actcgccccc tcccagactt ctcacactca cccctcccag 120
acttc 125

<210> SEQ ID NO 228
<211> LENGTH: 125
<212> TYPE: DNA
<213> ORGANISM: Homo sapiens

<400> SEQUENCE: 228
ctcccagact tctcacactc acccctccca gacttctcac actcacccct cccagacttc 60
tcacactcgc cccctcccag acttctcaca ctcacccctc ccagacttct cacactcacc 120
ccctc 125

<210> SEQ ID NO 229
<211> LENGTH: 125
<212> TYPE: DNA
<213> ORGANISM: Homo sapiens

<400> SEQUENCE: 229
tcccagactt ctcacactcg ccccctccca gacttctcac actcacccct cccagacttc 60
tcacactcac cccctcccag acttctcaca ctcacccctc ccagacttct cacactcacc 120
ccctc 125

<210> SEQ ID NO 230
<211> LENGTH: 125
<212> TYPE: DNA
<213> ORGANISM: Homo sapiens

<400> SEQUENCE: 230
ctcccagact tctcacactc acccctccca gacttctcac actcaccccc tcccagactt 60
ctcacactca cccctcccag acttctcaca ctcacccccct cccctctcac cccctcccac 120
gcctc 125

<210> SEQ ID NO 231
<211> LENGTH: 125
<212> TYPE: DNA
<213> ORGANISM: Homo sapiens

<400> SEQUENCE: 231
ttctcacact cacccccctcc cagacttctc acactcaccc ctcccagact tctcacactc 60
accccctccc ctctcacccc ctcccacgcc tcaccccctc ccacgcctct cacccccctcc 120 cacgc 125

<210> SEQ ID NO 232
<211> LENGTH: 125
<212> TYPE: DNA
<213> ORGANISM: Homo sapiens

<400> SEQUENCE: 232
gtaccgagac tgtagagagg ccgacttagg ggcgccgtgt accgagaccg tagagaggcc 60
gactgagggg cgccatgtac cgagaccgta gagaggccga ctgaggggcg ccgtgtaccg 120
agacc 125

<210> SEQ ID NO 233
<211> LENGTH: 125
<212> TYPE: DNA
<213> ORGANISM: Homo sapiens

<400> SEQUENCE: 233
ctcacccctc ccagacttct cacactcacc ccctcccaga cttctcacac tcacccctcc 60
cagacttctc acactcaccc cctcccctct cacccccctcc cacgcctcac cccctcccac 120
gcctc 125

<210> SEQ ID NO 234
<211> LENGTH: 125
<212> TYPE: DNA
<213> ORGANISM: Homo sapiens

<400> SEQUENCE: 234
cctctgctca ggcctcccta gcacctcccc ctaaccaaat tctccctgga ccccattctg 60
agctccccat caccatggga ggtggggcct caatctaagg ccttccctgt cagaaggggg 120
ttgtg 125

<210> SEQ ID NO 235
<211> LENGTH: 125
<212> TYPE: DNA
<213> ORGANISM: Homo sapiens

<400> SEQUENCE: 235
gtatcctggg tcatcttgtc cacaggtaac aactccgtgg gtgccatcca gtgccctgat 60
agtcagttcg aatgcccgga cttctccacg tgctgtgtta tggtcgatgg ctcctggggg 120
tgctg 125

<210> SEQ ID NO 236
<211> LENGTH: 125
<212> TYPE: DNA
<213> ORGANISM: Homo sapiens

<400> SEQUENCE: 236
acgccctttc ctgcccaccc cccaggctgt ctgctgctcg gaccaccagc actgctgccc 60
ccagggctac acgtgtgtag ctgaggggca gtgtcagcga ggaagcgaga tcgtggctgg 120
actgg 125

<210> SEQ ID NO 237
<211> LENGTH: 125

<212> TYPE: DNA
<213> ORGANISM: Homo sapiens

<400> SEQUENCE: 237
agcggccagg cgttcctcca gaacctcctc tgccaggagc ttgctacaag tgccagaaat 60
ctggccacca ggccaaggaa tgcctgcagc ccaggattcc tcctaagtca cgtcccatct 120
gtgca 125

<210> SEQ ID NO 238
<211> LENGTH: 125
<212> TYPE: DNA
<213> ORGANISM: Homo sapiens

<400> SEQUENCE: 238
attcagcata gttttctgtt cttagataaa aatatgatag tacacctact gcctagtaga 60
ctgtgagcct tttgaaggta aggatcatat ttttatgtgt gtttgtaccc cctacacctt 120
gcaca 125

<210> SEQ ID NO 239
<211> LENGTH: 125
<212> TYPE: DNA
<213> ORGANISM: Homo sapiens

<400> SEQUENCE: 239
tctccgcccc tggcctcggg gacgcggcgg caccttcaca ctttccgctt ggcccgctgc 60
tcgcctttca ggccgccgcg ttttcaattg ttaatttgga aacggaaaaa gtagccggcc 120
gggcg 125

<210> SEQ ID NO 240
<211> LENGTH: 125
<212> TYPE: DNA
<213> ORGANISM: Homo sapiens

<400> SEQUENCE: 240
catggagtgt ttgttcaaaa tgcagatacc tggacctgtc tccaagccca caggatcaga 60
atctctggag aagagacaca gccttctgca tatgtaacat ggtccccagg ggatccctat 120
gcaaa 125

<210> SEQ ID NO 241
<211> LENGTH: 125
<212> TYPE: DNA
<213> ORGANISM: Homo sapiens

<400> SEQUENCE: 241
ttctaatcta atgtgcactc cacaggaacc ctattctgtc aacagacctg gattctgata 60
tcaatgaaat agtgcacatc ttgaaaacat ttccactaat gtaaacaaga aagatgaaag 120
tcaac 125

<210> SEQ ID NO 242
<211> LENGTH: 125
<212> TYPE: DNA
<213> ORGANISM: Homo sapiens

<400> SEQUENCE: 242
attaatttcc ttcttttccc ctcagtaaat atcgtgcagt cactcagtgc ttatccttta 60
aacagcagtt gtgtgattgt ttcctggata ctatcaccca gtgattacaa gctaatgtat 120
tttat 125

<210> SEQ ID NO 243
<211> LENGTH: 125
<212> TYPE: DNA
<213> ORGANISM: Homo sapiens

<400> SEQUENCE: 243
tgggtgatgg ttgagggagg gatgctgtgg aatgaaggaa taacattcag gatggcatag 60
catgaacaaa accaggaagt gaaaataaat gcaaagatgc tcttaagtca ctgtgagttc 120
tctgc 125

<210> SEQ ID NO 244
<211> LENGTH: 125
<212> TYPE: DNA
<213> ORGANISM: Homo sapiens

<400> SEQUENCE: 244
ggggtctgga gggctttaag atgagggcga aacaaggacc acccatgatt ccaaagaata 60
tccggaactt gcttgttgtc tgttggtgcc tttctttcag ctcattccta gagggcggac 120
agagg 125

<210> SEQ ID NO 245
<211> LENGTH: 125
<212> TYPE: DNA
<213> ORGANISM: Homo sapiens

<400> SEQUENCE: 245
aaggtcagac ctcaaggaag tagagaaaca agaacaaacc aaatccaaac ccaacagaag 60
aaaagaaata acaaagatca gagcagaact aaatgaaatt gaaacacaaa acaatacaaa 120
agaaa 125

<210> SEQ ID NO 246
<211> LENGTH: 125
<212> TYPE: DNA
<213> ORGANISM: Homo sapiens

<400> SEQUENCE: 246
gagaaagaaa ccaaaagcct cttagcaaca cagacccttt gctgctgctg ttgctgctgc 60
tgctgctgtt gctgctgctg ctgctactgc tgctgctgct actgctgctg cttggccctg 120
gctgg 125

<210> SEQ ID NO 247
<211> LENGTH: 125
<212> TYPE: DNA
<213> ORGANISM: Homo sapiens

<400> SEQUENCE: 247
attctttttt tctctttcac atcagatgca actccagtag taccttctcg ggcagcaact 60
ccaagatcag taagaaataa gtctcatgaa ggaattacaa attctgtaat gcctgaatgt 120
aagaa 125

<210> SEQ ID NO 248
<211> LENGTH: 125
<212> TYPE: DNA
<213> ORGANISM: Homo sapiens

<400> SEQUENCE: 248
caaggtcaac aatagggtcc ccaaggccat caatgccatc aagcccttct accaagtccg 60
atggacatca tcagtacaag gatatcccta acccattaat tgctggaata agtaatgtac 120
taaat 125

<210> SEQ ID NO 249
<211> LENGTH: 125
<212> TYPE: DNA
<213> ORGANISM: Homo sapiens

<400> SEQUENCE: 249
ttttcttttt ccaaatactc tgcagaatgg cggctccaga ggcggtttca agtttcataa 60
gtcaggtaac actgtgggtt tccgccttct cggacgcggg gaaaggggag acaggaggct 120
tcccc 125

<210> SEQ ID NO 250
<211> LENGTH: 125
<212> TYPE: DNA
<213> ORGANISM: Homo sapiens

<400> SEQUENCE: 250
gcggcctggg gatcaccttc ttcagaatga aaggaggggt ggttaagtgc tgattcttgg 60
gccccacccg aagctactga atcggcgctc tgggcacctt agatgaaccc gtgcgcccgc 120
cgtct 125

<210> SEQ ID NO 251
<211> LENGTH: 125
<212> TYPE: DNA
<213> ORGANISM: Homo sapiens

<400> SEQUENCE: 251
aaactaaaat ctgtttcttt ttcaggagga gttggaagat gaggagtaac acaacacttt 60
agatatacat gttaaaaact tataacaaat catagatcat actaaaggat taccgaagtt 120
tagaa 125

<210> SEQ ID NO 252
<211> LENGTH: 125
<212> TYPE: DNA
<213> ORGANISM: Homo sapiens

<400> SEQUENCE: 252
ctttgtgttt tgaaaatctc tttagtgtgc tgggccgatg gccacatttt ctgctgtgta 60
tatgtgatat caaactttaa caagtctgtt gcaacaagga taagacacag cagtaggaaa 120
agacc 125

<210> SEQ ID NO 253
<211> LENGTH: 125
<212> TYPE: DNA
<213> ORGANISM: Homo sapiens

<400> SEQUENCE: 253
cttaccagtt gatccttctt gccaggaatg ccatctccaa ccacactgaa gaagtcggag 60
aagtctggtt tcagcagccc ctccccttca cagacctcct ccctgggaac ggcgttcaca 120
cagca 125

<210> SEQ ID NO 254

<211> LENGTH: 125
<212> TYPE: DNA
<213> ORGANISM: Homo sapiens

<400> SEQUENCE: 254
tgctgacctt cttccattcc gtggctgaaa aataatagat tagaaataaa tcagtgtaac 60
taaagatgca agctaacagt catagaaaca gattgatgat ttagaggagt gtttaacgtg 120
catca 125

<210> SEQ ID NO 255
<211> LENGTH: 125
<212> TYPE: DNA
<213> ORGANISM: Homo sapiens

<400> SEQUENCE: 255
gggcccacga aggccccgcc acagctgttg gcagatgtgc cagggcagtt agttcccacc 60
tgcttcccca gcgcccccgc cactcagcac cgggaacctg tcatgggcac agccgcctcc 120
cccca 125

<210> SEQ ID NO 256
<211> LENGTH: 125
<212> TYPE: DNA
<213> ORGANISM: Homo sapiens

<400> SEQUENCE: 256
gcagggtggg tggagagggg agcactcagg atccctcctg gggcaatggg tgcagggtgg 60
gtcgggggga gcactcagga tccctcccag gggcaatggg tgcagggtgg gagtgggtgg 120
agggg 125

<210> SEQ ID NO 257
<211> LENGTH: 125
<212> TYPE: DNA
<213> ORGANISM: Homo sapiens

<400> SEQUENCE: 257
gtgggggccg gggagggagg gggcctgctg cccacaggct gggcagtcgg cacaggcagg 60
agccgggctg gggttgtcaa gggaatggga ccttctgcag ttggaatgag ggcgcgcaga 120
ctggc 125

<210> SEQ ID NO 258
<211> LENGTH: 125
<212> TYPE: DNA
<213> ORGANISM: Homo sapiens

<400> SEQUENCE: 258 ttgtttttg agatagagtc cagcctggag tgctgtggca tgatcttggc acacttgcaa 60
cctctgcctc ctgggttcag gtgattctcc tcctctagcc tcctccacgc ctggctaata 120
tttgt 125

<210> SEQ ID NO 259
<211> LENGTH: 125
<212> TYPE: DNA
<213> ORGANISM: Homo sapiens

<400> SEQUENCE: 259
ctgtataggt tagtatatcc atgactcccg tcaactttct aaatgttcgc tgggtgcagt 60
ggctcatgcc tgtaatccca gcactttggg aggctgaggc ggctggatca cctgaggtca 120
gtagt 125

<210> SEQ ID NO 260
<211> LENGTH: 125
<212> TYPE: DNA
<213> ORGANISM: Homo sapiens

<400> SEQUENCE: 260
gtacgctaga ctcttcttga cttagggaaa gtgctgaaag tcagagctca tcaataaaat 60
ctgcgcgacc tgaactcgct gctgactggc cgcgtcgccg cagcccctgg cagccgggac 120
agtga 125

<210> SEQ ID NO 261
<211> LENGTH: 125
<212> TYPE: DNA
<213> ORGANISM: Homo sapiens

<400> SEQUENCE: 261
taatcttctt ctaggctgat ggtcctgtga taaaagtgtt caaatatatt aataaaagag 60
cacttacaca ataaaatttg tacttttaat gtagtcttag ataattgggt aatatacaat 120
aattc 125

<210> SEQ ID NO 262
<211> LENGTH: 125
<212> TYPE: DNA
<213> ORGANISM: Homo sapiens

<400> SEQUENCE: 262
gaggggagag tggagggcac agagcagcat cttcttagtc cctccccaca tctgggcccc 60
tctttacacc ctgggtcccc cgagaggcac cctgcgttca cacaggacag aacggctgag 120
gctac 125

<210> SEQ ID NO 263
<211> LENGTH: 125
<212> TYPE: DNA
<213> ORGANISM: Homo sapiens

<400> SEQUENCE: 263
tgaacttgcc tgaatgagtt tcctctggaa tacaaggaag tcatatgaaa tcgcagttta 60
ggcagtgcat tcaagagtac atggcagaca tcgtttcgtg ttaataacta tatcctgccc 120
tttac 125

<210> SEQ ID NO 264
<211> LENGTH: 125
<212> TYPE: DNA
<213> ORGANISM: Homo sapiens

<400> SEQUENCE: 264
cctcccttcc tttttctttt cacagataac cagcccgagt catgcagtct tttcgagaaa 60
ggtgtggttt ccatggcaaa caacagaact accagcagac ctcgcaggaa acatcacgcc 120
tagag 125

<210> SEQ ID NO 265
<211> LENGTH: 125
<212> TYPE: DNA
<213> ORGANISM: Homo sapiens

<400> SEQUENCE: 265
gctgccacag gtaaacgtta acttcagtaa cttccttatt tcctcccact atcagttttt 60
cttattttct tattattatt attattgttt tcgagatgaa gttttgctct gtcacccagg 120
ctgga 125

<210> SEQ ID NO 266
<211> LENGTH: 125
<212> TYPE: DNA
<213> ORGANISM: Homo sapiens

<400> SEQUENCE: 266
cagtaatatt tgtatttgtt tttagggaag ctatgcgaaa ttatttaaaa gagcgagggg 60
atcaaacagt acttattctt catgcaaaag ttgcacagaa gtcatatgga aatgaaaaaa 120
ggtaa 125

<210> SEQ ID NO 267
<211> LENGTH: 125
<212> TYPE: DNA
<213> ORGANISM: Homo sapiens

<400> SEQUENCE: 267
gtttctttct ttgtttttga gacagggtct tgctctgtca tccaggctag agtggactgg 60
tgcgatctca gctcactgca gcctcgactt cctggactca agtgatcctc ttacctcagc 120
ctcct 125

<210> SEQ ID NO 268
<211> LENGTH: 125
<212> TYPE: DNA
<213> ORGANISM: Homo sapiens

<400> SEQUENCE: 268
attttcttta tttttttttt tccaggaaat ttggtgagcg gcctccacct aaacgactta 60
ctaggtgagt attatattag tcagcttttt acacatacat tttatgaaag tataaatctt 120
attgt 125

<210> SEQ ID NO 269
<211> LENGTH: 125
<212> TYPE: DNA
<213> ORGANISM: Homo sapiens

<400> SEQUENCE: 269
cggcgacccc ccttcctgcg agtgctgtca gaggggatgg gggtgacatc ctctgtgggg 60
aggaagagaa agcgtcattg cctggagctg gatgggaagg gcccccagga ctccctagac 120
caatg 125

<210> SEQ ID NO 270
<211> LENGTH: 125
<212> TYPE: DNA
<213> ORGANISM: Homo sapiens

<400> SEQUENCE: 270
cagaggggat gggggtgaca tcctctgtgg ggaggaagag aaagcgtcat tgcctggagc 60
tggatgggaa gggcccccag gactccctag accaatggcc taaccaatca gcaacagatc 120
ctgct 125

<210> SEQ ID NO 271
<211> LENGTH: 125
<212> TYPE: DNA
<213> ORGANISM: Homo sapiens

<400> SEQUENCE: 271
gtttgggtat ggtttgtatt ttcagtttaa ggctgcaagc agtatttaca acagagggta 60
caagttctat ctgaaaaaaa aaggagggac tatggcatca aacagcctct tcagcacagt 120
gacac 125

<210> SEQ ID NO 272
<211> LENGTH: 125
<212> TYPE: DNA
<213> ORGANISM: Homo sapiens

<400> SEQUENCE: 272
actttctttc catctcttgc ctcagatgca tttgagcctc gcccagagcc cagcttgata 60
gaaaaatgcc agacttgggt tgaatcagtc aattaaaaac cagctcttct tgtagtttga 120
gagac 125

<210> SEQ ID NO 273
<211> LENGTH: 125
<212> TYPE: DNA
<213> ORGANISM: Homo sapiens

<400> SEQUENCE: 273
agatttttct ttttcttttt cccagacccc aggcaggcac agtcttcccc gccgtggtcc 60
tatgaccagt cttacccctc ctacctgagc cagatgacgt ccccgtccat ccactctacc 120
acccc 125

<210> SEQ ID NO 274
<211> LENGTH: 125
<212> TYPE: DNA
<213> ORGANISM: Homo sapiens

<400> SEQUENCE: 274
tggactagct gccgtattat tcatctaaat aaaaaggaga aataaagctt acaaaatgta 60
cctagctata agtaaatgca aaaaaaaaag aaagcaaata taaattactt caaaaagtag 120
agaaa 125

<210> SEQ ID NO 275
<211> LENGTH: 125
<212> TYPE: DNA
<213> ORGANISM: Homo sapiens

<400> SEQUENCE: 275
cacgcctttc ctcagaaaat attgctatca aaaaaaaagt tttaattgta gtgaagttaa 60
tcacaaaaag tgagttaaac aaaatgcact gaacatgcta ctgggtttct agttagatct 120
catat 125

<210> SEQ ID NO 276
<211> LENGTH: 125
<212> TYPE: DNA
<213> ORGANISM: Homo sapiens

<400> SEQUENCE: 276
aatcttaggt agatggataa gcaactataa cagacaaaca tatatgcaaa ttggtgggag 60
ggaaccaaag acatctgagc agacttcaga actacagttt gaaaatcact aatttcctcc 120
aaatc 125

<210> SEQ ID NO 277
<211> LENGTH: 125
<212> TYPE: DNA
<213> ORGANISM: Homo sapiens

<400> SEQUENCE: 277
cctacaaaga gggggttcct tgtcctaggg gtggggagag caagaggacg cgacctggcg 60
agattgcccc tagtctgggg ccgcctctag gcttcggaaa ctgcacacgg cgcgcggggg 120
gctcc 125

<210> SEQ ID NO 278
<211> LENGTH: 125
<212> TYPE: DNA
<213> ORGANISM: Homo sapiens

<400> SEQUENCE: 278
aacaagatcc tgaaggccaa gcggctgcag agacaatcaa aaacaggcaa caacttcgtg 60
aagaagaggc gcgggcgtcc caggaagcag cccacccagt tcgatgagga ctccagagac 120
caaat 125

<210> SEQ ID NO 279
<211> LENGTH: 125
<212> TYPE: DNA
<213> ORGANISM: Homo sapiens

<400> SEQUENCE: 279
ccggtgctgg aaaaatgcat cgacctgccc agcaaaagag gccagaagcc cagcctgagc 60
ccgctggtgc tggagcccgc cgccagccaa gacaccatca tggccaccat cgaggcggtc 120
atcca 125

<210> SEQ ID NO 280
<211> LENGTH: 125
<212> TYPE: DNA
<213> ORGANISM: Homo sapiens

<400> SEQUENCE: 280
aatactgacc tgcattcttg atgtacccct cccccgttcc catcttgcag acacttttaa 60
gtaataaaat gcatgcacct cactaacaga gaatactttc ctctgtctaa agttcttcac 120
ttaga 125

<210> SEQ ID NO 281
<211> LENGTH: 125
<212> TYPE: DNA
<213> ORGANISM: Homo sapiens

<400> SEQUENCE: 281
aaagtactgg gattacaggc gtgagccact gcacccatcc tgtttttctt tcatattaaa 60
gtttcaaaat aactgaccct ttttgaaaag tttatgtttg accttgcctt tatttacaac 120
tattc 125

<210> SEQ ID NO 282
<211> LENGTH: 125
<212> TYPE: DNA
<213> ORGANISM: Homo sapiens

<400> SEQUENCE: 282
tagatatttt ccttttctgt tacaggattc ctcatgtcca taacatgttg gatgaggctc 60
tgcagctcac ccccactctc agagtggtca gtctccatta attggacccc gtgatttcca 120
atctc 125

<210> SEQ ID NO 283
<211> LENGTH: 125
<212> TYPE: DNA
<213> ORGANISM: Homo sapiens

<400> SEQUENCE: 283
caaaaaagga atcctaatgc tacagaactg ccactcctac cacctcctcc aagcctaccc 60
accattggag cagagactag acgtagaaaa gcacgacgga aagagctaga gatggagcag 120
cagaa 125

<210> SEQ ID NO 284
<211> LENGTH: 125
<212> TYPE: DNA
<213> ORGANISM: Homo sapiens

<400> SEQUENCE: 284
tgggtaattt tttgtatttt agtagagacg gagtttcacc atgttggcca cgacggtctc 60
aatctcccga cctcatgatc ttcccacctc agcctcccaa agtactggga ttacaggcgt 120
gagcc 125

<210> SEQ ID NO 285
<211> LENGTH: 125
<212> TYPE: DNA
<213> ORGANISM: Homo sapiens

<400> SEQUENCE: 285
taagtcatca tctgcttgtc ctcaggtaat aaattatgcc agaagatgaa tacggtgatc 60
aaagacagac attttactgc ctttggtttc ctaaaaagaa tacatggtta aaagatgaag 120
aaaaa 125

<210> SEQ ID NO 286
<211> LENGTH: 125
<212> TYPE: DNA
<213> ORGANISM: Homo sapiens

<400> SEQUENCE: 286
gagatggagc ctccttgctg tgcagagaag ctggacgaga tgctggcagc cgccgcagag 60
ccaacgctgc ggccagacat cgcagacgca gactccagag ccgccaccgt caaacagagg 120
cccac 125

<210> SEQ ID NO 287
<211> LENGTH: 125
<212> TYPE: DNA
<213> ORGANISM: Homo sapiens

<400> SEQUENCE: 287
atctctgtgt ctccaaatct ccctctccat ataaagacac cagtttttat aaggtgggtt 60
aagggtccac tctaattcag tatggcctct ttttttgag atggaatatc gctcttgttt 120
cccag 125

<210> SEQ ID NO 288
<211> LENGTH: 125
<212> TYPE: DNA
<213> ORGANISM: Homo sapiens

<400> SEQUENCE: 288
atgctgcccg atcaacccgc tccctcctcc actcccatct gaccccagac ccacaaccct 60
actccatgcc ctctcagaac ccgcctctgg agccgcaggc tgcagacagc tcttgctccc 120
ctggg 125

<210> SEQ ID NO 289
<211> LENGTH: 125
<212> TYPE: DNA
<213> ORGANISM: Homo sapiens

<400> SEQUENCE: 289
cgaaccccga gctgcgcctg gaggcgcccg gcgcatcgga gccgctgcac caccacccct 60
acaaatatcc ggccgccgcc tacgaccact atctcggggc caagagccgg ccggcgccct 120
acccg 125

<210> SEQ ID NO 290
<211> LENGTH: 125
<212> TYPE: DNA
<213> ORGANISM: Homo sapiens

<400> SEQUENCE: 290
aggaatacgt tcccccagcc ccaggggcca ccgcggctct ccccttcccc agcctcgaag 60
ccatgggggc cccctcgcca cccccagccc cttgggctat cgaagtatcc ggttccccag 120
tccct 125

<210> SEQ ID NO 291
<211> LENGTH: 125
<212> TYPE: DNA
<213> ORGANISM: Homo sapiens

<400> SEQUENCE: 291
tcctcagacc cccgcccccc tgcaggaggg agcaccagct ccgtagagga ggggcagacg 60
tggactggtt cttgtcaggg cagcagaaag gcccttggtg cgcttctcct aacactcccc 120
tatcc 125

<210> SEQ ID NO 292
<211> LENGTH: 125
<212> TYPE: DNA
<213> ORGANISM: Homo sapiens

<400> SEQUENCE: 292
ctataattct caccccttagg tttgtggagg tgaaaaagcc aagtcaaatg ttagcctcca 60
ttgttaacat cccctattca ttttcaggac agctacaatg gaagcagctg gaattcaact 120
ctccc 125

<210> SEQ ID NO 293
<211> LENGTH: 125
<212> TYPE: DNA
<213> ORGANISM: Homo sapiens

<400> SEQUENCE: 293
tgcccacctc agcctcccaa agtgctggga ttacaggcgt gagtcatatc acccagccct 60

-continued ctttacatat tattcttcaa acacctcaaa aatcattctc ctgctgcatg ctgtggctcc 120
tgcaa 125

<210> SEQ ID NO 294
<211> LENGTH: 125
<212> TYPE: DNA
<213> ORGANISM: Homo sapiens

<400> SEQUENCE: 294
tatatatgat ggctgggctt agcagatgtg tagattctcc tattgctggg tcccactttt 60
ctgttaaggc ttacttcctt actgcttttg cccaaattat ttcttgtaga agcactggat 120
aaatg 125

<210> SEQ ID NO 295
<211> LENGTH: 125
<212> TYPE: DNA
<213> ORGANISM: Homo sapiens

<400> SEQUENCE: 295
ctctctcctg ctgtgccatg tgaagatgtg cctgcttccc ctttgtctgc tgtgactata 60
ggtttcctga ggcctcccca gccatgcatc ctgtacagcc tgtggaactg tgagtcaatt 120
aaact 125

<210> SEQ ID NO 296
<211> LENGTH: 125
<212> TYPE: DNA
<213> ORGANISM: Homo sapiens

<400> SEQUENCE: 296
atagggagtc ccatctccat agttctgtaa ataaaatgac agtgtaagtt attattttat 60
attaataaac agcacataaa caaacatagc tccactacca aaacttctcc cctccaaaga 120
aattg 125

<210> SEQ ID NO 297
<211> LENGTH: 125
<212> TYPE: DNA
<213> ORGANISM: Homo sapiens

<400> SEQUENCE: 297
ctgccagtcg gtcggtgtgg gacaaaacac agatatacag cagatagcgg ccaaaaactt 60
cacagacacc tctctcatgt acccagagga cacttgtaaa tctggaccaa gtacgaatac 120
acaga 125

<210> SEQ ID NO 298
<211> LENGTH: 125
<212> TYPE: DNA
<213> ORGANISM: Homo sapiens

<400> SEQUENCE: 298
agggctgggc gcggtggttc acgcctgtaa tcccagcact ttgggaggcc taggcgagca 60
gatcatctga ggtcgggagt tcgagaccag cctgaccaac atggagaaac cccgtctctc 120
ctaaa 125

<210> SEQ ID NO 299
<211> LENGTH: 125
<212> TYPE: DNA

-continued

```
<213> ORGANISM: Homo sapiens

<400> SEQUENCE: 299

tcacgaattt gtttctgtcc cctaggagcg gggtgccctg agctttgagc ggcgctacca      60

tgtcactgac ccctttatcc ggcggctggg cctggaagca gagctgcagg taagagatcc     120

agttt                                                                 125


<210> SEQ ID NO 300
<211> LENGTH: 125
<212> TYPE: DNA
<213> ORGANISM: Homo sapiens

<400> SEQUENCE: 300

tttaatttaa tttattttat ttgagatgga gtctcactct gttgcccagg ctggagtgca      60

atggcatgat ctcatctcac cacagcctcc gcctcctggg ttcaagtgat tctcctgcct     120

cagcc                                                                 125


<210> SEQ ID NO 301
<211> LENGTH: 50
<212> TYPE: RNA
<213> ORGANISM: Homo sapiens

<400> SEQUENCE: 301

cagccugauu cugccuguga cucacuuugu gaccucagga gagucccucc                50
```